(12) United States Patent
Tao et al.

(10) Patent No.: US 12,168,660 B2
(45) Date of Patent: *Dec. 17, 2024

(54) DERIVATIVES OF AN FGFR INHIBITOR

(71) Applicant: Incyte Corporation, Wilmington, DE (US)

(72) Inventors: Ming Tao, Maple Glen, PA (US); Jason Boer, Landenberg, PA (US)

(73) Assignee: Incyte Corporation, Wilmington, DE (US)

( * ) Notice: Subject to any disclaimer, the term of this patent is extended or adjusted under 35 U.S.C. 154(b) by 202 days.

This patent is subject to a terminal disclaimer.

(21) Appl. No.: 17/814,350

(22) Filed: Jul. 22, 2022

(65) Prior Publication Data

US 2022/0411423 A1 Dec. 29, 2022

Related U.S. Application Data

(63) Continuation of application No. 17/110,875, filed on Dec. 3, 2020, now Pat. No. 11,407,750.

(60) Provisional application No. 62/943,406, filed on Dec. 4, 2019.

(51) Int. Cl.
*A61K 31/5377* (2006.01)
*A61K 9/00* (2006.01)
*A61K 31/519* (2006.01)
*C07D 471/14* (2006.01)

(52) U.S. Cl.
CPC .......... *C07D 471/14* (2013.01); *A61K 9/0053* (2013.01)

(58) Field of Classification Search
CPC .... A61K 31/519; A61K 31/5377; A61P 35/00
USPC ............................................. 514/257, 232.8
See application file for complete search history.

(56) References Cited

U.S. PATENT DOCUMENTS

| | | |
|---|---|---|
| 850,370 A | 4/1907 | Hynes |
| 3,894,021 A | 7/1975 | Denzel et al. |
| 4,271,074 A | 6/1981 | Lohmann et al. |
| 4,339,267 A | 7/1982 | Levitt |
| 4,347,348 A | 8/1982 | Chernikhov et al. |
| 4,402,878 A | 9/1983 | D'Alelio et al. |
| 4,405,519 A | 9/1983 | D'Alelio et al. |
| 4,405,520 A | 9/1983 | D'Alelio et al. |
| 4,405,786 A | 9/1983 | D'Alelio et al. |
| 4,460,773 A | 7/1984 | Suzuki et al. |
| 4,874,803 A | 10/1989 | Baron et al. |
| 4,940,705 A | 7/1990 | Boshagen et al. |
| 5,159,054 A | 10/1992 | Keller |
| 5,240,941 A | 8/1993 | Bruneau |
| 5,480,887 A | 1/1996 | Hornback et al. |
| 5,521,184 A | 5/1996 | Zimmermann et al. |
| 5,536,725 A | 7/1996 | Cullen et al. |
| 5,541,324 A | 7/1996 | TenBrink et al. |
| 5,760,068 A | 6/1998 | Talley et al. |
| 5,783,577 A | 7/1998 | Houghten et al. |
| 5,845,025 A | 12/1998 | Garito et al. |
| 5,994,364 A | 11/1999 | Njoroge et al. |
| 6,465,484 B1 | 10/2002 | Bilodeau et al. |
| 6,998,408 B2 | 2/2006 | Pinto |
| 7,074,801 B1 | 7/2006 | Yoshida et al. |
| 7,125,880 B1 | 10/2006 | Chen |
| 7,488,802 B2 | 2/2009 | Collins et al. |
| 7,589,101 B2 | 9/2009 | Okram et al. |
| 7,618,975 B2 | 11/2009 | Cai et al. |
| 7,642,255 B2 | 1/2010 | Sim |
| 7,648,973 B2 | 1/2010 | DeLuca et al. |
| 7,846,923 B2 | 12/2010 | Ren et al. |
| 7,868,018 B2 | 1/2011 | Xie et al. |
| 7,943,743 B2 | 5/2011 | Korman et al. |
| 8,008,449 B2 | 8/2011 | Korman et al. |
| 8,119,655 B2 | 2/2012 | Dong et al. |
| 8,168,757 B2 | 5/2012 | Finnefrock et al. |
| 8,183,248 B2 | 5/2012 | Nagle et al. |
| 8,217,149 B2 | 7/2012 | Irving et al. |
| 8,426,411 B2 | 4/2013 | Wishart et al. |
| 8,461,328 B2 | 6/2013 | Babu et al. |
| 8,759,398 B2 | 1/2014 | Nelson |
| 8,754,114 B2 | 6/2014 | Yao et al. |
| 8,889,711 B2 | 11/2014 | Bedjeguelal |
| 9,266,892 B2 | 2/2016 | Zhuo et al. |
| 9,388,185 B2 | 7/2016 | Lu et al. |
| 9,440,976 B2 | 9/2016 | Dyke et al. |
| 9,533,954 B2 | 1/2017 | Yao et al. |
| 9,533,984 B2 | 1/2017 | Sun et al. |
| 9,580,423 B2 | 2/2017 | Lu et al. |
| 9,611,267 B2 | 4/2017 | Wu et al. |
| 9,708,318 B2 | 7/2017 | Lu et al. |
| 9,745,311 B2 | 8/2017 | Lu et al. |

(Continued)

FOREIGN PATENT DOCUMENTS

| | | |
|---|---|---|
| CL | 2014003355 | 6/2015 |
| CL | 2015002628 | 8/2016 |

(Continued)

OTHER PUBLICATIONS

Chilean Office Action in Chilean Application No. 202002848, dated Dec. 12, 2022, 36 pages (with machine translation).

(Continued)

*Primary Examiner* — Charanjit Aulakh

(74) *Attorney, Agent, or Firm* — Fish & Richardson P.C.

(57) ABSTRACT

The present disclosure relates to derivatives (e.g., hydroxyl, keto, glucuronide, sulfonic acid, and deuterated) of a Fibroblast Growth Factor Receptors (FGFR) inhibitor, including methods of preparation thereof, and intermediates in the preparation thereof, which are useful in the treatment of FGFR mediated disease such as cancer.

19 Claims, 5 Drawing Sheets

Specification includes a Sequence Listing.

(56) References Cited

U.S. PATENT DOCUMENTS

| | | |
|---|---|---|
| 9,801,889 B2 | 10/2017 | Lu et al. |
| 9,890,156 B2 | 2/2018 | Lu et al. |
| 10,016,348 B2 | 7/2018 | Lu et al. |
| 10,040,790 B2 | 8/2018 | Sun et al. |
| 10,131,667 B2 | 11/2018 | Wu et al. |
| 10,208,024 B2 | 2/2019 | Andrews et al. |
| 10,213,427 B2 | 2/2019 | Yao et al. |
| 10,214,528 B2 | 2/2019 | Lu et al. |
| 10,251,892 B2 | 4/2019 | Sokolsky et al. |
| 10,308,644 B2 | 6/2019 | Wu et al. |
| 10,350,240 B2 | 6/2019 | Gore et al. |
| 10,357,431 B2 | 7/2019 | Staric et al. |
| 10,450,313 B2 | 10/2019 | Lu et al. |
| 10,611,762 B2 | 4/2020 | Jia et al. |
| 10,632,126 B2 | 4/2020 | Lu et al. |
| 10,738,048 B2 | 8/2020 | Lu et al. |
| 10,813,930 B2 | 10/2020 | Yao et al. |
| 10,851,105 B2 | 12/2020 | Wu et al. |
| 10,947,230 B2 | 3/2021 | Sun et al. |
| 11,014,923 B2 | 5/2021 | Lu et al. |
| 11,053,246 B2 | 7/2021 | Wu et al. |
| 11,173,162 B2 | 11/2021 | Sokolsky et al. |
| 11,174,257 B2 | 11/2021 | Jia et al. |
| 11,407,750 B2 | 8/2022 | Tao et al. |
| 11,466,004 B2 | 10/2022 | Burn |
| 11,472,801 B2 | 10/2022 | Pan et al. |
| 11,530,214 B2 | 12/2022 | Lu et al. |
| 11,628,162 B2 | 4/2023 | Ji et al. |
| 11,667,635 B2 | 6/2023 | Lu et al. |
| 11,840,534 B2 | 12/2023 | Wu et al. |
| 12,024,517 B2 | 7/2024 | Jia et al. |
| 2003/0078255 A1 | 4/2003 | Pinto |
| 2003/0078277 A1 | 4/2003 | Hibi et al. |
| 2003/0181622 A1 | 9/2003 | Chiu et al. |
| 2004/0044012 A1 | 3/2004 | Dobrusin et al. |
| 2004/0067948 A1 | 4/2004 | Hallett |
| 2004/0097493 A1 | 5/2004 | Chen et al. |
| 2004/0122029 A1 | 6/2004 | Liu et al. |
| 2004/0127538 A1 | 7/2004 | Oinuma et al. |
| 2004/0204427 A1 | 10/2004 | Chen et al. |
| 2005/0009876 A1 | 1/2005 | Bhagwat et al. |
| 2005/0070542 A1 | 3/2005 | Hodgetts et al. |
| 2005/0148603 A1 | 7/2005 | Jimenez et al. |
| 2005/0197340 A1 | 9/2005 | Arora et al. |
| 2005/0222171 A1 | 10/2005 | Bold et al. |
| 2006/0222637 A1 | 10/2006 | Bamdad |
| 2006/0270849 A1 | 11/2006 | Nishino et al. |
| 2007/0116984 A1 | 5/2007 | Park et al. |
| 2007/0197510 A1 | 8/2007 | Ohmoto et al. |
| 2007/0225286 A1 | 9/2007 | Ren et al. |
| 2007/0280943 A1 | 12/2007 | Friedman et al. |
| 2008/0221098 A1 | 9/2008 | Sim et al. |
| 2008/0249301 A1 | 10/2008 | Hornberger et al. |
| 2009/0098086 A1 | 4/2009 | Zask et al. |
| 2009/0099165 A1 | 4/2009 | Hurley et al. |
| 2009/0099190 A1 | 4/2009 | Flynn et al. |
| 2009/0105233 A1 | 4/2009 | Chua et al. |
| 2009/0131467 A1 | 5/2009 | Kanazawa et al. |
| 2009/0163545 A1 | 6/2009 | Goldfarb |
| 2009/0246198 A1 | 10/2009 | Dong et al. |
| 2010/0032626 A1 | 2/2010 | Akino |
| 2010/0099684 A1 | 4/2010 | Cook, II et al. |
| 2010/0105661 A1 | 4/2010 | Shirakami et al. |
| 2010/0143547 A1 | 6/2010 | Kriegel et al. |
| 2010/0204235 A1 | 8/2010 | Lizos |
| 2010/0210636 A1 | 8/2010 | Ishikawa et al. |
| 2010/0216798 A1 | 8/2010 | Nakai et al. |
| 2010/0239496 A1 | 9/2010 | Gangadharmath et al. |
| 2011/0045511 A1 | 2/2011 | Graus Porta et al. |
| 2011/0118230 A1 | 5/2011 | Chen et al. |
| 2011/0159604 A1 | 6/2011 | Fan et al. |
| 2011/0160203 A1 | 6/2011 | Liu et al. |
| 2011/0178053 A1 | 7/2011 | Arendt et al. |
| 2011/0195968 A1 | 8/2011 | Greul et al. |
| 2011/0212077 A1 | 9/2011 | Noronha et al. |
| 2011/0224155 A1 | 9/2011 | Tachdjian et al. |
| 2011/0262525 A1 | 10/2011 | Wang et al. |
| 2011/0313003 A1 | 12/2011 | Shi et al. |
| 2012/0035153 A1 | 2/2012 | Saxty et al. |
| 2012/0135997 A1 | 5/2012 | Kato et al. |
| 2012/0165305 A1 | 6/2012 | Yao et al. |
| 2012/0295881 A1 | 11/2012 | Lange et al. |
| 2012/0319095 A1 | 12/2012 | Tada et al. |
| 2013/0078731 A1 | 3/2013 | George et al. |
| 2013/0200356 A1 | 8/2013 | Jung et al. |
| 2013/0210825 A1 | 8/2013 | Rehwinkel et al. |
| 2013/0338134 A1 | 12/2013 | Wu et al. |
| 2014/0045814 A1 | 2/2014 | Lu et al. |
| 2014/0054564 A1 | 2/2014 | Kim et al. |
| 2014/0080892 A1 | 3/2014 | Bhanot et al. |
| 2014/0088100 A1 | 3/2014 | Bifulco, Jr. et al. |
| 2014/0103325 A1 | 4/2014 | Shin et al. |
| 2014/0117318 A1 | 5/2014 | Choi et al. |
| 2014/0148548 A1 | 5/2014 | Yamanaka et al. |
| 2014/0171405 A1 | 6/2014 | Zhuo et al. |
| 2014/0187559 A1 | 7/2014 | Miduturu |
| 2014/0194430 A1 | 7/2014 | Eis et al. |
| 2014/0228370 A1 | 8/2014 | Eis et al. |
| 2014/0243308 A1 | 8/2014 | Yao et al. |
| 2014/0288069 A1 | 9/2014 | Eis et al. |
| 2014/0296233 A1 | 10/2014 | D'Agostino et al. |
| 2014/0315902 A1 | 10/2014 | Sun et al. |
| 2014/0374722 A1 | 12/2014 | Kim et al. |
| 2014/0378468 A1 | 12/2014 | Aichholz et al. |
| 2014/0378481 A1 | 12/2014 | Bifulco, Jr. et al. |
| 2014/0378483 A1 | 12/2014 | Benazet et al. |
| 2015/0011548 A1 | 1/2015 | Linnanen et al. |
| 2015/0011560 A1 | 1/2015 | Legeai-Mallet |
| 2015/0011579 A1 | 1/2015 | Clary-Ceccato et al. |
| 2015/0038485 A1 | 2/2015 | Eis et al. |
| 2015/0197519 A1 | 7/2015 | Bifulco |
| 2016/0115164 A1 | 4/2016 | Wu et al. |
| 2016/0244448 A1 | 8/2016 | Lu et al. |
| 2016/0244449 A1 | 8/2016 | Lu et al. |
| 2016/0244450 A1 | 8/2016 | Lu et al. |
| 2016/0280713 A1 | 9/2016 | Lu et al. |
| 2017/0107216 A1 | 4/2017 | Wu et al. |
| 2017/0119782 A1 | 5/2017 | Lu et al. |
| 2017/0137424 A1 | 5/2017 | Wu et al. |
| 2017/0145025 A1 | 5/2017 | Li et al. |
| 2017/0165263 A1 | 6/2017 | Yao et al. |
| 2017/0166564 A1 | 6/2017 | Sun et al. |
| 2017/0174671 A1 | 6/2017 | Wu et al. |
| 2017/0174679 A1 | 6/2017 | Lajkiewicz et al. |
| 2017/0260168 A1 | 9/2017 | Andrews et al. |
| 2017/0290839 A1 | 10/2017 | Lu et al. |
| 2017/0320875 A1 | 11/2017 | Li et al. |
| 2017/0320877 A1 | 11/2017 | Wu et al. |
| 2017/0342060 A1 | 11/2017 | Lu et al. |
| 2017/0362253 A1 | 12/2017 | Xiao et al. |
| 2018/0008610 A1 | 1/2018 | Lu et al. |
| 2018/0016260 A1 | 1/2018 | Yu et al. |
| 2018/0022713 A1 | 1/2018 | D'Agostino et al. |
| 2018/0057486 A1 | 3/2018 | Wu et al. |
| 2018/0072718 A1 | 3/2018 | Liu et al. |
| 2018/0177784 A1 | 6/2018 | Wu et al. |
| 2018/0177870 A1 | 6/2018 | Liu et al. |
| 2018/0179179 A1 | 6/2018 | Wu et al. |
| 2018/0179197 A1 | 6/2018 | Wu et al. |
| 2018/0179201 A1 | 6/2018 | Wu et al. |
| 2018/0179202 A1 | 6/2018 | Wu et al. |
| 2018/0244672 A1 | 8/2018 | Lu et al. |
| 2018/0273519 A1 | 9/2018 | Wu et al. |
| 2019/0040082 A1 | 2/2019 | Xiao et al. |
| 2019/0055237 A1 | 2/2019 | Pan et al. |
| 2019/0062327 A1 | 2/2019 | Sun et al. |
| 2019/0062345 A1 | 2/2019 | Xiao et al. |
| 2019/0071439 A1 | 3/2019 | Li et al. |
| 2019/0092767 A1 | 3/2019 | Li et al. |
| 2019/0127376 A1 | 5/2019 | Wu et al. |
| 2019/0127467 A1 | 5/2019 | Shah et al. |
| 2019/0144439 A1 | 5/2019 | Wu et al. |
| 2019/0202824 A1 | 7/2019 | Wu et al. |
| 2019/0225601 A1 | 7/2019 | Wu et al. |

(56) References Cited

U.S. PATENT DOCUMENTS

| | | | |
|---|---|---|---|
| 2019/0240220 A1 | 8/2019 | Yao et al. |
| 2019/0241560 A1 | 8/2019 | Lu et al. |
| 2019/0269693 A1 | 9/2019 | Lu et al. |
| 2019/0284187 A1 | 9/2019 | Wu et al. |
| 2019/0300524 A1 | 10/2019 | Wu et al. |
| 2019/0337948 A1 | 11/2019 | Frietze et al. |
| 2019/0345170 A1 | 11/2019 | Wu et al. |
| 2020/0002338 A1 | 1/2020 | Jia et al. |
| 2020/0055853 A1 | 2/2020 | Ellies et al. |
| 2020/0095244 A1 | 3/2020 | Sun et al. |
| 2020/0255424 A1 | 8/2020 | Wu et al. |
| 2020/0270245 A1 | 8/2020 | Pan et al. |
| 2020/0277309 A1 | 9/2020 | Wu et al. |
| 2020/0281907 A1 | 9/2020 | Ji et al. |
| 2020/0306256 A1 | 10/2020 | Lu et al. |
| 2020/0377504 A1 | 12/2020 | Wu et al. |
| 2020/0399267 A1 | 12/2020 | Lu et al. |
| 2021/0009582 A1 | 1/2021 | Vechorkin et al. |
| 2021/0094935 A1 | 4/2021 | Vechorkin |
| 2021/0106588 A1 | 4/2021 | Vechorkin et al. |
| 2021/0115053 A1 | 4/2021 | Shvartsbart et al. |
| 2021/0171522 A1 | 6/2021 | Tao et al. |
| 2021/0171535 A1 | 6/2021 | McCammant et al. |
| 2021/0214366 A1 | 7/2021 | Roach et al. |
| 2021/0380587 A1 | 12/2021 | Wu et al. |
| 2021/0395246 A1 | 12/2021 | Sun et al. |
| 2022/0009921 A1 | 1/2022 | Lu et al. |
| 2022/0153740 A1 | 5/2022 | Jia et al. |
| 2022/0324986 A1 | 10/2022 | Koblish et al. |
| 2023/0121695 A1 | 4/2023 | Frietze et al. |
| 2023/0218591 A1 | 7/2023 | Ji et al. |

FOREIGN PATENT DOCUMENTS

| | | |
|---|---|---|
| CL | 2017000654 | 12/2017 |
| CL | 2018000089 | 5/2018 |
| CL | 2018000124 | 5/2018 |
| CL | 2017002117 | 6/2018 |
| CL | 2018000036 | 6/2018 |
| CL | 2018000128 | 6/2018 |
| CL | 2018003322 | 1/2019 |
| CN | 1863774 | 11/2006 |
| CN | 101007778 | 8/2007 |
| CN | 101679408 | 3/2010 |
| CN | 101715451 | 5/2010 |
| CN | 102399220 | 4/2012 |
| CN | 102399233 | 4/2012 |
| CN | 102666536 | 9/2012 |
| CN | 103571502 | 2/2014 |
| CN | 103588771 | 2/2014 |
| CN | 104262330 | 1/2015 |
| CN | 107652289 | 2/2018 |
| DE | 2156720 | 5/1973 |
| DE | 2934578 | 3/1981 |
| DE | 3432983 | 4/1985 |
| DE | 280853 | 7/1990 |
| DE | 3937633 | 5/1991 |
| DE | 4119767 | 12/1992 |
| DE | 19912638 | 9/2000 |
| EA | 201590005 | 5/2015 |
| EP | 0466452 | 1/1992 |
| EP | 0995751 | 4/2000 |
| EP | 1199070 | 4/2002 |
| EP | 1217000 | 6/2002 |
| EP | 1388541 | 2/2004 |
| EP | 2651404 | 10/2015 |
| EP | 3184521 | 6/2017 |
| FR | 2428654 | 1/1980 |
| FR | 2876582 | 4/2006 |
| FR | 2983196 | 5/2013 |
| FR | 2983199 | 5/2013 |
| FR | 2983200 | 5/2013 |
| JP | 62273979 | 11/1987 |
| JP | 63017882 | 1/1988 |
| JP | S 6310630 | 1/1988 |
| JP | 02009895 | 1/1990 |
| JP | H 0348656 | 3/1991 |
| JP | H 03275669 | 12/1991 |
| JP | 04179576 | 6/1992 |
| JP | H 04158084 | 6/1992 |
| JP | H 04328121 | 11/1992 |
| JP | H 05320173 | 12/1993 |
| JP | H 05320515 | 12/1993 |
| JP | H 09188812 | 7/1997 |
| JP | H 1060426 | 3/1998 |
| JP | H 11171865 | 6/1999 |
| JP | 2000123973 | 4/2000 |
| JP | 2001035664 | 2/2001 |
| JP | 2001265031 | 9/2001 |
| JP | 2002516327 | 6/2002 |
| JP | 2002296731 | 10/2002 |
| JP | 2003335788 | 11/2003 |
| JP | 2004203749 | 7/2004 |
| JP | 2004346145 | 12/2004 |
| JP | 2005015395 | 1/2005 |
| JP | 2005320288 | 11/2005 |
| JP | 2006028027 | 2/2006 |
| JP | 2006514624 | 5/2006 |
| JP | 2006284843 | 10/2006 |
| JP | 2006522756 | 10/2006 |
| JP | 2006316054 | 11/2006 |
| JP | 2007500725 | 1/2007 |
| JP | 2008198769 | 8/2008 |
| JP | 2009537520 | 10/2009 |
| JP | 2010180147 | 8/2010 |
| JP | 2010248429 | 11/2010 |
| JP | 2010267847 | 11/2010 |
| JP | 2010270245 | 12/2010 |
| JP | 2010272618 | 12/2010 |
| JP | 2010272727 | 12/2010 |
| JP | 2010278114 | 12/2010 |
| JP | 2011009348 | 1/2011 |
| JP | 2011044637 | 3/2011 |
| JP | 2011116840 | 6/2011 |
| JP | 2011222650 | 11/2011 |
| JP | 2012116825 | 6/2012 |
| JP | 2012136476 | 7/2012 |
| JP | 5120580 | 1/2013 |
| JP | 2013049251 | 3/2013 |
| JP | 2013179181 | 9/2013 |
| JP | 2018507214 | 3/2018 |
| JP | 2018511573 | 4/2018 |
| JP | 6336665 | 6/2018 |
| KR | 20010043829 | 5/2001 |
| KR | 20080045536 | 5/2008 |
| KR | 20110023190 | 3/2011 |
| KR | 20110043270 | 4/2011 |
| KR | 20120052034 | 5/2012 |
| KR | 20120078303 | 7/2012 |
| KR | 20130043460 | 4/2013 |
| KR | 20140090411 | 7/2014 |
| KR | 20140099105 | 8/2014 |
| TW | 200602319 | 1/2006 |
| WO | WO 1988/03025 | 5/1988 |
| WO | WO 1991/09835 | 7/1991 |
| WO | WO 1991/10172 | 7/1991 |
| WO | WO 1992/06078 | 4/1992 |
| WO | WO 1992/22552 | 12/1992 |
| WO | WO 1993/24488 | 12/1993 |
| WO | WO 1994/13669 | 6/1994 |
| WO | WO 1994/15995 | 7/1994 |
| WO | WO 1994/25438 | 11/1994 |
| WO | WO 1995/20965 | 8/1995 |
| WO | WO 1996/15128 | 5/1996 |
| WO | WO 1996/40707 | 12/1996 |
| WO | WO 1997/47601 | 12/1997 |
| WO | WO 1998/05661 | 2/1998 |
| WO | WO 1998/06703 | 2/1998 |
| WO | WO 1998/11438 | 3/1998 |
| WO | WO 1998/18781 | 5/1998 |
| WO | WO 1998/28281 | 7/1998 |
| WO | WO 1998/33798 | 8/1998 |
| WO | WO 1998/46609 | 10/1998 |
| WO | WO 1998/54156 | 12/1998 |

(56) References Cited

FOREIGN PATENT DOCUMENTS

| | | |
|---|---|---|
| WO | WO 1999/06422 | 2/1999 |
| WO | WO 1999/07732 | 2/1999 |
| WO | WO 1999/09030 | 2/1999 |
| WO | WO 1999/42442 | 8/1999 |
| WO | WO 1999/59975 | 11/1999 |
| WO | WO 1999/61444 | 12/1999 |
| WO | WO 1999/64400 | 12/1999 |
| WO | WO 2000/09495 | 2/2000 |
| WO | WO 2002/000196 | 2/2000 |
| WO | WO 2000/24744 | 5/2000 |
| WO | WO 2000/053595 | 9/2000 |
| WO | WO 2000/68186 | 11/2000 |
| WO | WO 2001/02369 | 1/2001 |
| WO | WO 2001/014402 | 3/2001 |
| WO | WO 2001/22938 | 4/2001 |
| WO | WO 2001/23386 | 4/2001 |
| WO | WO 2001/29041 | 4/2001 |
| WO | WO 2001/29042 | 4/2001 |
| WO | WO 2001/42247 | 6/2001 |
| WO | WO 2001/47892 | 7/2001 |
| WO | WO 2001/53273 | 7/2001 |
| WO | WO 2001/55148 | 8/2001 |
| WO | WO 2001/57037 | 8/2001 |
| WO | WO 2001/57038 | 8/2001 |
| WO | WO 2001/58899 | 8/2001 |
| WO | WO 2001/64655 | 9/2001 |
| WO | WO 2001/66099 | 9/2001 |
| WO | WO 2001/68647 | 9/2001 |
| WO | WO 2001/83472 | 11/2001 |
| WO | WO 2001/85722 | 11/2001 |
| WO | WO 2002/00655 | 1/2002 |
| WO | WO 2002/12442 | 2/2002 |
| WO | WO 2002/14315 | 2/2002 |
| WO | WO 2002/20011 | 3/2002 |
| WO | WO 2002/051831 | 7/2002 |
| WO | WO 2002/055082 | 7/2002 |
| WO | WO 2002/066481 | 8/2002 |
| WO | WO 2002/74754 | 9/2002 |
| WO | WO 2002/076953 | 10/2002 |
| WO | WO 2002/083648 | 10/2002 |
| WO | WO 2002/088095 | 11/2002 |
| WO | WO 2002/094825 | 11/2002 |
| WO | WO 2002/096873 | 12/2002 |
| WO | WO 2002/102793 | 12/2002 |
| WO | WO 2003/000187 | 1/2003 |
| WO | WO 2003/000688 | 1/2003 |
| WO | WO 2003/000690 | 1/2003 |
| WO | WO 2003/009852 | 2/2003 |
| WO | WO 2003/014083 | 2/2003 |
| WO | WO 2003/024967 | 3/2003 |
| WO | WO 2003/037347 | 5/2003 |
| WO | WO 2003/037891 | 5/2003 |
| WO | WO 2003/040131 | 5/2003 |
| WO | WO 2003/042402 | 5/2003 |
| WO | WO 2003/049542 | 6/2003 |
| WO | WO 2003/062236 | 7/2003 |
| WO | WO 2003/075836 | 9/2003 |
| WO | WO 2003/082871 | 10/2003 |
| WO | WO 2003/097609 | 11/2003 |
| WO | WO 2003/099771 | 12/2003 |
| WO | WO 2003/099818 | 12/2003 |
| WO | WO 2003/101985 | 12/2003 |
| WO | WO 2004/002986 | 1/2004 |
| WO | WO 2004/005281 | 1/2004 |
| WO | WO 2004/011465 | 2/2004 |
| WO | WO 2004/014382 | 2/2004 |
| WO | WO 2004/014907 | 2/2004 |
| WO | WO 2004/018472 | 3/2004 |
| WO | WO 2004/020441 | 3/2004 |
| WO | WO 2004/041821 | 5/2004 |
| WO | WO 2004/041822 | 5/2004 |
| WO | WO 2004/041823 | 5/2004 |
| WO | WO 2004/043367 | 5/2004 |
| WO | WO 2004/046120 | 6/2004 |
| WO | WO 2004/046152 | 6/2004 |
| WO | WO 2004/048343 | 6/2004 |
| WO | WO 2004/052291 | 6/2004 |
| WO | WO 2004/052862 | 6/2004 |
| WO | WO 2004/056786 | 7/2004 |
| WO | WO 2004/056822 | 7/2004 |
| WO | WO 2004/056830 | 7/2004 |
| WO | WO 2004/065378 | 8/2004 |
| WO | WO 2004/080980 | 9/2004 |
| WO | WO 2004/083177 | 9/2004 |
| WO | WO 2004/087053 | 10/2004 |
| WO | WO 2004/089955 | 10/2004 |
| WO | WO 2004/094420 | 11/2004 |
| WO | WO 2004/099209 | 11/2004 |
| WO | WO 2004/108139 | 11/2004 |
| WO | WO 2004/110487 | 12/2004 |
| WO | WO 2004/112793 | 12/2004 |
| WO | WO 2004/113307 | 12/2004 |
| WO | WO 2005/007653 | 1/2005 |
| WO | WO 2005/011597 | 2/2005 |
| WO | WO 2005/021533 | 3/2005 |
| WO | WO 2005/028434 | 3/2005 |
| WO | WO 2005/028478 | 3/2005 |
| WO | WO 2005/028480 | 3/2005 |
| WO | WO 2005/028444 | 5/2005 |
| WO | WO 2005/040119 | 5/2005 |
| WO | WO 2005/047289 | 5/2005 |
| WO | WO 2005/056524 | 6/2005 |
| WO | WO 2005/063768 | 6/2005 |
| WO | WO 2005/066162 | 7/2005 |
| WO | WO 2005/070430 | 8/2005 |
| WO | WO 2005/070929 | 8/2005 |
| WO | WO 2005/072412 | 8/2005 |
| WO | WO 2005/073232 | 8/2005 |
| WO | WO 2005/080393 | 9/2005 |
| WO | WO 2005/082903 | 9/2005 |
| WO | WO 2005/085210 | 9/2005 |
| WO | WO 2005/085248 | 9/2005 |
| WO | WO 2005/085249 | 9/2005 |
| WO | WO 2005/087765 | 9/2005 |
| WO | WO 2005/092901 | 10/2005 |
| WO | WO 2005/105097 | 11/2005 |
| WO | WO 2005/113536 | 12/2005 |
| WO | WO 2005/116035 | 12/2005 |
| WO | WO 2005/121130 | 12/2005 |
| WO | WO 2005/121142 | 12/2005 |
| WO | WO 2006/000420 | 1/2006 |
| WO | WO 2006/024486 | 3/2006 |
| WO | WO 2006/024487 | 3/2006 |
| WO | WO 2006/024834 | 3/2006 |
| WO | WO 2006/028289 | 3/2006 |
| WO | WO 2006/030031 | 3/2006 |
| WO | WO 2006/038112 | 4/2006 |
| WO | WO 2006/050076 | 5/2006 |
| WO | WO 2006/050162 | 5/2006 |
| WO | WO 2006/052712 | 5/2006 |
| WO | WO 2006/055752 | 5/2006 |
| WO | WO 2006/024524 | 6/2006 |
| WO | WO 2006/056399 | 6/2006 |
| WO | WO 2006/058120 | 6/2006 |
| WO | WO 2006/062465 | 6/2006 |
| WO | WO 2006/065703 | 6/2006 |
| WO | WO 2006/074293 | 7/2006 |
| WO | WO 2006/087230 | 8/2006 |
| WO | WO 2006/092691 | 9/2006 |
| WO | WO 2006/102588 | 9/2006 |
| WO | WO 2006/102610 | 9/2006 |
| WO | WO 2006/105448 | 10/2006 |
| WO | WO 2006/107644 | 10/2006 |
| WO | WO 2006/112666 | 10/2006 |
| WO | WO 2006/119504 | 11/2006 |
| WO | WO 2006/124462 | 11/2006 |
| WO | WO 2006/124731 | 11/2006 |
| WO | WO 2006/135821 | 12/2006 |
| WO | WO 2006/136442 | 12/2006 |
| WO | WO 2007/013964 | 2/2007 |
| WO | WO 2007/017096 | 2/2007 |
| WO | WO 2007/021795 | 2/2007 |
| WO | WO 2007/022268 | 2/2007 |
| WO | WO 2007/023105 | 3/2007 |

(56) References Cited

FOREIGN PATENT DOCUMENTS

| | | |
|---|---|---|
| WO | WO 2007/025949 | 3/2007 |
| WO | WO 2007/030366 | 3/2007 |
| WO | WO 2007/032466 | 3/2007 |
| WO | WO 2007/033780 | 3/2007 |
| WO | WO 2007/038209 | 4/2007 |
| WO | WO 2007/044698 | 4/2007 |
| WO | WO 2007/044729 | 4/2007 |
| WO | WO 2007/048802 | 5/2007 |
| WO | WO 2007/053135 | 5/2007 |
| WO | WO 2007/053452 | 5/2007 |
| WO | WO 2007/053498 | 5/2007 |
| WO | WO 2007/055418 | 5/2007 |
| WO | WO 2007/056023 | 5/2007 |
| WO | WO 2007/056075 | 5/2007 |
| WO | WO 2007/056170 | 5/2007 |
| WO | WO 2007/058392 | 5/2007 |
| WO | WO 2007/058626 | 5/2007 |
| WO | WO 2007/059108 | 5/2007 |
| WO | WO 2007/061554 | 5/2007 |
| WO | WO 2007/064883 | 6/2007 |
| WO | WO 2007/064931 | 6/2007 |
| WO | WO 2007/066189 | 6/2007 |
| WO | WO 2007/067444 | 6/2007 |
| WO | WO 2007/071752 | 6/2007 |
| WO | WO 2007/084314 | 7/2007 |
| WO | WO 2007/088999 | 8/2007 |
| WO | WO 2007/092879 | 8/2007 |
| WO | WO 2007/093901 | 8/2007 |
| WO | WO 2007/109334 | 9/2007 |
| WO | WO 2007/110868 | 10/2007 |
| WO | WO 2007/112347 | 10/2007 |
| WO | WO 2007/120097 | 10/2007 |
| WO | WO 2007/120339 | 10/2007 |
| WO | WO 2007/125351 | 11/2007 |
| WO | WO 2007/125405 | 11/2007 |
| WO | WO 2007/126841 | 11/2007 |
| WO | WO 2007/134259 | 11/2007 |
| WO | WO 2007/136465 | 11/2007 |
| WO | WO 2007/140957 | 12/2007 |
| WO | WO 2007/143600 | 12/2007 |
| WO | WO 2007/147217 | 12/2007 |
| WO | WO 2008/001070 | 1/2008 |
| WO | WO 2008/003766 | 1/2008 |
| WO | WO 2008/005877 | 1/2008 |
| WO | WO 2008/008234 | 1/2008 |
| WO | WO 2008/008747 | 1/2008 |
| WO | WO 2008/012635 | 1/2008 |
| WO | WO 2008/021389 | 2/2008 |
| WO | WO 2008/021851 | 2/2008 |
| WO | WO 2008/025556 | 3/2008 |
| WO | WO 2008/033858 | 3/2008 |
| WO | WO 2008/033999 | 3/2008 |
| WO | WO 2008/034859 | 3/2008 |
| WO | WO 2008/034860 | 3/2008 |
| WO | WO 2008/037459 | 4/2008 |
| WO | WO 2008/042639 | 4/2008 |
| WO | WO 2008/052898 | 5/2008 |
| WO | WO 2008/052934 | 5/2008 |
| WO | WO 2008/060907 | 5/2008 |
| WO | WO 2008/063583 | 5/2008 |
| WO | WO 2008/063609 | 5/2008 |
| WO | WO 2008/064157 | 5/2008 |
| WO | WO 2008/071455 | 6/2008 |
| WO | WO 2008/074068 | 6/2008 |
| WO | WO 2008/075068 | 6/2008 |
| WO | WO 2008/076278 | 6/2008 |
| WO | WO 2008/078091 | 7/2008 |
| WO | WO 2008/078100 | 7/2008 |
| WO | WO 2008/079460 | 7/2008 |
| WO | WO 2008/079933 | 7/2008 |
| WO | WO 2008/085942 | 7/2008 |
| WO | WO 2008/089105 | 7/2008 |
| WO | WO 2008/099075 | 8/2008 |
| WO | WO 2008/107436 | 9/2008 |
| WO | WO 2008/107544 | 9/2008 |
| WO | WO 2008/109181 | 9/2008 |
| WO | WO 2008/109943 | 9/2008 |
| WO | WO 2008/115974 | 9/2008 |
| WO | WO 2008/117269 | 10/2008 |
| WO | WO 2008/118454 | 10/2008 |
| WO | WO 2008/123755 | 10/2008 |
| WO | WO 2008/128141 | 10/2008 |
| WO | WO 2008/130584 | 10/2008 |
| WO | WO 2008/131972 | 11/2008 |
| WO | WO 2008/141065 | 11/2008 |
| WO | WO 2008/142720 | 11/2008 |
| WO | WO 2008/144253 | 11/2008 |
| WO | WO 2008/151184 | 12/2008 |
| WO | WO 2008/153207 | 12/2008 |
| WO | WO 2008/153852 | 12/2008 |
| WO | WO 2008/154221 | 12/2008 |
| WO | WO 2008/156712 | 12/2008 |
| WO | WO 2009/013335 | 1/2009 |
| WO | WO 2009/013354 | 1/2009 |
| WO | WO 2009/097446 | 1/2009 |
| WO | WO 2009/016253 | 2/2009 |
| WO | WO 2009/019518 | 2/2009 |
| WO | WO 2009/021083 | 2/2009 |
| WO | WO 2009/029473 | 3/2009 |
| WO | WO 2009/029625 | 3/2009 |
| WO | WO 2009/030871 | 3/2009 |
| WO | WO 2009/032861 | 3/2009 |
| WO | WO 2009/036012 | 3/2009 |
| WO | WO 2009/044788 | 4/2009 |
| WO | WO 2009/046606 | 4/2009 |
| WO | WO 2009/047255 | 4/2009 |
| WO | WO 2009/047506 | 4/2009 |
| WO | WO 2009/047522 | 4/2009 |
| WO | WO 2009/047993 | 4/2009 |
| WO | WO 2009/049018 | 4/2009 |
| WO | WO 2009/050183 | 4/2009 |
| WO | WO 2009/053737 | 4/2009 |
| WO | WO 2009/055828 | 4/2009 |
| WO | WO 2009/056886 | 5/2009 |
| WO | WO 2009/071535 | 6/2009 |
| WO | WO 2009/073153 | 6/2009 |
| WO | WO 2009/085185 | 7/2009 |
| WO | WO 2009/086130 | 7/2009 |
| WO | WO 2009/086509 | 7/2009 |
| WO | WO 2009/087238 | 7/2009 |
| WO | WO 2009/092764 | 7/2009 |
| WO | WO 2009/093209 | 7/2009 |
| WO | WO 2009/093210 | 7/2009 |
| WO | WO 2009/094528 | 7/2009 |
| WO | WO 2009/099982 | 8/2009 |
| WO | WO 2009/103652 | 8/2009 |
| WO | WO 2009/105717 | 8/2009 |
| WO | WO 2009/108332 | 9/2009 |
| WO | WO 2009/108827 | 9/2009 |
| WO | WO 2009/112826 | 9/2009 |
| WO | WO 2009/114870 | 9/2009 |
| WO | WO 2009/114874 | 9/2009 |
| WO | WO 2009/122180 | 10/2009 |
| WO | WO 2009/123967 | 10/2009 |
| WO | WO 2009/124755 | 10/2009 |
| WO | WO 2009/125808 | 10/2009 |
| WO | WO 2009/125809 | 10/2009 |
| WO | WO 2009/126584 | 10/2009 |
| WO | WO 2009/128520 | 10/2009 |
| WO | WO 2009/131687 | 10/2009 |
| WO | WO 2009/131926 | 10/2009 |
| WO | WO 2009/132980 | 11/2009 |
| WO | WO 2009/133127 | 11/2009 |
| WO | WO 2009/141386 | 11/2009 |
| WO | WO 2009/144205 | 12/2009 |
| WO | WO 2009/144302 | 12/2009 |
| WO | WO 2009/146034 | 12/2009 |
| WO | WO 2009/148887 | 12/2009 |
| WO | WO 2009/148916 | 12/2009 |
| WO | WO 2009/150150 | 12/2009 |
| WO | WO 2009/150240 | 12/2009 |
| WO | WO 2009/151997 | 12/2009 |
| WO | WO 2009/153592 | 12/2009 |
| WO | WO 2009/157423 | 12/2009 |

(56) References Cited

FOREIGN PATENT DOCUMENTS

| | | |
|---|---|---|
| WO | WO 2010/006947 | 1/2010 |
| WO | WO 2010/007099 | 1/2010 |
| WO | WO 2010/007116 | 1/2010 |
| WO | WO 2010/009155 | 1/2010 |
| WO | WO 2010/009195 | 1/2010 |
| WO | WO 2010/009207 | 1/2010 |
| WO | WO 2010/009735 | 1/2010 |
| WO | WO 2010/015643 | 2/2010 |
| WO | WO 2010/017047 | 2/2010 |
| WO | WO 2010/019210 | 2/2010 |
| WO | WO 2010/019899 | 2/2010 |
| WO | WO 2010/030027 | 3/2010 |
| WO | WO 2010/036959 | 4/2010 |
| WO | WO 2010/038081 | 4/2010 |
| WO | WO 2010/045371 | 4/2010 |
| WO | WO 2010/049731 | 5/2010 |
| WO | WO 2010/051043 | 5/2010 |
| WO | WO 2010/052448 | 5/2010 |
| WO | WO 2010/059552 | 5/2010 |
| WO | WO 2010/059658 | 5/2010 |
| WO | WO 2010/062571 | 6/2010 |
| WO | WO 2010/064621 | 6/2010 |
| WO | WO 2010/064875 | 6/2010 |
| WO | WO 2010/067886 | 6/2010 |
| WO | WO 2010/067888 | 6/2010 |
| WO | WO 2010/075074 | 7/2010 |
| WO | WO 2010/077647 | 7/2010 |
| WO | WO 2010/077680 | 7/2010 |
| WO | WO 2010/078421 | 7/2010 |
| WO | WO 2010/078427 | 7/2010 |
| WO | WO 2010/080503 | 7/2010 |
| WO | WO 2010/080712 | 7/2010 |
| WO | WO 2010/083145 | 7/2010 |
| WO | WO 2010/083283 | 7/2010 |
| WO | WO 2010/086089 | 8/2010 |
| WO | WO 2010/089411 | 8/2010 |
| WO | WO 2010/092181 | 8/2010 |
| WO | WO 2010/099938 | 9/2010 |
| WO | WO 2010/103306 | 9/2010 |
| WO | WO 2010/104047 | 9/2010 |
| WO | WO 2010/107765 | 9/2010 |
| WO | WO 2010/107768 | 9/2010 |
| WO | WO 2010/111303 | 9/2010 |
| WO | WO 2010/111573 | 9/2010 |
| WO | WO 2010/115279 | 10/2010 |
| WO | WO 2010/117425 | 10/2010 |
| WO | WO 2010/119284 | 10/2010 |
| WO | WO 2010/119285 | 10/2010 |
| WO | WO 2010/117323 | 11/2010 |
| WO | WO 2010/125216 | 11/2010 |
| WO | WO 2010/126960 | 11/2010 |
| WO | WO 2010/127212 | 11/2010 |
| WO | WO 2010/129509 | 11/2010 |
| WO | WO 2010/136031 | 12/2010 |
| WO | WO 2010/142801 | 12/2010 |
| WO | WO 2010/151689 | 12/2010 |
| WO | WO 2011/002038 | 1/2011 |
| WO | WO 2011/007819 | 1/2011 |
| WO | WO 2011/011597 | 1/2011 |
| WO | WO 2011/012816 | 2/2011 |
| WO | WO 2011/014535 | 2/2011 |
| WO | WO 2011/015037 | 2/2011 |
| WO | WO 2011/016472 | 2/2011 |
| WO | WO 2011/016528 | 2/2011 |
| WO | WO 2011/018894 | 2/2011 |
| WO | WO 2011/022439 | 2/2011 |
| WO | WO 2011/026579 | 3/2011 |
| WO | WO 2011/028947 | 3/2011 |
| WO | WO 2011/031740 | 3/2011 |
| WO | WO 2011/032050 | 3/2011 |
| WO | WO 2011/039344 | 4/2011 |
| WO | WO 2011/041143 | 4/2011 |
| WO | WO 2011/042389 | 4/2011 |
| WO | WO 2011/042474 | 4/2011 |
| WO | WO 2011/045344 | 4/2011 |
| WO | WO 2011/049825 | 4/2011 |
| WO | WO 2011/049988 | 4/2011 |
| WO | WO 2011/050245 | 4/2011 |
| WO | WO 2011/051425 | 5/2011 |
| WO | WO 2011/053518 | 5/2011 |
| WO | WO 2011/054843 | 5/2011 |
| WO | WO 2011/055911 | 5/2011 |
| WO | WO 2011/057022 | 5/2011 |
| WO | WO 2011/060295 | 5/2011 |
| WO | WO 2011/062253 | 5/2011 |
| WO | WO 2011/062885 | 5/2011 |
| WO | WO 2011/063159 | 5/2011 |
| WO | WO 2011/066342 | 6/2011 |
| WO | WO 2011/068899 | 6/2011 |
| WO | WO 2011/071821 | 6/2011 |
| WO | WO 2011/075515 | 6/2011 |
| WO | WO 2011/075620 | 6/2011 |
| WO | WO 2011/077043 | 6/2011 |
| WO | WO 2011/077044 | 6/2011 |
| WO | WO 2011/079231 | 6/2011 |
| WO | WO 2011/080755 | 7/2011 |
| WO | WO 2011/082234 | 7/2011 |
| WO | WO 2011/082266 | 7/2011 |
| WO | WO 2011/082267 | 7/2011 |
| WO | WO 2011/082400 | 7/2011 |
| WO | WO 2011/082488 | 7/2011 |
| WO | WO 2011/087776 | 7/2011 |
| WO | WO 2011/090666 | 7/2011 |
| WO | WO 2011/090738 | 7/2011 |
| WO | WO 2011/090760 | 7/2011 |
| WO | WO 2011/093672 | 8/2011 |
| WO | WO 2011/094890 | 8/2011 |
| WO | WO 2011/097717 | 8/2011 |
| WO | WO 2011/101409 | 8/2011 |
| WO | WO 2011/101806 | 8/2011 |
| WO | WO 2011/102441 | 8/2011 |
| WO | WO 2011/103196 | 8/2011 |
| WO | WO 2011/103441 | 8/2011 |
| WO | WO 2011/103460 | 8/2011 |
| WO | WO 2011/103557 | 8/2011 |
| WO | WO 2011/105161 | 9/2011 |
| WO | WO 2011/109237 | 9/2011 |
| WO | WO 2011/111880 | 9/2011 |
| WO | WO 2011/112687 | 9/2011 |
| WO | WO 2011/112995 | 9/2011 |
| WO | WO 2011/115725 | 9/2011 |
| WO | WO 2011/119894 | 9/2011 |
| WO | WO 2011/120327 | 10/2011 |
| WO | WO 2011/123493 | 10/2011 |
| WO | WO 2011/128403 | 10/2011 |
| WO | WO 2011/130390 | 10/2011 |
| WO | WO 2011/133722 | 10/2011 |
| WO | WO 2011/133750 | 10/2011 |
| WO | WO 2011/133888 | 10/2011 |
| WO | WO 2011/135376 | 11/2011 |
| WO | WO 2011/137313 | 11/2011 |
| WO | WO 2011/140338 | 11/2011 |
| WO | WO 2011/141756 | 11/2011 |
| WO | WO 2011/141848 | 11/2011 |
| WO | WO 2011/143033 | 11/2011 |
| WO | WO 2011/143318 | 11/2011 |
| WO | WO 2011/143430 | 11/2011 |
| WO | WO 2011/147198 | 12/2011 |
| WO | WO 2011/147199 | 12/2011 |
| WO | WO 2011/151360 | 12/2011 |
| WO | WO 2011/153553 | 12/2011 |
| WO | WO 2011/155983 | 12/2011 |
| WO | WO 2011/156610 | 12/2011 |
| WO | WO 2011/159877 | 12/2011 |
| WO | WO 2011/161699 | 12/2011 |
| WO | WO 2011/163330 | 12/2011 |
| WO | WO 2012/000103 | 1/2012 |
| WO | WO 2012/003544 | 1/2012 |
| WO | WO 2012/004217 | 1/2012 |
| WO | WO 2012/004731 | 1/2012 |
| WO | WO 2012/004732 | 1/2012 |
| WO | WO 2012/008563 | 1/2012 |
| WO | WO 2012/008564 | 1/2012 |
| WO | WO 2012/008999 | 1/2012 |

(56) References Cited

FOREIGN PATENT DOCUMENTS

| | | |
|---|---|---|
| WO | WO 2012/009258 | 1/2012 |
| WO | WO 2012/009309 | 1/2012 |
| WO | WO 2012/013619 | 2/2012 |
| WO | WO 2012/015274 | 2/2012 |
| WO | WO 2012/019093 | 2/2012 |
| WO | WO 2012/020133 | 2/2012 |
| WO | WO 2012/027236 | 3/2012 |
| WO | WO 2012/027239 | 3/2012 |
| WO | WO 2012/030990 | 3/2012 |
| WO | WO 2012/031004 | 3/2012 |
| WO | WO 2012/032031 | 3/2012 |
| WO | WO 2012/032065 | 3/2012 |
| WO | WO 2012/032067 | 3/2012 |
| WO | WO 2012/032334 | 3/2012 |
| WO | WO 2012/035996 | 3/2012 |
| WO | WO 2012/036233 | 3/2012 |
| WO | WO 2012/038743 | 3/2012 |
| WO | WO 2012/047699 | 4/2012 |
| WO | WO 2012/054364 | 4/2012 |
| WO | WO 2012/057260 | 5/2012 |
| WO | WO 2012/058211 | 5/2012 |
| WO | WO 2012/061156 | 5/2012 |
| WO | WO 2012/061337 | 5/2012 |
| WO | WO 2012/062462 | 5/2012 |
| WO | WO 2012/063207 | 5/2012 |
| WO | WO 2012/064715 | 5/2012 |
| WO | WO 2012/065297 | 5/2012 |
| WO | WO 2012/065546 | 5/2012 |
| WO | WO 2012/066578 | 5/2012 |
| WO | WO 2012/068343 | 5/2012 |
| WO | WO 2012/073017 | 6/2012 |
| WO | WO 2012/078777 | 6/2012 |
| WO | WO 2012/080727 | 6/2012 |
| WO | WO 2012/080729 | 6/2012 |
| WO | WO 2012/083866 | 6/2012 |
| WO | WO 2012/083953 | 6/2012 |
| WO | WO 2012/083954 | 6/2012 |
| WO | WO 2012/084704 | 6/2012 |
| WO | WO 2012/087784 | 6/2012 |
| WO | WO 2012/088266 | 6/2012 |
| WO | WO 2012/091240 | 7/2012 |
| WO | WO 2012/093731 | 7/2012 |
| WO | WO 2012/098068 | 7/2012 |
| WO | WO 2012/101239 | 8/2012 |
| WO | WO 2012/106995 | 8/2012 |
| WO | WO 2012/112961 | 8/2012 |
| WO | WO 2012/112965 | 8/2012 |
| WO | WO 2012/116237 | 8/2012 |
| WO | WO 2012/125812 | 9/2012 |
| WO | WO 2012/127012 | 9/2012 |
| WO | WO 2012/129344 | 9/2012 |
| WO | WO 2012/134943 | 10/2012 |
| WO | WO 2012/138975 | 10/2012 |
| WO | WO 2012/140114 | 10/2012 |
| WO | WO 2012/158704 | 11/2012 |
| WO | WO 2012/158795 | 11/2012 |
| WO | WO 2012/158994 | 11/2012 |
| WO | WO 2012/161812 | 11/2012 |
| WO | WO 2012/167247 | 12/2012 |
| WO | WO 2012/173370 | 12/2012 |
| WO | WO 2013/016197 | 1/2013 |
| WO | WO 2013/024002 | 2/2013 |
| WO | WO 2013/024895 | 2/2013 |
| WO | WO 2013/033981 | 3/2013 |
| WO | WO 2013/039854 | 3/2013 |
| WO | WO 2013/041634 | 3/2013 |
| WO | WO 2013/049352 | 4/2013 |
| WO | WO 2013/053051 | 4/2013 |
| WO | WO 2013/063000 | 5/2013 |
| WO | WO 2013/063003 | 5/2013 |
| WO | WO 2013/108809 | 7/2013 |
| WO | WO 2013/109027 | 7/2013 |
| WO | WO 2013/124316 | 8/2013 |
| WO | WO 2013/136249 | 9/2013 |
| WO | WO 2013/144339 | 10/2013 |
| WO | WO 2014/007951 | 1/2014 |
| WO | WO 2014/011284 | 1/2014 |
| WO | WO 2014/011900 | 1/2014 |
| WO | WO 2014/019186 | 2/2014 |
| WO | WO 2014/022528 | 2/2014 |
| WO | WO 2014/026125 | 2/2014 |
| WO | WO 2014/044846 | 3/2014 |
| WO | WO 2014/048878 | 4/2014 |
| WO | WO 2014/062454 | 4/2014 |
| WO | WO 2014/085216 | 5/2014 |
| WO | WO 2014/089913 | 6/2014 |
| WO | WO 2014/105849 | 7/2014 |
| WO | WO 2014/113191 | 7/2014 |
| WO | WO 2014/136972 | 9/2014 |
| WO | WO 2014/138485 | 9/2014 |
| WO | WO 2014/140184 | 9/2014 |
| WO | WO 2014/144737 | 9/2014 |
| WO | WO 2014/160160 | 10/2014 |
| WO | WO 2014/160478 | 10/2014 |
| WO | WO 2014/160521 | 10/2014 |
| WO | WO 2014/162039 | 10/2014 |
| WO | WO 2014/170063 | 10/2014 |
| WO | WO 2014/171755 | 10/2014 |
| WO | WO 2014/172644 | 10/2014 |
| WO | WO 2014/174307 | 10/2014 |
| WO | WO 2014/182829 | 11/2014 |
| WO | WO 2014/198942 | 12/2014 |
| WO | WO 2014/206343 | 12/2014 |
| WO | WO 2014/206344 | 12/2014 |
| WO | WO 2015/000715 | 1/2015 |
| WO | WO 2015/006492 | 1/2015 |
| WO | WO 2015/006754 | 1/2015 |
| WO | WO 2015/030021 | 3/2015 |
| WO | WO 2015/057938 | 4/2015 |
| WO | WO 2015/057963 | 4/2015 |
| WO | WO 2015/059668 | 4/2015 |
| WO | WO 2015/061572 | 4/2015 |
| WO | WO 2015/066452 | 5/2015 |
| WO | WO 2015/095492 | 6/2015 |
| WO | WO 2015/108992 | 7/2015 |
| WO | WO 2016/064960 | 4/2016 |
| WO | WO 2016/134314 | 8/2016 |
| WO | WO 2016/192680 | 12/2016 |
| WO | WO 2017/028314 | 2/2017 |
| WO | WO 2017/223414 | 12/2017 |
| WO | WO 2018/041091 | 3/2018 |
| WO | WO 2018/049214 | 3/2018 |
| WO | WO 2018/067512 | 4/2018 |
| WO | WO 2018/093029 | 5/2018 |
| WO | WO 2018/093215 | 5/2018 |
| WO | WO 2018/105972 | 6/2018 |
| WO | WO 2018/105973 | 6/2018 |
| WO | WO 2018/234354 | 12/2018 |
| WO | WO 2019/037640 | 2/2019 |
| WO | WO 2019/079369 | 4/2019 |
| WO | WO 2019/105886 | 6/2019 |
| WO | WO 2019/213506 | 11/2019 |
| WO | WO 2020/049017 | 3/2020 |
| WO | WO 2020/081898 | 4/2020 |
| WO | WO 2020/131627 | 6/2020 |
| WO | WO 2020/131674 | 6/2020 |
| WO | WO 2021/113462 | 6/2021 |

OTHER PUBLICATIONS

Chinese Office Action in Chinese Application No. 201980042917.9, dated Jan. 18, 2023, 14 pages (with English translation).
Ecuador Office Action in Ecuador Application No. IEPI-2015-1225, dated Jan. 9, 2023, 30 pages (with English translation).
Indian Office Action in Indian Application No. 201917050123, dated Mar. 29, 2023, 5 pages.
Jain et al., "Cholangiocarcinoma With FGFR Genetic Aberrations: A Unique Clinical Phenotype," JCO Precision Oncology, Jan. 17, 2018, 2:1-12.
Japanese Office Action in Japanese Application No. 2020-561731, dated Mar. 22, 2023, 8 pages (with English translation).
Japanese Office Action in Japanese Application No. 2020-561741, dated Mar. 22, 2023, 11 pages (with English translation).

(56) References Cited

OTHER PUBLICATIONS

Mexican Office Action in Mexican Application No. MX/a/2020/011718, dated Apr. 4, 2023, 12 pages (with machine translation).
Summons to attend oral proceedings pursuant to Rule 115(1) EPC in European Application No. 19724676.2, dated Feb. 22, 2023, 5 pages.
Taiwanese Office Action in Taiwanese Application No. 108115462, dated Jan. 10, 2023, 12 pages (with English translation).
Taiwanese Office Action in Taiwanese Application No. 108115470, dated Mar. 21, 2023, 13 pages (with machine translation).
Taiwanese Office Action in Taiwanese Application No. 110132234, dated Nov. 25, 2022, 5 pages.
"Sabiosciences.com" [online]. "FGF Pathway," 2000-2012, [retrieved on Jun. 23, 2015]. Retrieved from the Internet: URL <http://www.sabiosciences.com/pathway.php?sn=FGF_Signaling>, 3 pages.
"Substance Record for SID 240993001," Feb. 13, 2015, pp. 1-8.
Acevedo et al., "Inducible FGFR-1 Activation Leads to Irreversible Prostate Adenocarcinoma and an Epithelial-to-Mesenchymal Transition," Cancer Cell, Dec. 2007, 12: 559-571.
Adib et al., "FGFR2/3 genomic alterations and response to Enfortumab Vedotin in metastatic urothelial carcinoma," BJUI Compass., 2022, 3:169-172.
Alexander et al., "Systemtherapie des Harnblasenkarzinoms," Der Urologe, Jan. 4, 2021, 60(2):247-258 (English Abstract).
Ali et al., "Synthesis and structure activity relationship of substituted N,6-diphenyl-5,6-dihydrobenzo[h]quinazolin-2-amine as inhibitors of fibroblast growth factor receptors (FGFR)" Cancer Res, Apr. 15, 2012, 72; 3905.
Angevin et al., "TKI258 (dovitinib lactate) in metastatic renal cell carcinoma (mRCC) patients refractory to approved targeted therapies: A phase I/II dose finding and biomarker study," Journal of Clinical Oncology, May 20, 2009, 27:15S, 1 page.
Anonymous, "American Society for Clinical Pharmacology and Therapeutics," Clin Pharma and Thera., Feb. 13, 2019, 105(S1):S5-S121.
Anonymous, "In Vitro Metabolism- and Transporter-Mediated Drug-Drug Interaction Studies Guidance for Industry", Clinical Pharmacology, Oct. 2017, 47 pages.
Antonios-Mccrea et al., "LHMDS mediated tandem acylation-cyclization of 2-aminobenzenecarbonitriles with 2-benzymidazol-2-ylacetates: a short and efficient route to the synthesis of 4-amino-3-benzimidazol-2-ylhydroquinolin-2-ones," Tetrahedron Letters, 2006, 657-660.
Arai et al., "Characterization of the cell or origin and propagation potential of the fibroblast growth factor 9-induced mouse model of lung adenocarcinoma," J. Pathol., Mar. 2015, 235(4): 593-605.
Arai et al., "Fibroblast growth factor receptor 2 tyrosine kinase fusions define a unique molecular subtype of cholangiocarcinoma," Hepatology, 2014, 59(4):1427-1434.
Argentina Office Action in Argentina Application No. 20130102068, dated Jul. 17, 2020, 10 pages.
Argentina Office Action in Argentina Application No. 20140101651, dated Jul. 29, 2021, 9 pages.
Argentina Office Action in Argentina Application No. 20140101651, dated Nov. 21, 2019, 5 pages.
Ash and Ash, "Handbook of Pharmaceutical Additives," Gower Publishing Company, 2007, 3rd ed.
Atzrodt et al., "The Renaissance of H/D Exchange," Angew Chem Int Ed., 2007, 7744-7765.
Australian Office Action in Australian Application No. 2013287176, dated Sep. 12, 2017, 4 pages.
Australian Office Action in Australian Application No. 2014253798, dated Jul. 31, 2017, 4 pages.
Australian Office Action in Australian Application No. 2016219816, dated Aug. 26, 2019, 3 pages.
Australian Office Action in Australian Application No. 2016219822, dated Jul. 8, 2019, 4 pages.
Australian Office Action in Australian Application No. 2018208772, dated Jul. 1, 2018, 5 pages.
Australian Office Action in Australian Application No. 2018272013, dated Sep. 2, 2021, 4 pages.
Australian Office Action in Australian Application No. 2019200066, dated Aug. 27, 2019, 6 pages.
Australian Office Action in Australian Application No. 2020250211, dated Sep. 13, 2021, 4 pages.
Australian Office Action in Australian Application No. 2020270520, dated Dec. 16, 2021, 4 pages.
Avet-Loiseau et al., "Impact of high-risk cytogenetics and prior therapy on outcomes in patients with advanced relapsed or refractory multiple myeloma treated with lenalidomide plus dexamethasone," Leukemia, 2010, 623-628.
Bai et al., "GP369, an FGFR2-IIIb specific antibody, exhibits potent antitumor activity against human cancers driven by activated FGFR2 signaling," Am. Assoc. for Cancer Research, Aug. 17, 2010, 30 pages.
Bansal et al., "Specific inhibitor of FGF receptor signaling: FGF-2-mediated effects on proliferation, differentiation, and MAPK activation are inhibited by PD173074 in oligodendrocyte-lineage cells," J. Neurosci. Res., 2003, 74: 486.
Bavin, "Polymorphism in Process Development," Chemistry & Industry, Society of Chemical Industry, Aug. 1989, 527-529.
Bazyl et al., "The selective ortho-methoxylation of pentafluorobenzoic acid—a new way to tetrafluorosalicylic acid and its derivatives," J Flour Chem., Feb. 11, 1999, 94(1):11-13.
Beekman et al., "New Molecular Targets and Novel Agents in the Treatment of Advanced Urothelial Cancer," Semin Oncol, 2007, 34: 154-164.
Bello et al., "E-3810 is a potent dual inhibitor of VEGFR and FGFR that exerts antitumor activity in multiple preclinical models," Cancer Res, 2011.
Bello et al., "E-3810 is a potent dual inhibitor of VEGFR and FGFR that exerts antitumor activity in multiple preclinical models," Cancer Res, 2011, Supplemental figures, 4 pages.
Bello et al., "E-3810 is a potent dual inhibitor of VEGFR and FGFR that exerts antitumor activity in multiple preclinical models," Cancer Res, 2011, Supplemental table, 3 pages.
Bello et al., "E-3810 is a potent dual inhibitor of VEGFR and FGFR that exerts antitumor activity in multiple preclinical models," Cancer Res, 2011, Supplementary data, 4 pages.
Benet-Pages et al., "An FGF23 missense mutation causes familial tumoral calcinosis with hyperphosphatemia," Human Molecular Genetics, 2005, 14(3):385-390.
Berge et al., "Pharmaceutical Salts", Journal of Pharmaceutical Science, 1977, 66(2):1-19.
Bergwitz and Juppner, "Regulation of Phosphate Homeostasis by PTH, Vitamin D, and FGF23," Annu. Rev. Med., 2010, 61:91-104.
Bhide et al., "Discovery and Preclinical Studies of (R )-1-(4-(4-Fluoro-2-methyl-1H-indol-5-yloxy)-5-methylpyrrolo[2,1-f][1,2,4]triazin-6-yloxy)propan-2-ol (BMS-540215), an In Vivo Active Potent VEGFR-2 Inhibitor," Journal of Medicinal Chemistry, 2006, 49(7): 2143-2146.
Billerey et al., "Frequent FGFR3 Mutations in Papillary Non-Invasive Bladder (pTa) Tumors," American Journal of Pathology, Jun. 2001, 158(6): 1955-1959.
Billottet et al., "Targets of Fibroblast Growth Factor 1 (FGF-1) and FGF-2 Signaling Involved in the Invasive and Tumorigenic Behavior of Carchinoma Cells," Molecular Biology of the Cell, Oct. 2004, 15: 4725-4734.
Biocentury, Week of Nov. 10, 2014, 52 pages.
Bisping et al., "Bortezomib, Dexamethasone, and Fibroblast Growth Factor Receptor 3-Specific Tyrosine Kinase Inhibitor in t(4;14) Myeloma," Clin Cancer Res, Jan. 2009, 15(2):520-531.
Black et al., "Targeted therapies in bladder cancer—an update," Urologic Oncology: Seminars and Original Investigations, 2007, 433-438.
Blom et al., "Optimizing Preparative LC-MS Configurations and Methods for Parallel Synthesis Purification", J Combi Chem., 2003, 5:670.
Blom et al., Preparative LC-MS Purification: Improved Compound Specific Method Optimization, J Combi Chem. 2004, 6(6):874-883.
Blom, K., "Two-Pump At Column Dilution Configuration for Preparative LC-MS", J Combi Chem., 2002, 4:295.

(56) References Cited

OTHER PUBLICATIONS

Bonaventure et al., "Common Mutations in the Fibroblast Growth Factor Receptor 3 (FRFR3) Gene Account for Achondroplasia, Hypochondroplasia and Thanatophoric Dwarfism," Clin Pediatr Endocrinol, 1997, 105-113.
Bono et al., "Inhibition of Tumor Angiogenesis and Growth by a Small-Molecule Multi-FGF Receptor Blocker with Allosteric Properties," Cancer Cell, Apr. 2013, 477-488.
Borad et al., "Fibroblast growth factor receptor 2 fusions as a target for treating cholangiocarcinoma," Current opinion in Gastroenterology, May 2015, 31(3):264-268.
Brooks et al., "Fibroblast growth factor signaling: a new therapeutic opportunity in cancer," Clinical Cancer Research, 2012, 1-23.
Caira, "Crystalline Polymorphism of Organic Compounds,"Topics in Current Chemistry, Jan. 1, 1998, 198:163-208.
Cancer [online], [retrieved on Jul. 6, 2007] Retrieved from the Internet, URL: http://www.nlm.nih.gov/medlineplus/cancer.html.
Capelletti et al., "Identification of Recurrent FGFR3-TACC3 Fusion Oncogenes from Lung Adenocarcinoma," AACR Journals, 2014, 6551-6558.
Cappellen et al., "Frequent activating mutations of FGFR3 in human bladder and cervix carcinomas," Nature Genetics, Sep. 1999, 23: 18-20.
Carmichael et al., "Familial Tumoral Calcinosis: A Forty-Year Follow-up on One Family," The Journal of Bone & Joint Surgery, 2009, 664-671.
Casey et al., "Translating in vivo metabolomic analysis of succinate dehydrogenase deficient tumours into clinical utility," JCO Precis Oncol., Mar. 29, 2018, 2:1-12.
Cha et al., "Aberrant Receptor Internalization and Enhanced FRS2-dependent Signaling Contribute to the Transforming Activity of the Fibroblast Growth Factor Receptor 2 IIIb C3 Isoform," The Journal of Biological Chemistry, Mar. 2009, 284(10): 6227-6240.
Chandrani et al., "Drug-sensitive FGFR3 mutations in lung adenocarcinoma," Annals of Oncology, 2017, 28: 597-603.
Chase et al., "Activity of TKI258 against primary cells and cell lines with FGFR1 fusion genes associated with the 8p11 myeloproliferative syndryome," Blood, 2007, 110:3729-3734.
Chefetz and Sprecher, "Familial tumoral calcinosis and the role of O-glycosylation in the maintenance of phosphate homeostasis," Biochimica et Biophysica Acta, 2009, 847-852.
Chefetz et al., "A novel homozygous missense mutation in FGF23 causes Familial Tumoral Calcinosis associated with disseminated visceral calcification," Hum Genet, 2005, 118:261-266.
Chell et al., "Tumour cell responses to new fibroblast growth factor receptor tyrosine kinase inhibitors and identification of a gatekeeper mutation in FGFR3 as a mechanism of acquired resistance," Oncogene, 2012, 1-12.
Chen et al., "Acenaphtho[1,2-b]pyrrole-Based Selective Fibroblast Growth Factor Receptors 1 (FRGR1) Inhibitors: Design, Synthesis, and Biological Activity," Jounal of Medicinal Chemistry, 2011, 54: 3732-3745.
Chen et al., "FGFR3 as a therapeutic target of the small molecule inhibitor PKC412 in hematopoietic malignancies," Oncogene, 2005, 24: 8259-8267.
Chen et al., "Genome-Wide Loss of Heterozygosity and DNA Copy Number Aberration in HPV-Negative Oral Squamous Cell Carcinoma and Their Associations with Disease-Specific Survival," PLOS One, Aug. 2015, 23 pages.
Cherukupalli et al., "An insight on synthetic and medicinal aspects of pyrazolo[1,5-a]pyrimidine scaffold," European Journal of Medicinal Chemistry, Nov. 10, 2016, 126:298-352.
Chesi et al., "Activated fibroblast growth factor receptor 3 is an oncogene that contributes to tumor progression in multiple myeloma," Blood, 2001, 97:729-736.
Chesi et al., "Frequent translocation t(4;14)(p16.3;q32.3) in multiple myeloma is associated with increased expression and activating mutations of fibroblast growth factor receptor 3," Nature Genetics, 1997, 260-264.

Chilean Office Action in Chilean Application No. 1984-2017, dated Sep. 12, 2019, 9 pages.
Chilean Office Action in Chilean Application No. 2015-003089, dated Apr. 24, 2017, 13 pages (English Summary).
Chilean Office Action in Chilean Application No. 2015-003089, dated Jan. 23, 2018, 8 pages.
Chilean Office Action in Chilean Application No. 2122-2017, dated Apr. 22, 2019, 25 pages.
Chilean Office Action in Chilean Application No. 2122-2017, dated Nov. 15, 2019, 15 pages.
Chilean Office Action in Chilean Application No. 3355-2014, dated Jan. 18, 2017, 17 pages (with English translation).
Chilean Office Action in Chilean Application No. 3439-2019, dated Feb. 10, 2021, 26 pages.
Chilean Opposition in Chilean Application No. 3355-2014, received Feb. 3, 2017, 3 pages (English translation only).
Chinese Office Action in Chinese Application No. 10874686.0, dated Oct. 8, 2019, 10 pages.
Chinese Office Action in Chinese Application No. 201380041027.9, dated Feb. 13, 2017, 10 pages (with English translation).
Chinese Office Action in Chinese Application No. 201380041027.9, dated Jul. 12, 2016, 11 pages (with English translation).
Chinese Office Action in Chinese Application No. 201380041027.9, dated Oct. 28, 2015, 17 pages (with English translation).
Chinese Office Action in Chinese Application No. 201480028858.7, dated Apr. 4, 2018, 10 pages (English Translation).
Chinese Office Action in Chinese Application No. 201480028858.7, dated Aug. 19, 2016, 18 pages (English Translation).
Chinese Office Action in Chinese Application No. 201480028858.7, dated Jul. 12, 2017, 10 pages (English Translation).
Chinese Office Action in Chinese Application No. 201680011332.7, dated Aug. 5, 2019, 14 pages.
Chinese Office Action in Chinese Application No. 201680011348.8, dated Aug. 2, 2019, 14 pages.
Chinese Office Action in Chinese Application No. 201710395346.X, dated Jan. 22, 2019, 17 pages.
Chinese Office Action in Chinese Application No. 201710395346.X, dated Sep. 9, 2019, 10 pages.
Chinese Office Action in Chinese Application No. 201710874686.0, dated Feb. 25, 2019, 17 pages.
Chinese Office Action in Chinese Application No. 201910023729.3, dated Sep. 8, 2021, 11 pages.
Chinese Office Action in Chinese Application No. 201910023729.3, dated Mar. 3, 2021, 15 pages.
Chng et al., "Translocation t(4;14) retains prognostic significance even in the setting of high-risk molecular signature," Leukemia, 2008, 2: 459-461.
Chuaqui et al., "Interaction Profiles of Protein Kinase—Inhibitor Complexes and Their Application to Virtual Screening," J. Med. Chem., 2005, 48: 121-133.
Ciappetti and Geithlen "Molecular Variations Based on Isosteric Replacements," The Practice of Medicinal Chemistry, 2008, Chapter 15, pp. 290-341.
ClinicalTrials.gov, "A Study to Evaluate the Efficacy and Safety of Pemigatinib Versus Cherrotherapy in Unresectable or Metastatic Chol (FIGHT-302)," NCT03656536, Mar. 6, 2019, retrieved from URL <https://www.clinicaltrials.gov/ct2/history/NCT03656536?V_5=View#StudyPageTop,>, 4 pages.
Cole et al., "Inhibition of FGFR2 and FGFRI increases cisplatin sensitivity in ovarian cancer," Cancer Biol. Therapy, Sep. 1, 2010, 10(5):495-504.
Coleman, "Positive and negative regulation of cellular sensitivity to anti-cancer drugs by FGF-2," Drug Resistance Updates, 2003, 85-94.
Colombian Office Action in Colombian Application No. 14-275934-6, dated May 31, 2016, 3 pages (English translation only).
Colombian Office Action in Colombian Application No. 14-275934-6, dated Nov. 17, 2015, 12 pages (English translation only).
Colombian Office Action in Colombian Application No. 16100866, dated Aug. 10, 2017, 9 pages.
Colombian Office Action in Colombian Application No. NC2017/0008795, dated Nov. 29, 2018, 8 pages.

(56) References Cited

OTHER PUBLICATIONS

Colombian Office Action in Colombian Application No. NC2017/0008795, dated Aug. 16, 2019, 6 pages.
Colombian Office Action in Colombian Application No. NC2017/0008795, dated Aug. 29, 2017, 2 pages.
Colombian Office Action in Colombian Application No. NC2017/0008824, dated Aug. 31, 2017, 3 pages.
Colombian Office Action in Colombian Application No. NC2017/0008824, dated Nov. 29, 2018, 8 pages.
Colombian Office Action in Colombian Application No. NC2019/0009690, dated Jan. 22, 2020, 20 pages.
Colombian Office Action in Colombian Application No. NC2019/0014699, dated Oct. 31, 2022, 31 pages.
Colombian Opposition in Colombian Application No. NC 2021/0004568, dated Apr. 15, 2021, 21 pages.
Cordovilla et al., "The Stille Reaction, 38 Years Later," ACS Catal., Apr. 17, 2015, 5(5):3040-3053.
Corre et al., "Synthesis and biological evaluation of a triazole-based library of pyrido[2,3-d]pyrimidines as FGFR3 tyrosine kinase inhibitors," Organic & Biomolecular Chemistry, 2010, 8:2164-2173.
Costa Rican Office Action in Costa Rican Application No. 2014-0577, dated Apr. 15, 2020, 18 pages.
Costa Rican Office Action in Costa Rican Application No. 2014-0577, dated Jun. 13, 2019, 17 pages.
Costa Rican Office Action in Costa Rican Application No. 2015-0578, dated Jun. 11, 2020, 15 pages.
Costa Rican Opposition in Costa Rican Application No. PCT/US2013/045309, dated Jun. 29, 2015, 14 pages (English Translation).
Covic et al., "Vascular calcification in chronic kidney disease," Clinical Science, 2010, 119: 111-121.
Crose et al., "FGFR4 Blockade Exerts Distinct Antitumorigenic Effects in Human Embryonal versus Alveolar Rhabdomyosarcoma," Clin Cancer Res., 2012, 18:3780-3790.
Dailey et al., "Mechanisms underlying differential responses to FGF signaling," Cytokine & Growth Factor Reviews, 2005, 233-247.
Dash et al., "A Role for Neoadjuvant Gemcitabine Plus Cisplatin in Muscle-Invasive Urothelial Carcinoma o the Bladder: A Retrospective Experience," Cancer, 2008, 113(9): 2471-2477.
De Luca et al., "FGFR Fusions in Cancer: From Diagnostic Approaches to Therapeutic Intervention," Int J Mol Sci., 2020, 21(8):6856.
Desnoyers et al., "Targeting FGF19 inhibits tumor growth in colon cancer xenograft and FGF19 transgenic hepatocellular carcinoma models," Oncogene, 2008, 27:85-97.
Dey et al., "Targeting Fibroblast Growth Factor Receptors Blocks PI3K/AKT Signaling, Induces Apoptosis, and Impairs Mammary Tumor Outgrowth and Metastasis," Cancer Research, 2010, 4151-4162.
Dieci et al., "Fibroblast Growth Factor Receptor Inhibitors as a Cancer Treatment: From a Biologic Rationale to Medical Perspectives," Cancer Discovery, 2013, 1-16.
Dienstmann et al., "Genomic aberrations in the FGFR pathway: opportunities for targeted therapies in solid tumors," Annals of Oncology, 2013, 1-12.
Diller and Li, "Kinases, Homology Models, and High Throughput Docking," J. Med. Chem., 2003, 46: 4638-4647.
Dimopoulos et al., "Lenalidomide plus Dexamethasone for Relapsed or Refractory Multiple Myeloma," The New England Journal of Medicine, 2007, 357:2123-2132.
Ding et al., "Somatic mutations affect key pathways in lung adenocarcinoma," Nature., Oct. 23, 2008, 455:1069-1075.
Dovedi and Davies, "Emerging targeted therapies for bladder cancer: a disease waiting for a drug," Cancer Metastasis Rev, 2009, 28:355-367.
Dring et al., "A Global Expression-based Analysis of the Consequences of the t(4;14) Translocation in Myeloma," Clinical Cancer Research, Sep. 2004, 10: 5692-5701.
Drueke et al., "Phosphate binders in CKD: bad news or good news?," Journal of the American Society of Nephrology, Aug. 2012, 23(8):1277-1280.
Dutt et al., "Drug-sensitive FGFR2 mutations in endometrial carcinoma," PNAS, Jun. 24, 2008, 105(25):8713-8717.
Dutt et al., "Drug-sensitive FGFR2 mutations in endometrial carcinoma," Supporting Information, Jun. 2008, 8 pages.
Ecuador Office Action in Ecuador Application No. IEPI-2015-1225, dated Dec. 30, 2021, 21 pages.
Edmondson et al., "Aminopiperidine-fused imidazoles as dipeptidyl peptidase-IV inhibitors," Bioorg & Med Chem Lett., 2009, 19(15):4097-4101.
Eissa, "Synthesis and evaluation of some surface active agents from long chain fatty amine," Spanish National Research Council, Jan. 2007, 58(4):379-389.
Elsheikh et al., "FGFR1 amplification in breast carcinomas: a chromogenic in situ hybridisation analysis," Breast Cancer Research, Mar. 2007, 9(2): 1-12.
Erian at al., "2-Aryl-1,1-dicyano-3-phenylsulfonylpropenes in heterocyclic synthesis. A synthetic strategy towards heterocyclic sulfones," Monatshefte fuer Chemie, 1998, 129(10):1049-1056.
Eskens and Verweij, "The clinical toxicity profile of vascular endothelial growth factor (VEGF) and vascular endothelial growth factor receptor (VEGFR) targeting angiogenesis inhibitors; A review," European Journal of Cancer, 2006, 3127-3139.
Eswarakumar and Schlessinger, "Cellular signaling by fibroblast growth factor receptors," Cytokine & Growth Factor Reviews, 2005, 139-149.
Eurasian Office Action in Eurasian Application No. 201590005, dated Oct. 21, 2015, 6 pages.
Eurasian Office Action in Eurasian Application No. 201590005, Mar. 28, 2018, 6 pages.
Eurasian Office Action in Eurasian Application No. 201791866, dated Feb. 19, 2018, 10 pages (English Translation).
Eurasian Office Action in Eurasian Application No. 201791867, dated Apr. 4, 2018, 4 pages (English Translation).
Eurasian Office Action in Eurasian Application No. 201992794, dated Sep. 17, 2021, 7 pages.
Eurasian Office Action in Eurasian Application No. 202091923, dated Jul. 27, 2021, 6 pages (English Translation).
Eurasian Office Action in Eurasian Application No. 202092648, dated Feb. 8, 2022, 7 pages.
Eurasian Office Action in Eurasian Application No. 202190877, dated Oct. 6, 2021, 4 pages.
European Communication pursuant to Article 94(3) EPC in European Application No. 13783125.1, dated Jan. 26, 2016, 4 pages.
European Office Action in European Application No. 16715139.8, dated May 18, 2021, 9 pages.
European Office Action in European Application No. 18733045.1, dated Jan. 11, 2021, 5 pages.
European Office Action in European Application No. 19724670, dated Aug. 31, 2022, 3 pages.
European Office Action in European Application No. 19724670.5, dated Nov. 9, 2021, 4 pages.
European Office Action in European Application No. 19724676.2, dated Aug. 26, 2021, 5 pages.
European Office Action in European Application No. 20192679.7, dated Feb. 11, 2021, 7 pages.
European search report in European Application No. 16203866.5, dated Mar. 1, 2017, 7 pages.
European Search Report in European Application No. 17199421.3, dated Jul. 12, 2018, 15 pages.
European Search Report in European Application No. 17199421.3, dated Mar. 12, 2018, 14 pages.
Ezzat et al., "Dual Inhibition of RET and FGFR4 Restrains Medullary Thyroid Cancer Cell Growth," Clinical Cancer Research, 2005, 11:1336-1341.
Faul et al., "FGF23 induces left ventricular hypertrophy," The Journal of Clinical Investigation, 2010, 1-16.
FDA.gov, "FDA grants accelerated approval to pemigatinib for cholangiocarcinoma with an FGFR2 rearrangement or fusion," Apr. 20, 2020, [Retrieved on Apr. 27, 2021], retrieved from URL <https://www.fda.gov/drugs/resources-information-approved-drugs/fda-grants-accelerated-approval-pemigatinib-cholangiocarcinoma-fgfr2-rearrangement-or-fusion>, 2 pages.

(56) References Cited

OTHER PUBLICATIONS

Feng et al., "Guidance to rational use of pharmaceuticals in gallbladder sarcomatoid carcinoma using patient-derived cancer cells and whole exome sequencing," Oncotarget, 2017, 8(3): 5349-5360.
Feng et al., "Targeting Fibroblast Growth Factor Receptor Signaling Inhibits Prostate Cancer Progression," Clinical Cancer Research, 2012, 1-9.
Ferrera et al., "Bevacizumab (Avastin), a humanized anti-VEGF monoclonal antibody for cancer therapy," Biochemical and Biophysical Research Communications, 2005, 328-335.
Fillmore et al., "Estrogen expands breast cancer stem-like cells through paracrine FGF/Tbx3 signaling," PNAS, 2010, 1-6.
Fischer et al., "Fibroblast growth factor receptor-mediated signals contribute to the malignant phenotype of non-small cell lung cancer cells: therapeutic implications and synergism with epidermal growth factor receptor inhibition," Mol Cancer Therapy, 2008, 3408-3419.
French et al., Targeting FGFR4 inhibits hepatocellular carcinoma in preclinical mouse models, PLoS One 2012;7:e36713.
Fricker, "Metal based drugs: from serendipity to design," Dalton Transactions, 2007, 43:4903-4917.
Fricker, "The therapeutic application of lanthanides," Chemical Society Reviews, 2006, 35(6):524-533.
Frishberg et al., "Hypertosis-Hyperphosphatemia Syndrome: A Congenital Disorder of O-Glycosylation Associated With Augmented Processing of Fibroblast Growth Factor 23," Journal of Bone and Mineral Research, 2007, 22(2): 235-242.
Frishberg et al., "Identification of a recurrent mutation in GALNT3 demonstrates that hyperostosis-hyperphosphatemia syndrome and familial tumoral calcinosis are allelic disorders," J Mol Med, 2005, 83:33-38.
Fu et al., "Intratumoral inorganic phosphate deprivation: A new anticancer strategy," Medical Hypotheses, Feb. 2020, 135:109497.
Fukumoto and Yamashita, "FGF23 is a hormone-regulating phophate metabolism—Unique biological characteristics of FGF23," Bone, 2007, 1190-1195.
Fun et al., "2-7(7,8-Diphenyl-1H-imidazo[4,5-f]-quinoxalin-2-yl)phenol methanol disolvate," Acta Crystallographica Section E Structure Reports Online, 2008, 64(9):01741-01742.
Furniss "Acidic/Basic characteristics for purification," Vogel's Textbook of Practical Organic Chemistry, 5th edition, 1989, 131-133, 135-143.
Galdemard et al., "Regulation of FGF-3 Gene Expression in Tumorigenic and Non-tumorigenic Clones of a Human Colon Carcinoma Cell Line," The Journal of Biological Chemistry, 2000, 275(23): 17364-17373.
Gallo et al., "Functions of Fibroblast Growth Factor Receptors in cancer defined by novel translocations and mutations," Cytokine & Growth Factor Reviews, 2015, 26(4):425-449.
Garringer et al., "Molecular genetic and biochemical analyses of FGF23 mutations in familial tumoral calcinosis," Am J Physiol Endocrinol Metab, 2008, 929-937.
Gattineni et al., "FGF23 decreases renal NaPi-2a and NaPi-2c expression and induces hypophosphatemia in vivo predominantly via FGF receptor 1," Am J Physiol Renal Physiol, 2009, 297: 282-291.
Gavine et al., "AZD4547: An Orally Bioavailable, Potent, and Selective Inhibitor of the Fibroblast Growth Factor Receptor Tyrosine Kinase Family," American Association for Cancer Research, Apr. 2012, 72(8): 2045-2056.
Gennaro et al., "Pharmaceutical Sciences," Remington's Pharmaceutical Sciences 17th Ed., Jan. 1985, 14-18 and 1409-1423.
Gerby et al., "2-Arylidenedihydroindole-3-ones: Design, synthesis, and biological activity on bladder carcinoma cell lines," Bioorganic & Medicinal Chemistry Letters, 2007, 208-213.
Ghorab et al., "Synthesis of some sulfur containing Tetrahydrobenzoabuthieno[b] Thieno(Pyridines, Quinolines, Oxazines and Pyrimidines) as possible radioprotective and Antineoplastic agents," Phosphorus, Sulfur and Silicon, Jan. 1998, 134/135:57-76.
Gibson, "Pharmaceutical Preformulation and Formulation," CRC Press LLC, 2009, 2nd ed, 559 pages.

Goetz et al., "Isolated C-terminal tail of FGF23 alleviates hypophosphatemia by inhibiting FGF23-FGFR-Klotho complex formation," PNAS, Jan. 2010, 107(1): 407-412.
Golub et al., "Molecular Classification of Cancer: Class Discovery and Class Prediction by Gene Expression Monitoring," Science, 1999, 286: 531-537.
Gomez-Rivera et al., "The Tyrosine Kinase Inhibitor, AZD2171, Inhibits Vascular Endothelial Growth Factor Receptor Signaling and Growth of Anaplastic Thyroid Cancer in an Orthotopic Nude Mouse Model," Clin Cancer Res, Aug. 2007, 4519-4527.
Govindan, "Summary of Presentations from the Ninth Annual Targeted Therapies in Lung Cancer Symposium," Journal of Thoracic Oncology, Nov. 2009, 4(11): 1045-1089.
Goyal et al,. "Polyclonal Secondary FGFR2 Mutations Drive Acquired Resistance to FGFR Inhibition in Patients with FGFR2 Fusion-Positive Cholangiocarcinoma," Cancer Discov., 2016, 7(3):252-263.
Gozgit et al., "Ponatinib (AP24534), a Multitargeted Pan-FGFR Inhibitor with Activity in Multiple FGFR-Amplified or Mutated Cancer Models," Mol Cancer Ther, 2012, 11: 690-699.
Granberg et al., "Strong FGFR3 staining is a marker for FGFR3 fusions in diffuse gliomas," Neuro-Oncology, 2017, 19(9): 1206-1216.
Grand et al., "Targeting FGFR3 in multiple myeloma: inhibition of t(4;14)-positive cells by SU5402 and PD173074," Leukemia, 2004, 18: 962-966.
Greene, T. W. and Wuts, P. G. M., "Protective Groups in Organic Synthesis", 3rd Ed., Wiley & Sons, Inc., New York (1999), 799 pages.
Greulich and Pollock, "Targeting mutant fibroblast growth factor receptors in cancer," Cell Press, May 2011, 17(5): 283-292.
Grose and Dickson, "Fibroblast growth factor signaling in tumorigenesis," Cytokine & Growth Factor Reviews, 2005, 179-186.
Gu et al., "Phosphotyrosine profiling identifies the KG-1 cell line as a model for the study of FGFRI fusions in acute myeloid leukemia," Blood, Dec. 15, 2006, 108(13):4202-42040.
Guagnano et al., "Discovery of 3-(2,6-Dichloro-3,5-dimethoxyphenyl)-1-{6-[4-(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase," J. Med. Chem., 2011, 54: 7066-7083.
Guan et al., "Design and synthesis of aminopropyl tetrahydroindole-based indolin-2-ones as selective and potent inhibitors of Src and Yes tyrosine kinase," Bioorganic & Medicinal Chemistry Letters, 2004, 187-190.
Gust et al., "Fibroblast Growth Factor Receptor 3 Is a Rational Therapeutic Target in Bladder Cancer," Molecular Cancer Therapeutics, Jul. 2013, 12(7): 1245-1254.
Haas et al., "Recent Developments in Negishi Cross-Coupling Reactions," ACS Catal., 2016, 6(3):1540-1552.
Hackam et al. "Translation of Research Evidence From Animals to Humans," JAMA, 296(14), 2006, 296(14):1731-1732.
Hafner et al., "High Frequency of FGFR3 Mutations in Adenoid Seborrheic Keratoses," Journal of Investigative Dermatology, 2006, 126: 2404-2407.
Hafner, "Seborrheic keratoses and epidermal nevi: new pathogenetic insights and therapeutic implications," Expert Rev Dermatol, 2006, 1(6): 759-761.
Hagel et al., "First Selective Small Molecule Inhibitor of FGFR4 for the Treatment of Hepatocellular Carcinomas with an Activated FGFR4 Signaling Pathway," Cancer Discovery, Apr. 1-14, 2015.
Hara and Saito, "CARD9 versus CARMA1 in innate and adaptive immunity," Cell Press, 2009, 234-242.
Heinrich et al., "Fragment-based discovery of new highly substituted 1H-pyrrolo[2,3-b]- and 3H-imidazolo[4,5-b]-pyridines as focal adhesion kinase inhibitors," J of Med Chem., Jan. 8, 2013, 56(3):1160-1170.
Heinzle C, et al., "Differential Effects of Polymorphic Alleles of FGF Receptor 4 on Colon Cancer Growth and Metastasis," Cancer Research, Nov. 2012, 72(22):5767-5777.
Heinzle et al., "Is fibroblast growth factor receptor 4 a suitable target of cancer therapy?," Cur. Pharm. Des., 2014, 20:2881-2898.

(56) References Cited

OTHER PUBLICATIONS

Heinzle et al., "Targeting fibroblast-growth-factor-receptor-dependent signaling for cancer therapy," Expert Opinion, 2011, 1-18.
Helsten et al., "The FGFR Landscape in Cancer: Analysis of 4,853 Tumors by Next-Generation Sequencing," Clin. Cancer Res., Jan. 2016, 22:259-267.
Hess et al., "Abstract P245: Synergistic effect of combination of pemigatinib with enfortumab vedotin (EV) in human bladder cancer models," Molecular Cancer Therapeutics, Oct. 1, 2021, 20(12 Supplement):P245.
Hess et al., "Synergistic effect of combination of pemigatinib with enfortumab vedotin (EV) in human bladder cancer models," Molecular Cancer Therapeutics, Presented at AACR-NCI-EORT Virtual International Conference on Molecular Targets and Cancer Therapeutics, presented Oct. 7-10, 2021, 9 pages.
Hideshima and Anderson, "Preclinical Studies of Novel Targeted Therapies," Hematol Oncol Clin N Am, 2007, 1071-1091.
Ho et al., "Fibroblast growth factor receptor 4 regulates proliferation, anti apoptosis and alpha-fetoprotein secretion during hepatocellular carcinoma progression and represents a potential target for therapeutic intervention," J Hepatol, 2009, 50:118-127.
Honigberg et al., "The Bruton tyrosine kinase inhibitor PCI-32765 blocks B-cell activation and is efficacious in models of autoimmune disease and B-cell malignancy," Supporting Information, PNAS, Jul. 20, 2010, 107:29.
Hruska et al., "The Pathogenesis of Vascular Calcification in the Chronic Kidney Disease Mineral Bone Disorder (CKD-MBD): The Links Between Bone and Vasculature," Semin Nephrol, Mar. 2009, 29(2): 156-165.
Hu and Cong, "Fibroblast growth factor 19 is correlated with an unfavorable prognosis and promotes progression by activating fibroblast growth factor receptor 4 in advanced-stage serous ovarian cancer," Oncol Rep., Aug. 20, 2015, 34(5):2683-2691.
Huynh, "Tyrosine kinase inhibitors to treat liver cancer," Expert Opinion, 2010, 13-26.
Hynes and Dey, "Potential for Targeting the Fibroblast Growth Factor Receptors in Breast Cancer," Cancer Res, 2010, 70:5199-5202.
ICH Harmonised Tripartite Guideline, "Specifications: Test Procedures and Acceptance Criteria for New Drug Substances and New Drug Products Chemical Substances," ICHTRRPHU, Oct. 6, 1999, 35 pages.
Ichikawa et al., "A homozygous missense mutation in human KLOTHO causes severe tumoral calcinosis," The Journal of Clinical Investigation, Sep. 2007, 117(9): 2684-2691.
Ichikawa et al., "A Novel GALNT3 Mutation in a Pseudoautosomal Dominant Form of Tumoral Calcinosis: Evidence That the Disorder Is Autosomal Recessive," J. Clin. Endocrinol. Metab., 2005, 90:2420-2423.
Ichikawa et al., "Clinical Variability of Familial Tumoral Calcinosis Caused by Novel GALNT3 Mutations," American Journal of Medical Genetics, 2009, 896-903.
Ichikawa et al., "Novel GALNT3 Mutations Causing Hyperostosis-Hyperphosphatemia Syndrome Result in Low Intact Fibroblast Growth Factor 23 Concentrations," J. Clin. Endocrinol. Metab., 2007, 92:1943-1947.
Ichikawa et al., "Tumoral Calcinosis Presenting with Eyelid Calcifications due to Novel Missense Mutations in the Glycosyl Transferase Domain of the GALNT3 Gene," J. Clin. Endocrinol. Metab., 2006, 91: 4472-4475.
Indian Office Action in Indian Application No. 10665/DELNP/2014, dated Jun. 25, 2018, 8 pages.
Indian Office Action in Indian Application No. 201717030265, dated Dec. 12, 2019, 5 pages.
Indian Office Action in Indian Application No. 201717030267, dated Dec. 3, 2019, 7 pages.
Indian Office Action in Indian Application No. 9781/DELNP/2015, dated Jan. 18, 2019, 6 pages.
Indian Oral Hearing in Indian Application No. 201717030265, dated Jan. 13, 2022, 2 pages.
Indonesian Office Action in Indonesian Application No. P00201507153, dated Apr. 27, 2018, 5 pages (English Translation).
Indonesian Office Action in Indonesian Application No. PID201705977, Jun. 5, 2020, 5 pages.
Inokuchi et al., "Therapeutic targeting of fibroblast growth factor receptors in gastric cancer," Gastroenterol Res Pract., Apr. 27, 2015, 2015:796380, 8 pages.
International Invitation to Pay Fees in International Appln. No. PCT/US2019/030633, dated Aug. 12, 2019, 5 pages.
International Preliminary Report on Patentability and Written Opinion in International Application No. PCT/US2011/066473, issued Jun. 25, 2013, 10 pages.
International Preliminary Report on Patentability in International Application No. PCT/US2013/045309, mailed Dec. 24, 2014, 11 pages.
International Preliminary Report on Patentability in International Application No. PCT/US2013/054361, mailed Feb. 19, 2015, 7 pages.
International Preliminary Report on Patentability in International Application No. PCT/US2014/034662, dated Oct. 29, 2015, 12 pages.
International Preliminary Report on Patentability in International Application No. PCT/US2015/056583, dated Apr. 25, 2017, 7 pages.
International Preliminary Report on Patentability in International Application No. PCT/US2016/018737, dated Aug. 31, 2017, 8 pages.
International Preliminary Report on Patentability in International Application No. PCT/US2016/018770, dated Aug. 22, 2017, 10 pages.
International Preliminary Report on Patentability in International Application No. PCT/US2016/018787, dated Aug. 22, 2017, 7 pages.
International Preliminary Report on Patentability in International Application No. PCT/US2018/034559, dated Nov. 26, 2019, 8 pages.
International Preliminary Report on Patentability in International Application No. PCT/US2019/030578, dated Nov. 10, 2020, 14 pages.
International Preliminary Report on Patentability in International Application No. PCT/US2019/030633, dated Nov. 10, 2020, 10 pages.
International Preliminary Report on Patentability in International Application No. PCT/US2020/021313, dated Aug. 25, 2021, 11 pages.
International Preliminary Report on Patentability in International Application No. PCT/US2020/041104, dated Jan. 11, 2022, 7 pages.
International Search Report and Written Opinion for International Application No. PCT/US2015/056583, dated Dec. 15, 2015, 10 pages.
International Search Report and Written Opinion in International Application No. PCT/US2020/053436, dated Dec. 4, 2020, 15 pages.
International Search Report and Written Opinion in International Application No. PCT/US2013/045309, mailed on Jan. 22, 2014, 19 pages.
International Search Report and Written Opinion in International Application No. PCT/US2013/054361, dated Oct. 16, 2013, 12 pages.
International Search Report and Written Opinion in International Application No. PCT/US2014/034662, mailed Oct. 24, 2014, 18 pages.
International Search Report and Written Opinion in International Application No. PCT/US2016/018737, dated Jun. 2, 2016, 12 pages.
International Search Report and Written Opinion in International Application No. PCT/US2016/018770, dated Jun. 2, 2016, 14 pages.
International Search Report and Written Opinion in International Application No. PCT/US2016/018787, dated Jun. 2, 2016, 12 pages.

(56) References Cited

OTHER PUBLICATIONS

International Search Report and Written Opinion in International Application No. PCT/US2018/034559, dated Mar. 8, 2019, 14 pages.
International Search Report and Written Opinion in International Application No. PCT/US2019/030578, dated Jul. 11, 2019, 26 pages.
International Search Report and Written Opinion in International Application No. PCT/US2019/030633, dated Nov. 28, 2019, 21 pages.
International Search Report and Written Opinion in International Application No. PCT/US2020/021313, dated Jun. 26, 2020, 19 pages.
International Search Report and Written Opinion in International Application No. PCT/US2020/041104, dated Sep. 4, 2020, 14 pages.
International Search Report and Written Opinion in International Application No. PCT/US2020/055547, dated Jan. 11, 2021, 13 pages.
International Search Report and Written Opinion in International Application No. PCT/US2020/055735, dated Dec. 15, 2020, 16 pages.
International Search Report and Written Opinion in International Application No. PCT/US2021/013438, dated Apr. 20, 2021, 16 pages.
International Search Report and Written Opinion in International Application No. PCT/US2022/024210, dated Jun. 28, 2022, 14 pages.
International Search Report and Written Opinion in International Application. No. PCT/US2011/066473, dated Jun. 19, 2012, 15 pages.
International Search Report and Written Opinion in International Appln. No. PCT/US2020/063038, dated Mar. 15, 2021, 16 pages.
International Search Report and Written Opinion in International Appln. No. PCT/US2020/063064, dated Feb. 12, 2021, 13 pages.
Invitation to Pay Additional Fees and, Where Applicable, Protest Fee in International Application No. PCT/US2013/045309, mailed Nov. 25, 2013, 5 pages.
Isakova et al., "Fibroblast Growth Factor 23 and Risks of Mortality and End-Stage Renal Disease in Patients With Chronic Kidney Disease," JAMA, Jun. 15, 2011, 305:23, 2432-2439.
Ishikawa et al., "Accelerated proliferation of myeloma cells by interleukin-6 cooperating with fibroblast growth factor receptor 3-mediated signals," Oncogene, 2005, 24:6328-6332.
Israeli Office Action in Israeli Application No. 236,078 dated Mar. 21, 2017, 10 pages (English Translation).
Jackson et al., "8p11 Myeloproliferative syndrome: a review," Human Pathology, Apr. 1, 2010, 41:461-476.
Jan de Beur, "Tumoral Calcinosis: A Look into the Metabolic Mirror of Phosphate Homeostasis," The Journal of Clinical Endocrinology & Metabolism, 2005, 90: 2469-2471.
Japanese Office Action in Japanese Application No. 2015-517376, dated Feb. 21, 2017, 5 pages (with English translation).
Japanese Office Action in Japanese Application No. 2016-509131, dated Feb. 20, 2018, 5 pages (English Translation).
Japanese Office Action in Japanese Application No. 2017-543981, dated Dec. 3, 2019, 4 pages.
Japanese Office Action in Japanese Application No. 2017-544021, dated Nov. 26, 2019, 6 pages.
Japanese Office Action in Japanese Application No. 2018-228352, dated Aug. 20, 2019, 6 pages.
Japanese Office Action in Japanese Application No. 2020-069604, dated Nov. 15, 2021, 7 pages.
Javidi-Sharifi et al., "Crosstalk between KIT and FGFR3 Promotes Gastrointestinal Stromal Tumor Cell Growth and Drug Resistance," Cancer Research, Mar. 2015, 75(5): 880-892.
Jebar et al., "FGFR3 and Ras gene mutations are mutually exclusive genetic events in urothelial cell carcinoma," Oncogene, 2005, 24: 5218-5225.
Ji et al., "Embase abstract: Modeling and simulation as gating for clinical pharmacology studies of INCB054828," 119th Annual Meeting of the American Society for Clinical Pharmacology and Therapeutics, Mar. 1, 2018, 2 pages.
Jiang et al., "miR-99a promotes proliferation targeting FGFR3 in human epithelial ovarian cancer cells," Biomedicine & Pharmacotherapy, 2014, 68: 163-169.
Johnson et al., "Pharmacological and Functional Comparison of the Polo-like Kinase Family: Insight into Inhibitor and Substrate Specificity," Biochemistry, 2007, 46: 9551-9563.
Jonker et al., "A phase I study to determine the safety, pharmacokinetics and pharmacodynamics of a dual VEGFR and FGFR inhibitor, brivanib, in patients with advanced or metastatic solid tumors," Annals of Oncology, 2010, 1-7.
Jordan, "Tamoxifen: A Most Unlikely Pioneering Medicine," Nature Reviews: Drug Discovery, Mar. 2003, 2:205-213.
Kang et al., FGFR3 Activates RSK2 to Mediate Hematopoietic Transformation through Tyrosine Phosphorylation of RSK2 and Activation of the MEK/ERK Pathway, Cancer Cell, Sep. 2007, 12:201-214.
Kassack et al., "Structure-activity relationships of analogues of NF449 confirm NF449 as the most potent and selective known P2X1 receptor antagonist," European Journal of Medicinal Chemisty, 2004, 345-357.
Katoh and Katoh, "FGF signaling network in the gastrointestinal tract (Review)," International Journal of Oncology, 2006, 29: 163-168.
Keats et al., "Ten years and counting: so what do we know about t(4;14) (p16;q32) multiple myeloma," Leukemia & Lymphoma, Nov. 2006, 47(11): 2289-2300.
Keer et al., "Enrolling a Rare Patient Population: Establishing Proof of Concept for FP-1039, an FGF "Trap," in Endometrial Cancer Patients with the S252W FGFR2 Mutation," Journal of Clinical Oncology, 2010 ASCO Annual Meeting Abstracts, 28:15, May 20 Supplement, 1 page.
Kerekes et. al., "Aurora kinase inhibitors based on the imidazo[1,2-a]pyrazine core: fluorine and deuterium incorporation improve oral absorption and exposure," J Med Chem., 2011, 54(1):201-210.
Khojasteh et al., "Chemical inhibitors of cytochrome P450 isoforms in human liver microsomes: a re-evaluation of P450 isoform selectivity," Eur J Drug Metab Pharmacokinet., Mar. 2011, 36:1-16.
Kim et al., "Phase I/II and Pharmacodynamic Study of Dovitinib (TKI258), an Inhibitor of Fibroblast Growth Factor Receptors and VEGF Receptors, in Patients with Advanced Melanoma," Clin Cancer Res, 2011, 17: 7451-7461.
Kim et al., "The design, synthesis, and biological evaluation of potent receptor tyrosine kinase inhibitors," Bioorganic & Medicinal Chemistry Letters, 2012, 4979-4985.
Klein et al., "FGFR1 Kinase Inhibitors: Close Regioisomers Adopt Divergent Binding Modes and Display Distinct Biophysical Signatures," American Chemical Society, 2014, 166-171.
Knights and Cook, "De-regulated FGF receptors as therapeutic targets in cancer," Pharmacology & Therapeutics, 2010, 125:105-117.
Kompier et al., "Bladder cancer: Novel molecular characteristics, diagnostic, and therapeutic implications," Urologic Oncology: Seminars and Original Investigations, 2010, 91-96.
Kompier et al., "FGFR3, HRAS, KRAS, NRAS and PIK3CA Mutations in Bladder Cancer and Their Potential as Biomarkers for Surveillance and Therapy," PLoS One, Nov. 2010, 5(11): 1-13.
Kono et al., "The fibroblast growth factor receptor signaling pathway as a mediator of intrinsic resistance to EGFR-specific tyrosine kinase inhibitors in non-small cell lung cancer," Drug Resistance Updates, 2009, 95-102.
Korean Office Action in Korean Application No. 10-2015-7000701, dated Aug. 26, 2019, 19 pages.
Korean Office Action in Korean Application No. 10-2015-7032502, dated Sep. 9, 2020, 16 pages.
Korean Office Action in Korean Application No. 10-2020-7021884, dated Oct. 25, 2021, 6 pages.
Korean Office Action in Korean Application No. 10-2020-7021884, dated Oct. 28, 2020, 15 pages.

(56) References Cited

OTHER PUBLICATIONS

Korean Office Action in Korean Application No. 10-2021-7018897, dated Oct. 1, 2021, 15 pages.
Korean Office Action in Korean Application No. 10-2022-7018808, dated Sep. 16, 2022, 5 pages.
Kotha et al., "Recent applications of the Suzuki-Miyaura cross-coupling reaction in organic synthesis," Tetrahedron, 2002, 58:9633-9695.
Koziczak and Hynes, "Cooperation between Fibroblast Growth Factor Receptor-4 and ErbB2 in Regulation of Cyclin D1 Translation," The Journal of Biological Chemistry, 2004, 279(48): 50004-50011.
Koziczak et al., "Blocking of FGFR signaling inhibits breast cancer cell proliferation through downregulation of D-type cyclins," Oncogene, 2004, 23:3501-3508.
Krejci et al., "Molecular pathology of the fibroblast growth factor family," Hum Mutat, Sep. 2009, 30(9): 1245-1255.
Krejci et al., "NF449 Is a Novel Inhibitor of Fibroblast Growth Factor Receptor 3 (FGFR3) Signaling Active in Chondrocytes and Multiple Myeloma Cells," The Journal of Biological Chemistry, Jul. 2010, 285(27): 20644-20653.
Krejci et al., "NF449 is a novel inhibitor of fibroblast growth factor receptor 3 (FGFR3) signaling active in chondrocytes and multiple myeloma cells," The American Society for Biochemistry and Molecular Biology, 2010, 1-20.
Kunii et al., "FGFR2-Amplified Gastric Cancer Cell Lines Require FGFR2 and Erbb3 Signaling for Growth and Survival," Cancer Res., Apr. 1, 2008, 68(7):2340-2348.
Kunii et al., "FGFR2-Amplified Gastric Cancer Cell Lines Require FGFR2 and Erbb3 Signaling for Growth and Survival," Cancer Res., Apr. 1, 2008, Supplemental figures, 11 pages.
Kuroso et al., "Immunohistochemical Detection of Fibroblast Growth Factor Receptor 3 in Human Breast Cancer: Correlation with Clinicopathological/Molecular Parameteres and Prognosis," Pathobiology, Mar. 2010, 77: 231-240.
Kurosu et al., "Regulation of Fibroblast Growth Factor-23 Signaling by Klotho," The Journal of Biological Chemistry, Mar. 2006, 281(10): 6120-6123.
Lala et al., "Role of nitric oxide in tumor progression: Lessons from experimental tumors," Cancer and Metastasis Reviews, 1998, 17: 91-106.
Lammoglia and Mericq, "Familial Tumoral Calcinosis Caused by a Novel FGF23 Mutation: Response to Induction of Tubular Renal Acidosis with Acetazolamide and the Non-Calcium Phosphate Binder Sevelamer," Horm Res, 2009, 71:178-184.
Lamont et al., "Small molecule FGF receptor inhibitors block FGFR-dependent urothelial carcinoma growth in vitro and in vivo," Br. J Cancer, 2010, 1-8.
Lamont et al., "Small molecule FGF receptor inhibitors block FGFR-dependent urothelial carcinoma growth in vitro and in vivo," Br. J Cancer, 2011, 104:75-82.
Le Corre et al., "Synthesis and biological evaluation of a triazole-based library of pyrido[2,3-d]pyrimidines as FGFR3 tyrosine kinase inhibitors," Org. Biomol. Chem., 2010, 8, 2164-2173.
Lee et al., "In vivo Target Modulation and Biological Activity of CHIR-258, a Multitargeted Growth Factor Receptor Kinase Inhibitor, in Colon Cancer Models," Clin Cancer Res, May 2005, 3633-3641.
L'Hote and Knowles, "Cell responses to FGFR3 signalling: growth, differentiation and apoptosis," Experimental Cell Research, 2005, 417-431.
Li et al., "Compound deletion of Fgfr3 and Fgfr4 partially rescues the Hyp mouse phenotype," Am. J. Physiology—Endocrinol Metab, Dec. 7, 2010, 300:3, 29 pages.
Liang et al., "Anticancer molecules targeting fibroblast growth factor receptors," Cell Press, 2012, 11 pages.
Liu et al., "Developing Irreversible Inhibitors of the Protein Kinase Cysteinome," Chemistry & Biology, Feb. 2013, 146-159.
Liu et al., "FRFR3 and FRFR4 Do not Mediate Renal Effects of FGF23," J Am Soc Nephrol, 2008, 19:2342-2350.
Liu et al., "Pathogenic role of Fgf23 in Hyp mice," Am J Physiol Endocrinol Metab 291, Jan. 31, 2006, E38-E49.
Lopes de Menezes et al., "CHIR-258: A Potent Inhibitor of FLT3 Kinase in Experimental Tumor Xenograft Models of Human Acute Myelogenous Leukemia," Clin Cancer Res, Jul. 2005, 5281-5291.
Luo et al., "Deficiency of metabolic regulator FGFR4 delays breast cancer progression through systemic and microenvironmental metabolic alterations," Cancer & Metabolism, 2013, 20 pages.
Maeda et al., "Transforming property of TEL-FGFR3 mediated through PI3-K in a T-cell lymphoma that subsequently progressed to AML," Blood, Mar. 2005, 105(5): 2115-2123.
Malaysian Office Action in Malaysian Application No. 2014003396, dated Dec. 15, 2017, 4 pages.
Marek et al., "Fibroblast Growth Factor (FGF) and FGF Receptor-Mediated Autocrine Signaling in Non-Small-Cell Lung Cancer Cells," Molecular Pharmacology, 2009, 75:196-207.
Marfe and Stefano, "in vitro Anti-leukaemia Activity of Pyrrolo[1,2-b][1,2,5]benzothiadiaze-pines (PBTDs)," Recent Patents on Anti-Cancer Drug Discovery, 2010, 58-68.
Marks et al., "Mutational Analysis of EGFR and Related Signaling Pathway Genes in Lung Adenocarcinomas Identifies a Novel Somatic Kinase Domain Mutation in FGFR4," PLoS One, May 9, 2007, 2:e426.
Marshall et al., "Fibroblast Growth Factor Receptors are Components of Autocrine Signaling Networks in Head and Neck Squamous Cell Carcinoma Cells," Clin Cancer Res., 2011, 17:5016-5025.
Martinez-Torrecuadrada et al., "Targeting the Extracellular Domain of Fibroblast Growth Factor Receptor 3 with Human Single-Chain Fv Antibodies Inhibits Bladder Carcinoma Cell Line Proliferation," Clin Cancer Res, Sep. 2005, 6280-6290.
Martino et al., "Mutant fibroblast growth factor receptor 3 induces intracellular signaling and cellular transformation in a cell type- and mutation-specific manner," Oncogene, 2009, 28: 4306-4316.
Matsuda et al., "Fibroblast Growth Factor Receptor 2 IIIc as a Therapeutic Target for Colorectal Cancer Cells," Mol Cancer Ther., 2012, 52 pages.
McConkey et al., "Molecular genetics of bladder cancer: Emerging mechanisms of tumor initiation and progression," Urologic Oncology: Seminars and Original Investigations, 2010, 429-440.
McMahon, "VEGF Receptor Signaling in Tumor Angiogenesis," Oncologist, 2000, 5(suppl 1):3-10.
Meijer et al., "Fibroblast growth factor receptor 4 predicts failure on tamoxifen therapy in patients with recurrent breast cancer," Endocrine-Related Cancer, 2008, 15:101-111.
Mellor, "Targeted inhibition of the FGF19-FGFR4 pathway in hepatocellular carcinoma; translational safety considerations," Liver International, 2013, 1-9.
Memon et al., "Does Fgf23-klotho activity influence vascular and soft tissue calcification through regulating phosphate homeostasis," Kidney Int., 2008, 74(5): 566-570.
Metzner, "Fibroblast Growth Factor Receptors as Therapeutic Targets in Human Melanoma: Synergism with BRAF Inhibition," J Investigative Dermatol., 2011, 131:2087-2095.
Mexican Office Action in Mexican Application No. MX/a/2014/015192, dated Jan. 24, 2018, 6 pages.
Mexican Office Action in Mexican Application No. MX/a/2019/014097, dated Aug. 11, 2022, 13 pages.
Mexican Office Action in Mexican Application No. MX/a/2020/011639, dated Oct. 25, 2022, 13 pages.
Miyake et al., "1-tert-Butyl-3-[6-(3,5-dimethoxy-phenyl)-2-(4-diethylamino-butylamino)-pyrido[2,3-d]pyrimidin-7-yl]-urea (PD173074), a Selective Tyrosine Kinase Inhibitor of Fibroblast Growth Factor Receptor-3 (FGFR3), Inhibits Cell Proliferation of Bladder Cancer Carrying the FGFR3 Gene Mutation along with Up-Regulation of p27/Kip1 and $G_1/G_0$ Arrest," The Journal of Pharmacology and Experimental Therapeutics, 2010, 332(3):795-802.
Mohammadi et al., "Crystal structure of an angiogenesis inhibitor bound to the FGF receptor tyrosine kinase domain," The EMBO Journal, 1998, 5896-5904.
Mohammadi et al., "Structures of the Tyrosine Kinase Domain of Fibroblast Growth Factor Receptor in Complex with Inhibitors," Science, May 1997, 276:955-960.

(56) References Cited

OTHER PUBLICATIONS

Murphy et al., "Evidence for distinct alterations in the FGF axis in prostate cancer progression to an aggressive clinical phenotype," J Pathol., 2010, 220:452-460.
Naito et al., "Progressive tumoral calcinosis as the presenting feature of sarcoidosis in a patient on haemodialysis treatment," Nephrol Dial Transplant, 1999, 14:2716-2719.
Nakatani et al., "In vivo genetic evidence for klotho-dependent, fibroblast growth factor 23 (Fgf23)-mediated regulation of systemic phosphate homeostasis," The FASEB Journal, Feb. 2009, 23:433-441.
Natajaran et al., "p38 MAP kinase inhibitors. Part 3: SAR on 3,4-dihydropyrimido-[4,5-d]pyrimidin-2-ones and 3,4-dihydropyrido[4,3-d]-pyrimidin-2-ones," Bioorgan. Med. Chem. Lett., 2006, 4400-4404.
Neidle et al., "Failure Modes in the Discovery Process," Cancer Drug Design, 2008, pp. 427-431.
New Zealand Examination Report in New Zealand Application No. 743274, dated Jul. 18, 2018, 4 pages.
New Zealand Office Action in New Zealand Application No. 702747, dated Mar. 8, 2019, 2 pages.
New Zealand Office Action in New Zealand Application No. 702747, dated Sep. 16, 2016, 3 pages.
New Zealand Office Action in New Zealand Application No. 713074, dated Feb. 18, 2020, 3 pages.
New Zealand Office Action in New Zealand Application No. 743274, dated Jul. 19, 2018, 5 pages.
New Zealand Office Action in New Zealand Application No. 752422, dated Feb. 18, 2020, 2 pages.
Nitta, "Relationship between Fibroblast Growth Factor-23 and Mineral Metabolism in Chronic Kidney Disease," International Journal of Nephrology, 2010, 1-7.
Nomura et al., "FGF10/FGFR20 signal induces cell migration and invasion in pancreatic cancer," Br. J Cancer, 2008, 99:305-313.
Norman et al., "Protein-Ligand Crystal Structures Can Guide the Design of Selective Inhibitors of the FGFR Tyrosine Kinase," J. Med. Chem., 2012, 55(11):5003-5012.
Novelli, "Fosrenol (TM) reduces damaging high levels of phosphate in end-stage kidney disease patients," EurekAlert!, Nov. 2, 2002 [retrieved on Dec. 1, 2020], retrieved from URL <https://www.eurekalert.org/pub_releases/2002-11/pn-fr110202.php>, 4 pages.
Office Action from the Intellectual Property Office of the Philippines in Application No. 1-2014-502772, dated Mar. 17, 2016, 3 pages.
Ornitz et al., "Receptor Specificity of the Fibroblast Growth Factor Family," The Journal of Biological Chemistry, 1996, 271(25): 15292-15297.
Pai et al., "Antibody-Mediated Inhibition of Fibroblast Growth Factor 19 Results in Increased Bile Acids Synthesis and Ileal Malabsortion of Bile Acides in Cynomolgus Monkeys," Toxicological Sciences, 2012, 126(2): 446-456.
Pan et al., "MK-2461, a Novel Multitargeted Kinase Inhibitor, Preferentially Inhibits the Activated c-Met Receptor," Cancer Res, Feb. 2010, 1524-1533.
Pandith et al., "Oncogenic role of fibroblast growth factor receptor 3 in tumorigenesis of urinary bladder cancer," Urologic Oncology: Seminars and Original Investigations, 2010, 1-9.
Pandith et al., "Oncogenic role of fibroblast growth factor receptor 3 in tumorigenesis of urinary bladder cancer," Urologic Oncology: Seminars and Original Investigations, 2013, 31: 398-406.
Pardo et al., "The Fibroblast Growth Factor Receptor Inhibitor PD173074 Blocks Small Cell Lung Cancer Growth In vitro and In vivo," Cancer Res, Nov. 2009, 8645-8651.
Paterson et al., "Preclinical studies of fibroblast growth factor receptor 3 as a therapeutic target in multiple myeloma," British Journal of Haematology, 2004, 124:595-603.
Peruvian Office Action in Peruvian Application No. 1424, dated Mar. 12, 2021, 13 pages.
Peruvian Office Action in Peruvian Application No. 1429, dated Mar. 19, 2021, 12 pages.
Peruvian Office Action in Peruvian Application No. 2433, dated Nov. 27, 2018, 13 pages.
Philippine Office Action in Philippine Application No. 1/2015/502383, dated Nov. 11, 2021, 4 pages.
Philippine Office Action in Philippine Application No. 1/2017/501483, dated Dec. 12, 2019, 5 pages.
Philippine Office Action in Philippine Application No. 1/2019/502810, dated Dec. 7, 2021, 4 pages.
Philippine Office Action in Philippine Application No. 1-2017-501481, dated Oct. 29, 2019, 4 pages.
Philippine Office Action in Philippine Application No. 1/2015/502383, dated Jul. 8, 2019, 7 pages.
Philippine Office Action in the Philippine Application No. 1/2017/501483, dated Aug. 31, 2020, 4 pages.
Piazza et al., "Towards a new age in the treatment of multiple myeloma," Ann Hematol, 2007, 86:159-172.
Pinedo and Slamon, "Translational Research: The Role of VEGF in Tumor Angiogenesis," Oncologist, 2000, 5(suppl 1):1-2.
Piro et al., "An FGFR3 Autocrine Loop Sustains Acquired Resistance to Trastuzumab in Gastric Cancer Patients," Clinical Cancer Research, Dec. 2016, 22(24): 6164-6175.
Platt et al., "Spectrum of Phosphatidylinositol 3-Kinase Pathway Gene Alterations in Bladder Cancer," Clin Cancer Res, Oct. 2009, 6008-6017.
Pliarchopoulou et al., "Current chemotherapeutic options for the treatment of advanced bladder cancer: A review," Urologic Oncology: Seminars and Original Investigations, 2010, 1-9.
Plowright et al., "Ectopic expression of fibroblast growth factor receptor 3 promotes myeloma cell proliferation and prevents apoptosis," Blood, Feb. 2000, 95(3): 992-998.
Podar et al., "Emerging therapies for multiple myeloma," Expert Opin. Emerging Drugs, 2009, 14(1):9-127.
Podar et al., "Targeting signalling pathways for the treatment of multiple myeloma," Expert Opin. Ther. Targets, 2005, 359-381.
Pollett et al., "Overexpression of the myeloma-associated oncogene fibroblast growth factor receptor 3 confers dexamethasone resistance," Blood, Nov. 2002, 100(10): 3819-3821.
Pollock et al., "Frequent activating FGFR2 mutations in endometrial carcinomas parallel germline mutations associated with craniosynostosis and skeletal dysplasia syndromes," Oncogene, 2007, 26:7158-7162.
Porta, "FGFR a promising druggable target in cancer: Molecular biology and new drugs." Critical reviews in oncology hematology, 2017, 113:256-267.
Propper et al., "Phase I and Pharmacokinetic Study of PKC412, an Inhibitor of Protein Kinase C," J Clin Oncol, 2001, 19(5):1485-1492.
Qian et al., "Targeting Tumor Angiogenesis with Histone Deacetylase Inhibitors: the Hydroxamic Acid Derivative LBH589," Clin Cancer Res, Jan. 2006, 634-642.
Qing et al., "Antibody-based targeting of FGFR3 in bladder carcinoma and t(4;14)-positive multiple myeloma in mice," The Journal of Clinical Investigation, May 2009, 119(5): 1216-1229.
Qing et al., "Antibody-based targeting of FGFR3 in bladder carcinoma and t(4;14)-positive multiple myeloma in mice," The Journal of Clinical Investigation, May 2009, Supplemental Table 1: Summary of crystallographic analysis, 21 pages.
Qiu et al., "Over-expression of fibroblast growth factor receptor 3 in human hepatocellular carcinoma," World J Gastroenterol, 2005, 11(34): 5266-5272.
Raab et al., "Multiple myeloma," Lancet, 2009, 374: 324-339.
Ravindranathan et al., "Discovery of Novel Fibroblast Growth Factor Receptor 1 Kinase Inhibitors by Structure-Based Virtual Screening," J. Med. Chem., 2010, 53: 1662-1672.
Razzaque, "FGF23-mediated regulation of systemic phosphate homeostasis: is Klotho an essential player?," Am J Physiol Renal Physiol, 2009, 470-476.
Reimers et al., "NoBP, a Nuclear Fibroblast Growth Factor 3 Binding Protein, Is Cell Cycle Regulated and Promotes Cell Growth," Molecular and Cellular Biology, Aug. 2001, 21(15): 4996-5007.
Reis-Filho et al., "FGFRI Emerges as a Potential Therapeutic Target for Lobular Breast Carcinomas," Clin Cancer Res, Nov. 2006, 6652-6662.

(56) References Cited

OTHER PUBLICATIONS

Reiter et al., "Consistent Fusion of ZNF198 to the Fibroblast Growth Factor Receptor-1 in the t(8;13)(p11;q12) Myeloproliferative Syndrome," Blood, Sep. 1998, 92(5): 1735-1742.
Remington, "The Science and Practice of Pharmacy," Lippincott Williams & Wilkins, 2005, 21st edition.
Remington's Pharmaceutical Sciences, 17th ed., Mack Publishing Company, Easton, Pa., 1985, p. 1418*.
Renhowe et al., "Design, Structure—Activity Relationships and in Vivo Characterization of 4-Amino-3-benzimidazol-2-ylhydroquinolin-2-ones: A Novel Class of Receptor Tyrosine Kinase Inhibitors," J. Med. Chem., 2009, 52: 278-292.
Ribatti et al., "The discovery of basic fibroblast growth factor/fibroblast growth factor-2 and its role in haematological malignancies," Cytokine & Growth Factor Reviews, 2007, 18: 327-334.
Ribatti, "Tyrosine Kinase Inhibitors as Antiangiogenic Drugs in Multiple Myeloma," Pharmaceuticals, 2010, 3: 1225-1231.
Roidl et al., "Resistance to Chemotherapy Is Associated with Fibroblast Growth Factor Receptor 4 Up-Regulation," Clin Cancer Res, Mar. 2009, 2058-2066.
Ronchetti et al., "Deregulated FGFR3 mutants in multiple myeloma cell lines with t(4;14): comparative analysis of Y373C, K650E and the novel G384D mutations," Oncogene, 2001, 20: 3553-3562.
Roumiantsev et al., "Distinct stem cell myeloproliferative/T lymphoma syndromes induced by ZNF198-FGFR1 and BCR-FGFRI fusion genes from 8p11 translocations," Cancer Cell, Mar. 2004, 5: 287-298.
Rowe et al., "Handbook of Pharmaceutical Additives," The Pharmaceutical Press and the American Pharmaceutical Association, 2009, 3rd ed.
Rowe et al., "Handbook of Pharmaceutical Excipients," The Pharmaceutical Press and the American Pharmaceutical Association, 2009, 6th Edition, 917 pages.
Ryan et al., "Toxicologic Pathology of Unique Biotechnology Agents and Biotherapies," Toxicologic Pathology, 1999, 27(1): 78-86.
Sakurai et al., "A novel angiogenesis inhibitor, Ki23057, is useful for preventing the progression of colon cancer and the spreading of cancer cells to the liver," European Journal of Cancer, 2007, 2612-2620.
Sarker et al., "A Phase I Pharmacokinetic and Pharmacodynamic Study of TKI258, an Oral, Multitargeted Receptor Tyrosine Kinase Inhibitor in Patients with Advanced Solid Tumors," Clin Cancer Res, Apr. 2008, 2075-2081.
Saxty et al., "Fragment-based drug discovery of selective inhibitors of fibroblast growth factor receptor (FGFr)," Cancer Res, Apr. 15, 2010, 70, 5778.
Schenone et al., "Small Molecules ATP-Comptetitive Inhibitors of FLT3: A Chemical Overview," Current Medicinal Chemistry, 2008, 15(29): 3113-3132.
Schlapbach et al., "A novel Pd-catalyzed cyclization rection of ureas for the synthesis of dihydroquinazolinone p38 kinase inhibitors," Bioorg. Med. Chem. Lett., 2004, 357-360.
Science IP Order 3032627, Chemical Structure Search, Science IP, Apr. 2012, 78 pages.
Science IP Order 3101926, Chemical Structure Search, Science IP, Jan. 2015, 50 pages.
Science IP Order 3101983, Chemical Structure Search, Science IP, Jan. 2015, 70 pages.
Science IP Order 3104564, Patent Chemical Structure Search, Science IP, Mar. 2015, 90 pages.
Science IP Order 3104565, Patent Chemical Structure Search, Science IP, Mar. 2015, 521 pages.
Segev et al., "Restrained chondrocyte proliferation and maturation with abnormal growth plate vascularization and ossification in human FRFR-3$^{G380R}$ transgenic mice," Human Molecular Genetics, 2000, 9(2): 249-258.
Seitzer et al., "A single nucleotide change in the mouse genome accelerates breast cancer progression," Cancer Res., Jan. 2010, 70(2):802-812.
Shariat et al., "Association of Angiogenesis Related Markers With Bladder Cancer Outcomes and Other Molecular Markers," The Journal of Urology, May 2010, 183: 1744-1750.
Sharkey et al., "PKC412 demonstrates JNK-dependent activity against human multiple myeloma cells," Blood, Feb. 2007, 109(4): 1712-1719.
Shi et al., "High Expression of FGFR4 Enhances Tumor Growth and Metastasis in Nasopharyngeal Carcinoma," Journal of Cancer, 2015, 6(12): 1245-1254.
Shinya et al., "Fgf signalling through MAPK cascade is required for development of the subpallial telencephalon in zebrafish embryos," Development, 2001, 4153-4164.
sigmaaldrich.com, "4-Chloro-1H-pyrrolo[2,3-b]pyridine-5-carbaldehyde," CAS # 958230-19-8, [retrieved on Feb. 4, 2021] retrieved from URL <https://www.sigmaaldrich.com/catalog/product/aldrich/ade000976?lang=en&region=US>, 2 pages.
Singh et al., "Transforming Fusions of FGFR and TACC Genes in Human Glioblastoma," Science, Sep. 2012, 337:1231-1235.
Slavin et al., "Familial Tumoral Calcinosis," The American Journal of Surgican Pathology, 1993, 17(8): 188-802.
Smith et al., "Circulating αKlotho influences phosphate handling by controlling FGF23 production," The Journal of Clinical Investigation, Dec. 2012, 122(12): 4710-4715.
Song et al., "Fibroblast growth factors: An epigenetic mechanism of broad spectrum resistance to anticancer drugs," PNAS, Jul. 2000, 97(15): 8658-8663.
Sonvilla et al., "Fibroblast growth factor receptor 3-IIIc mediates colorectal cancer growth and migration," British Journal of Cancer, 2010, 1-12.
Soria, "FGFR inhibition overview of clinical development programs," Presentation, presented at TAT in Washington DC on Mar. 5-7, 2014, 54 pages.
Soverini et al., "Novel mutation and RNA splice variant of fibroblast growth factor receptor 3 in multiple myeloma patients at diagnosis," Haematologica, 2002, 87: 1036-1040.
Specktor et al., "Hyperphosphatemic familial tumoral calcinosis caused by a mutation in GALNT3 in a European kindred," J Hum Genet, 2006, 51:487-490.
Squires et al., "Development of inhibitors of the fibroblast growth factor receptor (FGFR) kinase using a fragment based approach," Cancer Res 70, Apr. 15, 2010, 3626.
Squires et al., "Development of inhibitors of the fibroblast growth factor receptor (FGFR) kinase using a fragment based approach," Cancer Res, 2008, 1 page.
Staerk et al., "Pan-Src Family Kinase Inhibitors Replace Sox2 during the Direct Reprogramming of Somatic Cells," Angewandte Chem., Jun. 14, 2011, 50(25):5734-5736.
STN International Search Report for CAS RN 2380276-25-3, dated Nov. 20, 2019, 11 pages.
STN Search Report dated Jan. 6, 2020, 88 pages.
STN Search Report, dated Sep. 11, 2019, 31 pages.
Sun et al., "Design, Synthesis, and Evaluations of Substituted 3-[(3- or 4-Carboxyethylpyrrol-2-yl)methylidenyl]indolin-2-ones as Inhibitors of VEGF, FGF, and PDGF Receptor Tyrosine Kinases," J. Med. Chem., 1999, 42: 5120-5130.
Sun et al., "Identification of Substituted 3-[(4,5,6,7-Tetrahydro-1H-indol-2-yl)methylene]-1,3-dihydroindol-2-ones as Growth Factor Receptor Inhibitors for VEGF-R2 (Flk-1/KDR), FGF-R1, and PDGF-Rβ Tyrosine Kinases," J. Med. Chem., 2000, 43: 2655-2663.
Sun et al., "Synthesis and Biological Evaluations of 3-Substituated Indolin-2-ones: A Novel Class of Tyrosine Kinase Inhibitors That Exhibit Selectivity toward Particular Receptor Tyrosine Kinases," J. Med. Chem., 1998, 41: 2588-2603.
Surry et al., "Dialkylbiaryl Phosphines in Pd-Catalyzed Amination: A User's Guide," Chem Sci., 2011, 2(1):27-50.
Taiwan Office Action in Taiwan Application No. 103114284, dated Apr. 9, 2018, 4 pages (English Search Report).
Taiwan Office Action in Taiwan Application No. 105104993, dated Feb. 11, 2020, 9 pages.
Taiwan Office Action in Taiwan Application No. 105105018, dated Oct. 22, 2019, 7 pages.
Taiwan Office Action in Taiwan Application No. 107146498, dated Dec. 19, 2019, 7 pages.

(56) References Cited

OTHER PUBLICATIONS

Taiwan Office Action in Taiwan Application No. 109132389, dated Aug. 23, 2021, 4 pages.
Taiwanese Office Action in Taiwan Application No. 102120946, dated Nov. 9, 2016, 9 pages (with English translation).
Taiwanese Office Action in Taiwanese Application No. 102120946, dated Jul. 13, 2017, 7 pages (English Translation).
Takeda et al., "AZD2171 Shows Potent Antitumor Activity Against Gastric Cancer Over-Expressing Fibroblast Growth Factor Receptor 2/Keratinocyte Growth Factor Receptor," Clin Cancer Res, May 2007, 3051-3057.
Takii et al., "Serotonin Derivative, N-(p-Coumaroyl)serotonin, Isolated from Safflower (*Carthamus tinctorius* L.) Oil Cake Augments the Proliferation of Normal Human and Mouse Fibroblasts in Synergy with Basic Fibroblast Growth Factor (bFGF) or Epidermal Growth Factor (EGF)", J Biochem., 1995, 125(5):910-915.
Tan et al., "Development of covalent inhibitors that can overcome resistance to first-generation FGFR kinase inhibitors," PNAS, Oct. 2014, E4869-E4877.
Tang et al., "Role of fibroblast growth factor receptor 4 in cancer," Cancer Science, Oct. 2018, 109(10):3024-3031.
Taylor et al., "Identification of FGFR4-activating mutations in human rhabdomyasarcomas that promote metastasis in xenotransplanted models," J Clin Invest., Nov. 2009, 119(11):3395-3407.
Taylor, "Inhibitor PD-173074 Bound to the Tyrosine Kinase Domain of FGFR 1," Molecular & Behavioral Neuroscience Institute , Feb. 2006, 1 page.
Taylor, "Inhibitor SU-5402 Bound to the Tyrosine Kinase Domain of FGFR 1," Molecular & Behavioral Neuroscience Institute , Apr. 2006, 1 page.
Terai et al., "Vascular calcification and secondary hyperparathyroidism of severe chronic kidney disease and its relation to serum phosphate and calcium levels," British Journal of Pharmacology, 2009, 156: 1267-1278.
Thai Office Action in Thai Application No. 1401007417, dated Jun. 5, 2016, 7 pages (with English translation).
The Cancer Genome Atlas Research Network, "Comprehensive molecular characterization of urothelial bladder carcinoma," Nature, 2014, 507: 315-22.
Thome and Weil, "Post-translational modifications regulate distinct functions of CARMA1 and BCL10," Trends in Immunology, 2007, 28(6): 281-288.
Thompson et al., "3-(3,5-Dimethoxyphenyl)-1,6-naphthyridine-2,7-diamines and Related 2-Urea Derivatives Are Potent and Selective Inhibitors of the FGF Receptor-1 Tyrosine Kinase," J. Med. Chem., 2000, 43: 4200-4211.
Thompson et al., "Photochemical Preparation of a Pyridone Containing Tetracycle: A Jak Protein Kinase Inhibitor," Bioorganic & Medicinal Chemistry Letters 12:1219-1223, 2002.
Thompson et al., "Synthesis and Structure—Activity Relationships of Soluble 7-Substituted 3-(3,5-Dimethoxyphenyl)-1,6-naphthyridin-2-amines and Related Ureas as Dual Inhibitors of the Fibroblast Growth Factor Receptor-1 and Vascular Endothelial Growth Factor Receptor-2 Tyrosine Kinases," J. Med. Chem., 2005, 48: 4628-2653.
Thussbas et al., "FGFR4 Arg388 Allele Is Associated With Resistance to Adjuvant Therapy in Primary Breast Cancer," J. Clin. Oncol., Aug. 10, 2006, 23:3747-3755.
Tolcher et al., "381 Preliminary results of a dose escalation study of the Fibroblast Growth Factor (FGF) "trap" FP-1039 (FGFR1:Fc) in patients with advanced malignancies," EJC Supplements, Nov. 2010, 8:7, p. 121.
Tomlinson et al., "FGFR3 protein expression and its relationship to mutation status and prognostic variables in bladder cancer," J Pathol, Sep. 2007, 213(1): 91-98.
Tomlinson et al., "Fibroblast Growth Factor Receptor 1 Promotes Proliferation and Survival via Activation of the Mitogen-Activated Protein Kinase Pathway in Bladder Cancer," Cancer Res, 2009, 4613-4620.
Tomlinson et al., "Knockdown by shRNA identifies S249C mutant FGFR3 as a potential therapeutic target in bladder cancer," Oncogene, 2007, 26: 5889-5899.
Topaz et al., "Mutations in GALNT3, encoding a protein involved in O-linked glycosylation, cause familial tumoral calcinosis," Nature Genetics, 2004, 1-3.
Traxler and Furet, "Strategies toward the Design of Novel and Selective Protein Tyrosine Kinase Inhibitors," Pharmacol. Ther., 1999, 82(2-3): 195-206.
Trudel et al., "CHIR-258, a novel, multitargeted tyrosine kinase inhibitor for the potential treatment of t(4;14) multiple myeloma," Blood, Apr. 2005, 105(7): 2941-2948.
Trudel et al., "Inhibition of fibroblast growth factor receptor 3 induces differentiation and apoptosis in t(4;14) myeloma," Blood, May 2004, 103(9):3521-3528.
Trudel et al., "The inhibitory anti-FGFR3 antibody, PRO-001, is cytotoxic to t(4;14) multiple myeloma cells," Blood, May 2006, 107(10): 4039-4046.
Trudel, "CHIR-258, a Novel Multi-targeted tyrosine KinaseInhibitor, for the Treatment of t(4;14) Multiple Myeloma," Presentation, Presented at International Myeloma Foundation, Apr. 2005, 18 pages.
Turkington et al., "Fibroblast growth factor receptor 4 (FGFR4): a targetable regulator of drug resistance in colorectal cancer," Cell Death Dis., Feb. 6, 2014, 5:e1046.
Turner and Grose, "Fibroblast growth factor signalling: from development to cancer," Nature Reviews Cancer, 2010, 10:116-129.
Turner et al., "FGFR1 Amplification Drives Endocrine Therapy Resistance and Is a Therapeutic Target in Breast Cancer," Cancer Res., Mar. 2010, 2085-2094.
Tvorogov et al., "Effective Suppression of Vascular Network Formation by Combination of Antibodies Blocking VEGFR Ligand Binding and Receptor Dimerization," Cancer Cell, Dec. 2010, 18: 630-640.
Ueno et al., "Enhanced Expression of Fibroblast Growth Factor Receptor 3 IIIc Promotes Human Esophageal Carcinoma Cell Proliferation," Journal of Histochemistry & Cytochemistry, 2016, 64(1): 7-17.
Ukraine Office Action in Ukraine Application No. a 2019 12195, dated Nov. 11, 2021, 7 pages.
Ukraine Office Action in Ukraine Application No. a201500191, dated Dec. 13, 2016, 10 pages (with English translation).
Ukraine Office Action in Ukraine Application No. a201511370, dated Nov. 12, 2018, 6 pages (with English translation).
Ukraine Office Action in Ukraine Application No. a201709220, dated Dec. 9, 2019, 11 pages.
Ukraine Office Action in Ukraine Application No. a201801562, dated Jul. 28, 2021, 9 pages.
Ukraine Office Action in Ukraine Application No. a202007685, dated Oct. 31, 2022, 13 pages.
Ukraine Office Action in Ukraine Application No. a202007700, dated Sep. 13, 2022, 11 pages.
Urakawa et al., "Klotho converts canonical FGF receptor into a specific receptor for FGF23," Nature, Dec. 2006, 444: 770-774.
Uzawa et al., "Targeting fibroblast growth factor receptor 3 enhances radiosensitivity in human squamous cancer cells," Oncogene, 2011, 1-6.
Van Oers et al., "FGFR3 Mutations Indicate Better Survival in Invasive Upper Urinary Tract and Bladder Tumours," European Urology, 2009, 650-658.
Våtsveen et al., "FGFR3 is expressed and is important for survival in INA-6, a human myeloma cell line without a t(4;14)," Eur. J. Haematol., 83:5, Jul. 6, 2009, 471-476.
Verstovsek et al., "Interim Results from Fight-203, a Phase 2, Open-Label, Multicenter Study Evaluating the Efficacy and Safety of Pemigatinib (INCB054828) in Patients with Myeloid/Lymphoid Neoplasms with Rearrangement of Fibroblast Growth Factor Receptor 1 (FGFR1)," Blood, Nov. 29, 2018, retrieved from URL <https://ashpublications.org/blood/article/132/Supplement%201/690/266005/Interim-Results-from-Fight203-a-Phase-2-0penLabel>, 132(Supplement 1):690.
Vietnamese Office Action in Vietnamese Application No. 1-2015-00102, dated Mar. 18, 2015, 4 pages.

(56) References Cited

OTHER PUBLICATIONS

Vogt et al., "FGF23 and phosphate cardiovascular toxins in ckd," Toxins, Nov. 6, 2019, 11(11):647.
Von Massenhausen et al., "Evaluation of FGFR3 as a Therapeutic Target in Head and Neck Squamous Cell Carcinoma," Targ. Oncol., 2016, 11: 631-642.
Walsky and Obach, "Validated assays for human cytochrome P450 activities," Drug Metab Dispos., 2004, 32(6):647-660.
Walsky et al., "Evaluation of 227 drugs for in vitro inhibition of cytochrome P450 2B6," J Clin Pharmacol., Dec. 2006, 46(12):1426-1438.
Wang and Becker, "Antisense targeting of basic fibroblast growth factor and fibroblast growth factor receptor-1 in human melanomas blocks intratumoral angiogenesis and tumor growth," Nature Medicine, Aug. 1997, 887-893.
Wang and Ding, "Fibroblast growth factor receptors in breast cancer," Tumor Biology, May 1-10, 2017.
Wang et al., "The fibroblast growth factor receptor-4 Arg388 allele is associated with prostate cancer initiation and progression," Clin Cancer Res. 2004, 10:6169-6178.
Ware et al., "Rapidly Acquired Resistance to EFGR Tyrosine Kinase Inhibitors in NSCLC Cell Lines through De-Repression of FGFR2 and FGFR3 Expression," PLoS, Nov. 2010, 5(11): 1-9.
Weiss et al., Frequent and Focal FGFR1 Amplification Associates with Therapeutically Tractable FGFRI Dependency in Squamous Cell Lung Cancer, Sci. Transl. Med., 2010, 2(62):62ra93, pp. 1-7.
Williams et al., "Oncogenic FGFR3 gene fusions in bladder cancer," Hum Mol Genet, 2013, 22:795-803.
Wu, "Urothelial Tumorigenesis: A Tale Of Divergent Pathways," Nature Reviews, Sep. 2005, 5: 713-725.
Wuts et al., "Greene's Protective Groups in Organic Synthesis," 4th Ed., 2006, Chapter 7, 696-926.
Wöhrle et al., "FGF Receptors Control Vitamin D and Phosphate Homeostasis by Mediating Renal FGF-23 Signaling and Regulating FGF-23 Expression in Bone," Journal of Bone and Mineral Research, Oct. 2011, 26(10): 2486-2497.
Wöhrle et al., "Pharmacological inhibition of FGFR signaling ameliorates FGF23-mediated hypophosphatemic rickets," Journal of Bone and Mineral Research, 2012, 1-36.
Xian et al., "Pleiotropic effects of FGFR1 on cell proliferation, survival, and migration in a 3D mammary epithelial cell model," JCB, 2005, 171(4): 663-673.
Xin et al., "CHIR-258 Is Efficacious in A Newly Developed Fibroblast Growth Factor Receptor 3-Expressing Orthotopic Multiple Myeloma Model in Mice," Clin Cancer Res, Aug. 2006, 4908-4915.
Xu et al., "Fibroblast growth factor receptor 4 promotes progression and correlates to poor prognosis in cholangiocarcinoma," Biochemical and Biophysical Research Communications, 2014, 446: 54-60.
Xu et. al. "Design, synthesis and biological evaluation of deuterated nintedanib for improving pharmacokinetic properties," J Label Compd Radiopharm., 2015, 58(7):308-312.
Ye et al., "Combination of the FGFR4 inhibitor PD173074 and 5-fluorouracil reduces proliferation and promotes apoptosis in gastric cancer," Oncol Rep., Dec. 2013, 30(6):2777-2784.
Ying et al., "Genome-wide screening for genetic alterations in esophageal cancer by aCGH identifies 11q13 amplification oncogenes associated with nodal metastasis," PLoS One, Jun. 25, 2012, 7:e39797.
Yu et al., "Analysis of the Biochemical Mechanisms for the Endocrine Actions of Fibroblast Growth Factor-23," Endocrinology, Nov. 2005, 146(11): 4647-4656.
Yu et al., "FGFR-4 Arg(3)(8)(8) enhances prostate cancer progression via extracellular signal-related kinase and serum response factor signaling," Clin Cancer Res., Jul. 2011, 17:4355-4366.
Zaid et al., "Identification of FGFR4 as a Potential Therapeutic Target for Advanced-Stage, High-Grade Serous Ovarian Cancer," Clin Cancer Res, 2013, 19(4): 809-820.
Zhang et al., "AZD4547, a potent and selective FGF-receptor inhibitor induces tumor regressions in a human primary model of FGF-receptor 2 amplified gastric cancer and is efficacious in combination with chemotherapy," 2012, AstraZeneca, 1 page.
Zhang et al., "Direct Cell Cycle Regulation by the Fibroblast Growth Factor Receptor (FGFR) Kinase through Phosphorylation-dependent Release of Cks1 from FGFR Substrate 2," The Journal of Biological Chemistry, 2004, 279(53): 55348-55354.
Zhang et al., "Enhanced FGFR signalling predisposes pancreatic cancer to the effect of a potent FGFR inhibitor in preclinical models," British Journal of Cancer, 2014, 110: 320-329.
Zhang et al., "FP-1039 (FGFR1:Fc), A Soluble FGFR1 Receptor Antagonist, Inhibits Tumor Growth and Angiogenesis," Mol Cancer Ther, Nov. 6, 2007, B55.
Zhang et al., "Predicting Drug-Drug Interactions: An FDA Perspective," The AAPS Journal, May 6, 2009, 11(2):300-306.
Zhang et al., "Recent progress in therapeutic and diagnostic applications of lanthanides," Mini-Reviews in Medicinal Chemistry, 2011, 11(8):678-694.
Zhang et al., "Receptor Specificity of the Fibroblast Growth Factor Family," Journal of Biological Chemistry, Jun. 2006, 281(23): 15694-15700.
Zhang et al., "Translating the therapeutic potential of AZD4547 in FGFR1-amplified non-small cell lung cancer through the use of patient derived tumor xenograft (PDTX) models," Clin cancer Res, Oct. 18, 2012, 40 pages.
Zhao et al., "A Novel, Selective Inhibitor of Fibroblast Growth Factor Receptors That Shows a Potent Broad Spectrum of Antitumor Activity in Several Tumor Xenograft Models," Mol Cancer Ther, Nov. 2011, 2200-2210.
Zhao et al., "Homozygous Deletions and Chromosome Amplifications in Human Lung Carcinomas Revealed by Single Nucleotide Polymorphism Array Analysis," Cancer Res, Jul. 2005, 5561-5570.
Zhou et al., "A Structure-Guided Approach to Creating Covalent FGFR Inhibitors," Chemistry and Biology, Mar. 2010, 285-295.
Zhu et al., "Fibroblast growth factor receptor 3 inhibition by short hairpin RNAs leads to apoptosis in multiple myeloma," Mol Cancer Ther, May 2005, 787-798.
Zieger et al., "Role of Activating Fibroblast Growth Factor Receptor 3 Mutations in the Development of Bladder Tumors," Clin Cancer Res, Nov. 2005, 7709-7719.
Brazil Office Action in Brazil Application No. BR122020015574-4, dated Dec. 13, 2022, 12 pages (with Machine Translation).
Colombia Office Action in Colombia Application No. NC2020/0015228, dated Jun. 16, 2023, 21 pages (with English Translation).
Colombian Office Action in Colombian Application No. NC2019/0014699, dated Apr. 27, 2023, 30 pages (with English translation).
Hanna, "Clinical Overview of Enfortumab Vedotin in the Management of Locally Advanced or Metastatic Urothelial Carcinoma," Drugs, Dec. 2019, 80:1-7.
Indian Office Action in Indian Application No. 202017052853, dated May 17, 2023, 2 pages.
Korean Office Action in Korean Application No. 10-2019-7038203, dated Jun. 8, 2023, 15 pages (with English translation).
Mexican Office Action in Mexican Application No. MX/a/2020/011639, dated May 23, 2023, 14 pages (with machine translation).
Philippines Office Action in Philippines Application No. 1-2019-502809, dated Jun. 1, 2023, 6 pages.
Serajuddin, "Salt formation to improve drug solubility," Adv Drug Deliv Rev, Jul. 2007, 59(7):603-616.
Taiwanese Office Action in Taiwan Application No. 11107608, dated Dec. 26, 2022, 7 pages (with English Translation).
Ukraine Office Action in Ukraine Application No. a201912195, dated Jun. 14, 2023, 13 pages.
Argentinian Office Action in Argentinian Application No. 20200100111, dated Apr. 18, 2024, 12 pages (with English Translation).
Argentinian Office Action in Argentinian Application No. 20210101214, dated Apr. 22, 2024, 12 pages (with English Translation).
Bazyl' et al., "The selective ortho-methoxylation of pentafluorobenzoic acid—a new way to tetrafluorosalicylic acid and its derivatives." Journal of fluorine chemistry, Feb. 11, 1999, 94(1):11-13.
Bhatia et al., "Polymorphism and its Implications in Pharmaceutical Product Development," Dosage Form Design Parameters, 2018, pp. 31-65.

(56) References Cited

OTHER PUBLICATIONS

Blagden et al., "Crystal engineering of active pharmaceutical ingredients to improve solubility and dissolution rates," Advanced Drug Delivery Reviews, Jul. 2007, 59(7):617-630.
Canadian Office Action in Canadian Application No. 3064894, dated Jun. 28, 2024, 10 pages.
Colombian Office Action in Colombian Application No. NC2020/0015226, dated May 20, 2024, 16 pages (with English Translation).
Columbian Office Action in Columbian Application No. 2019/0014699, dated Nov. 1, 2023, 37 pages (with English Translation).
Columbian Office Action in Columbian Application No. NC2019/0014699, dated May 20, 2024, 44 pages (with English Translation).
Costa Rican Office Action in Costa Rican Application No. 2019-0573, dated May 31, 2024, 20 pages (with Machine Translation).
Extended European Search Report in European Application No. 23197192.0, dated Feb. 22, 2024, 9 pages.
Gupta et al., "Salts of Therapeutic Agents: Chemical, Physicochemical, and Biological Considerations," Molecules, Jul. 14, 2018, 23(7):1-14.
Heinrich et al., "Fragment-based discovery of new highly substituted 1 H-pyrrolo [2, 3-b]-and 3 H-imidazolo [4, 5-b]-pyridines as focal adhesion kinase inhibitors." Journal of medicinal chemistry, Feb. 14, 2013, 56(3):1160-70.
Indian Oral Hearing Notice in Indian Application No. 201717030267, dated Nov. 29, 2023, 3 pages.
Indian Oral Hearing Notice in Indian Application No. 201917050123, dated Jan. 29, 2024, 2 pages.
Indian Oral Hearing Notice in Indian Application No. 202017052609, dated Feb. 6, 2024, 3 pages.
International Preliminary Report on Patentability in International Application No. PCT/US2020/024210, dated Oct. 12, 2023, 7 pages.
Morissette et al., "High-throughput crystallization: polymorphs, salts, co-crystals and solvates of pharmaceutical solids," Advanced drug delivery reviews, Feb. 2004, 56(3):275-300.
Office Action in Argentinian Application No. 20140101651, dated Sep. 22, 2023, 6 pages (with English Translation).
Office Action in Argentinian Application No. 20160100442, dated Feb. 23, 2024, 4 pages (with English Translation).
Office Action in Argentinian Application No. 20210101214, dated Sep. 22, 2023, 8 pages (with English Translation).
Office Action in Australian Application No. 2019262195, dated Aug. 29, 2023, 6 pages.
Office Action in Australian Application No. 2019262579, dated Sep. 1, 2023, 4 pages.
Office Action in Brazilian Application No. 112017017727-7, dated Jun. 28, 2023, 8 pages (with machine translation).
Office Action in Brazilian Application No. BR112020022392-1, dated Oct. 24, 2023, 7 pages (with English translation).
Office Action in Chilean Application No. 202201430, dated Feb. 2, 2024, 26 pages (with machine translation).
Office Action in Chilean Application No. 202202037, dated Jan. 30, 2024, 32 pages (with Machine Translation).
Office Action in Chilean Application No. 202202473, dated Jan. 29, 2024, 38 pages (with Machine Translation).
Office Action in Chinese Application No. 201980042915, dated Jul. 14, 2023, 9 pages (with English Translation).
Office Action in Chinese Application No. 201980042915X, dated Feb. 23, 2024, 4 pages (with English Translation).
Office Action in Chinese Application No. 201980042917.9, dated Aug. 31, 2023, 7 pages (with English Translation).
Office Action in Chinese Application No. 2019800429179, dated Mar. 2, 2024, 9 pages (with English Translation).
Office Action in Chinese Application No. 202080084260.5, dated Sep. 20, 2023, 30 pages (with English Translation).
Office Action in Chinese Application No. 202211353119.8, dated Dec. 21, 2023, 12 pages (with English Translation).
Office Action in Columbian Application No. NC2020/0015226, dated Oct. 6, 2023, 18 pages (with English Translation).
Office Action in Columbian Application No. NC2020/0015228, dated Nov. 22, 2023, 29 pages (with English Translation).
Office Action in Eurasian Application No. 202291810, dated Sep. 29, 2023, 8 pages (with English Translation).
Office Action in European Application No. 23197192.0, dated Sep. 29, 2023, 1 page.
Office Action in Indian Application No. 10665/DELNP/2014, dated Nov. 9, 2023, 3 pages.
Office Action in Indian Application No. 10665/DELNP/2014, dated Oct. 7, 2023, 3 pages.
Office Action in Indian Application No. 201918011571, dated Jan. 9, 2024, 8 pages.
Office Action in Israeli Application No. 278289, dated Aug. 31, 2023, 4 pages.
Office Action in Israeli Application No. 278413, dated Feb. 15, 2024, 4 pages.
Office Action in Japanese Application No. 2020-561731, dated Dec. 5, 2023, 6 pages (with English Translation).
Office Action in Japanese Application No. 2020-561741, dated Dec. 5, 2023, 5 pages (with English Translation).
Office Action in Korean Application No. 10-2020-7034837, dated Mar. 18, 2024, 14 pages (with English translation).
Office Action in Korean Application No. 10-2020-7034898, dated Mar. 20, 2024, 17 pages (with English translation).
Office Action in Malaysian Application No. PI2019006934, dated Oct. 16, 2023, 3 pages.
Office Action in Malaysian Application No. PI2020005647, dated Feb. 22, 2024, 4 pages.
Office Action in Mexican Application No. 2020/011639, dated Nov. 1, 2023, 7 pages (with Machine Translation).
Office Action in Mexican Application No. MX/a/2020/011718, dated Sep. 26, 2023, 15 pages (with English Translation).
Office Action in Mexican Application No. MX/a/2022/000517, dated Mar. 5, 2024, 8 pages (with English Translation).
Office Action in Peru Application No. 00866-2019/DIN, dated Jun. 28, 2023, 12 pages (with English Translation).
Office Action in Peru Application No. 2468-2019, dated Jan. 26, 2024, 26 pages (with English Translation).
Office Action in Philippines Application No. 1-2017-501483, dated Apr. 16, 2024, 5 pages.
Office Action in Philippines Application No. 1-2019-502675, dated Nov. 28, 2023, 6 pages.
Office Action in Philippines Application No. 1-2020-551843, dated Aug. 24, 2023, 7 pages.
Office Action in Philippines Application No. 1-2020-551843, dated Feb. 8, 2024, 5 pages.
Office Action in Thai Application No. 2001006317, dated Apr. 1, 2024, 10 pages (with English Translation).
Opposition in Indian Application No. 202017052853, dated Sep. 2, 2023, 1167 pages.
Parmar et al., "Hydrochloride salt co-crystals: preparation, characterization and physicochemical studies," Pharmaceutical Development and Technology, 2013, 18(2):443-453.
Peterson et al., "Expanding the Scope of Crystal Form Evaluation in Pharmaceutical Science," J Pharm Pharmaceut Sci., Feb. 2006, 9(3):317-326.
Philippines Office Action in Philippines Application No. 1-2020-551843, dated Jun. 27, 2024, 4 pages.
Pindelska et al., "Pharmaceutical cocrystals, salts and polymorphs: Advanced characterization techniques," Advanced Drug Delivery Reviews, 2017, 117:111-146.
Polymorphism in Pharmaceutical Solids, 2nd Ed., Brittain (ed)., 2009, 288-289.
Polymorphism in Pharmaceutical Solids, 2nd Ed., Brittain (ed)., 2009, pp. 2, 3, 15-19, 318-430.
Thakuria et al., "Crystal Polymorphism in Pharmaceutical Science," Comprehensive Supramolecular Chemistry II, Jun. 2017, vol. 5, chapter 22, pp. 283-309.

DERIVATIVES OF AN FGFR INHIBITOR

This application is a continuation of U.S. application Ser. No. 17/110,875, filed Dec. 3, 2020, which claims the benefit of priority of U.S. Prov. Appl. No. 62/943,406, filed Dec. 4, 2019, which is incorporated herein by reference in its entirety.

FIELD

This application relates to derivatives (e.g., hydroxyl, keto, glucuronide, sulfonic acid, and deuterated) of a Fibroblast Growth Factor Receptors (FGFR) inhibitor, including methods of preparation thereof, and intermediates in the preparation thereof, which are useful in the treatment of FGFR mediated disease such as cancer.

SEQUENCE LISTING

This application contains a Sequence Listing that has been submitted electronically as an XML file named "20443-0654002_SL_ST26.XML." The XML file, created on Jul. 21, 2022, is 2,258 bytes in size. The material in the XML file is hereby incorporated by reference in its entirety.

BACKGROUND

The Fibroblast Growth Factor Receptors (FGFR) are receptor tyrosine kinases that bind to fibroblast growth factor (FGF) ligands. There are four FGFR proteins (FGFR1-4) that are capable of binding ligands and are involved in the regulation of many physiological processes including tissue development, angiogenesis, wound healing, and metabolic regulation. Upon ligand binding, the receptors undergo dimerization and phosphorylation leading to stimulation of the protein kinase activity and recruitment of many intracellular docking proteins. These interactions facilitate the activation of an array of intracellular signaling pathways including Ras-MAPK, AKT-PI3K, and phospholipase C that are important for cellular growth, proliferation and survival (Reviewed in Eswarakumar et al. Cytokine & Growth Factor Reviews, 2005).

Aberrant activation of this pathway either through overexpression of FGF ligands or FGFR or activating mutations in the FGFRs can lead to tumor development, progression, and resistance to conventional cancer therapies. In human cancer, genetic alterations including gene amplification, chromosomal translocations and somatic mutations that lead to ligand-independent receptor activation have been described. Genetic alterations can include mutations, fusions, rearrangements (e.g., translocations, deletions, inversions) and amplification of genes. Large scale DNA sequencing of thousands of tumor samples has revealed that components of the FGFR pathway are among the most frequently mutated in human cancer. Many of these activating mutations are identical to germline mutations that lead to skeletal dysplasia syndromes. Mechanisms that lead to aberrant ligand-dependent signaling in human disease include overexpression of FGFs and changes in FGFR splicing that lead to receptors with more promiscuous ligand binding abilities (Reviewed in Knights and Cook Pharmacology & Therapeutics, 2010; Turner and Grose, Nature Reviews Cancer, 2010). Therefore, development of inhibitors targeting FGFR may be useful in the clinical treatment of diseases that have elevated FGF or FGFR activity.

The cancer types in which FGF/FGFRs are implicated include, but are not limited to: carcinomas (e.g., bladder, breast, cervical, colorectal, endometrial, gastric, head and neck, kidney, liver, lung, ovarian, prostate); hematopoietic malignancies (e.g., multiple myeloma, chronic lymphocytic lymphoma, adult T cell leukemia, acute myelogenous leukemia, non-Hodgkin lymphoma, myeloproliferative neoplasms, and Waldenstrom's Macroglubulinemia); and other neoplasms (e.g., glioblastoma, melanoma, and rhabdosarcoma). In addition to a role in oncogenic neoplasms, FGFR activation has also been implicated in skeletal and chondrocyte disorders including, but not limited to, achrondroplasia and craniosynostosis syndromes. The FGFR4-FGF19 signaling axis, specifically, has been implicated in the pathogenesis of a number of cancers including hepatocellular carcinoma (Heinzle et al., Cur. Pharm. Des. 2014, 20:2881). Ectopic expression of FGF19 in transgenic mice was shown to lead to tumor formation in the liver and a neutralizing antibody to FGF19 was found to inhibit tumor growth in mice. In addition, overexpression of FGFR4 has been observed in a multiple tumor types including hepatocellular carcinoma, colorectal, breast, pancreatic, prostate, lung, and thyroid cancers. Furthermore, activating mutations in FGFR4 have been reported in rhabdomyosarcoma (Taylor et al. JCI 2009, 119:3395).

Inhibitors of FGFR are currently being developed for the treatment of cancer. For example, the molecule 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one and other small molecule inhibitors of FGFR are reported in e.g., US Publication Nos.: 2012/0165305; 2014-0045814; 2013-0338134; 2014/0171405; 2014/0315902; 2016/0115164; 2016/0244448; 2016/0244449; and 2016-0244450.

Accordingly, new or improved agents which inhibit FGFR are continually needed for developing new and more effective pharmaceuticals to treat cancer and other diseases. The compounds including derivatives of these compounds, compositions and methods described herein are directed toward these needs and other ends.

SUMMARY

The present disclosure provides, inter alia, derivatives of Compound 1:

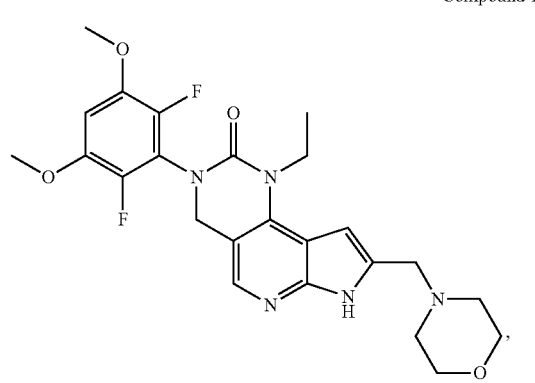

Compound 1 or a pharmaceutically acceptable salt thereof.

The present disclosure is further directed to pharmaceutical compositions comprising a compound of the disclosure, or a pharmaceutically acceptable salt thereof, and at least one pharmaceutically acceptable carrier.

The present disclosure is further directed to methods of inhibiting an FGFR enzyme comprising contacting the enzyme with a compound of the disclosure, or a pharmaceutically acceptable salt thereof.

The present disclosure is further directed to a method of treating a disease associated with abnormal activity or expression of an FGFR enzyme, comprising administering a compound of the disclosure, or a pharmaceutically acceptable salt thereof, to a patient in need thereof.

The present disclosure is further directed to compounds of the disclosure for use in treating a disease associated with abnormal activity or expression of an FGFR enzyme.

The present disclosure is further directed to a method for treating a disorder mediated by an FGFR enzyme, or a mutant thereof, in a patient in need thereof, comprising the step of administering to said patient a compound of the disclosure, or pharmaceutically acceptable composition thereof.

The present disclosure is further directed to a method for treating a disorder mediated by an FGFR enzyme, or a mutant thereof, in a patient in need thereof, comprising the step of administering to the patient a compound of the disclosure, or a pharmaceutically acceptable salt thereof, or a composition comprising a compound of the disclosure, or a pharmaceutically acceptable salt thereof, in combination with another therapy or therapeutic agent as described herein.

The present disclosure is further directed to the use of compounds of the disclosure in the preparation of a medicament for use in therapy.

DETAILED DESCRIPTION

Figure 1:
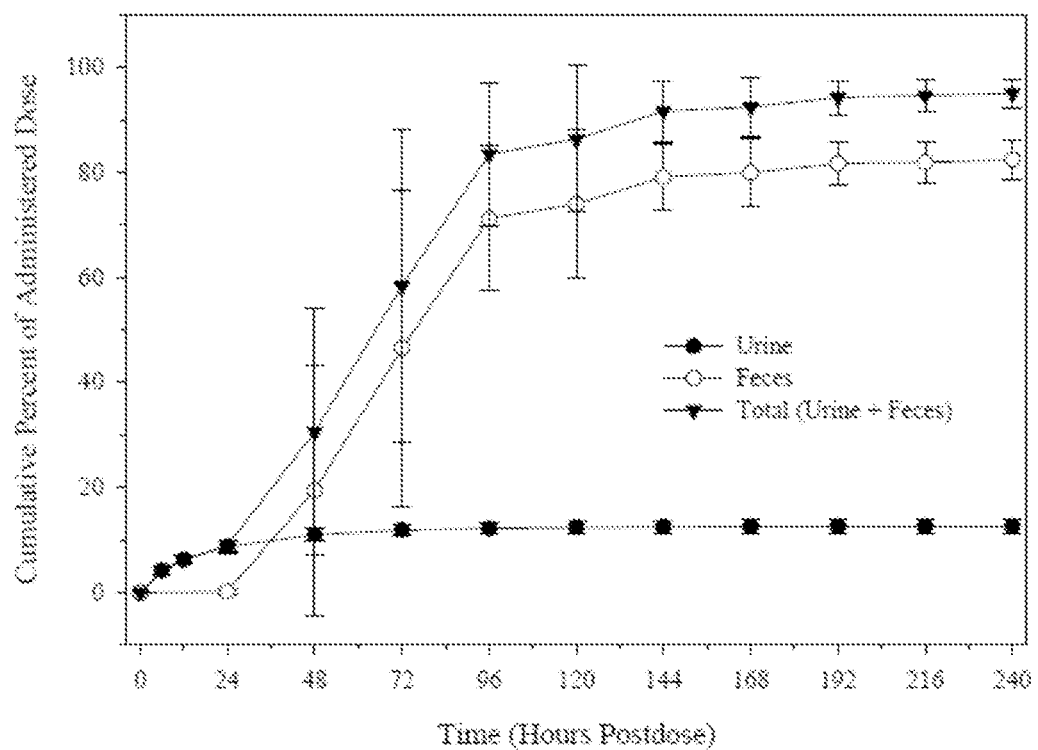
FIG. 1 is a graph showing the mean cumulative percent of radioactive dose recovered in urine and feces at specified intervals after a single 13-mg (250 µCi) oral dose of [14C] Compound 1 to healthy male subjects.

The present disclosure is directed to, inter alia, compounds that are derivatives of 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one (Compound 1), and processes and intermediates for preparing the derivatives. The structure of Compound 1 is shown below.

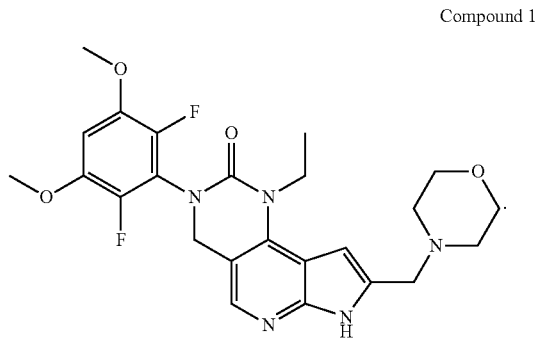 [SMILES: CCN1C(=O)N(c2c(F)c(OC)cc(OC)c2F)Cc2cnc3[nH]c(CN4CCOCC4)cc3c21]

Compound 1

Compound 1 is described in U.S. Pat. No. 9,611,267, the entirety of which is incorporated herein by reference.

In some embodiments, the compound is a metabolite of Compound 1. In some embodiments, the compound is an active metabolite which can modulate the activity of one or more FGFR proteins and can be useful, for example, in the treatment of diseases associated with FGFR expression or activity. In some embodiments, the level of a metabolite compound described herein is measured and profiled in order to aid a practitioner in the adjustment of dosage levels of Compound 1.

Accordingly, the present disclosure also provides a compound of Formula I:

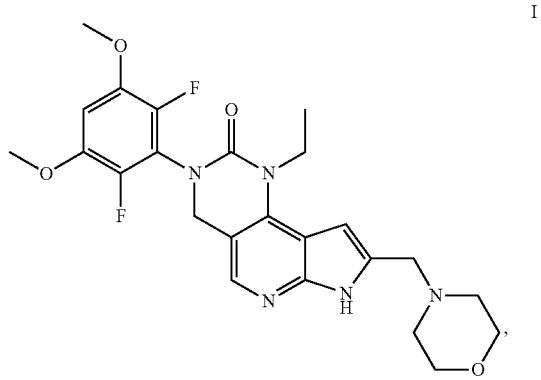 [SMILES: CCN1C(=O)N(c2c(F)c(OC)cc(OC)c2F)Cc2cnc3[nH]c(CN4CCOCC4)cc3c21]

I or a pharmaceutically acceptable salt thereof, wherein:
one or more OCH$_3$ groups are optionally replaced with an OH group, wherein the OH group is optionally replaced with an O—X group,
one C—H group is optionally replaced with a C—X group,
one CH$_2$ group is optionally replaced with a C═O group,
one or more CH$_2$ groups of the morpholine ring are each optionally replaced with a C(OH)H group,
the N—H group is optionally replaced with an N—X group, and wherein X is a group selected from:

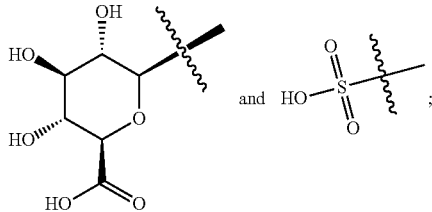

provided the compound has one or more of groups selected from OH, O—X, C—X, C=O, and N—X.

The present invention also provides a compound of Formula II:

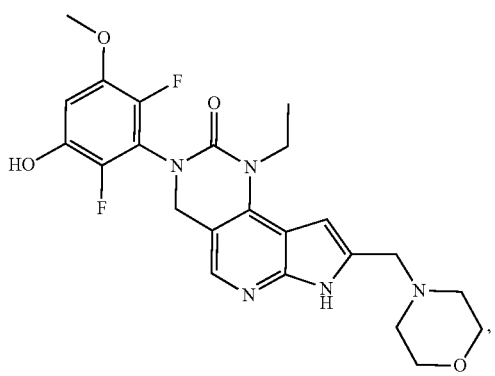

or a pharmaceutically acceptable salt thereof, wherein:

one C—H group is optionally replaced with a C—X group, one $CH_2$ group is optionally replaced with a C=O group, the N—H group is optionally replaced with an N—X group, and the O—H group is optionally replaced with an O—X group;

wherein X is a group selected from:

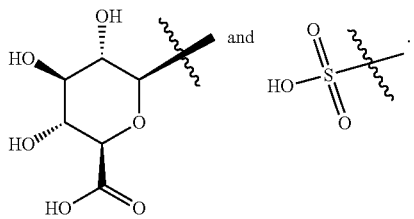

In some embodiments, the present invention also provides a compound of Formula II:

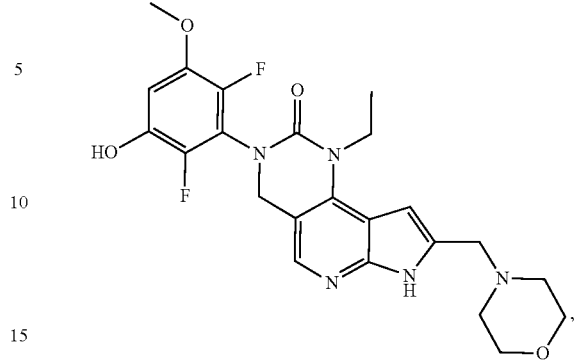

or a pharmaceutically acceptable salt thereof, wherein one C—H group is replaced with a C—X group, the N—H group is replaced with an N—X group, or the O—H group is replaced with an O—X group; wherein X is a group selected from:

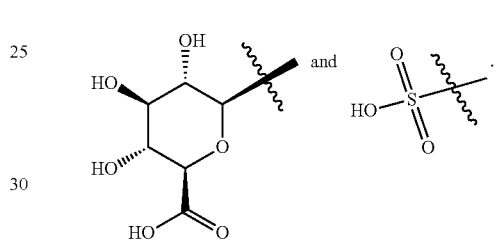

In some embodiments, one or more $OCH_3$ groups are optionally replaced with an OH group, wherein the OH group is optionally replaced with an O—X group. In some embodiments, the OH group is optionally replaced with an O—X group. In some embodiments, one C—H group is optionally replaced with a C—X group. In some embodiments, one $CH_2$ group is optionally replaced with a C=O group. In some embodiments, the N—H group is optionally replaced with an N—X group. In some embodiments, one or more $CH_2$ groups of the morpholine ring are each optionally replaced with a C(OH)H group In some embodiments, one or more $OCH_3$ groups are replaced with an OH group, wherein the OH group is replaced with an O—X group. In some embodiments, one or more $OCH_3$ groups are replaced with an OH group. In some embodiments, the OH group is replaced with an O—X group. In some embodiments, one C—H group is replaced with a C—X group. In some embodiments, one $CH_2$ group is replaced with a C=O group. In some embodiments, the N—H group is replaced with an N—X group. In some embodiments, one or more $CH_2$ groups of the morpholine ring are each replaced with a C(OH)H group.

In some embodiments, X is

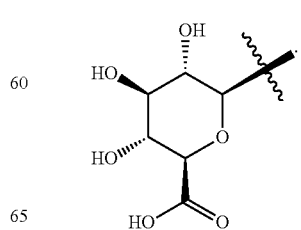

In some embodiments, X is

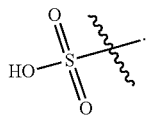

The present invention provides a compound which is 3-(2,6-difluoro-3-hydroxy-5-methoxyphenyl)-1-ethyl-8-(morpholinomethyl)-1,3,4,7-tetrahydro-2H-pyrrolo[3',2':5,6]pyrido[4,3-d]pyrimidin-2-one (Compound 2), or a pharmaceutically acceptable salt thereof. The structure of Compound 2 is shown below:

Compound 2

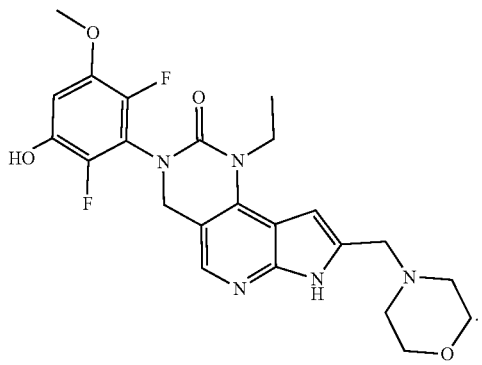

The present invention also provides a compound which is 3-(2,6-difluoro-3,5-dimethoxyphenyl)-1-ethyl-4-hydroxy-8-(morpholinomethyl)-1,3,4,7-tetrahydro-2H-pyrrolo[3',2':5,6]pyrido[4,3-d]pyrimidin-2-one (Compound 3), or a pharmaceutically acceptable salt thereof. The structure of Compound 3 is shown below:

Compound 3

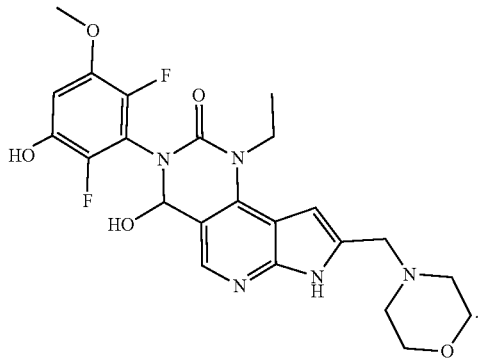

The present invention also provides a compound which is 3-(2,6-difluoro-3,5-dihydroxyphenyl)-1-ethyl-8-(morpholinomethyl)-1,3,4,7-tetrahydro-2H-pyrrolo[3',2':5,6]pyrido[4,3-d]pyrimidin-2-one (Compound 4), or a pharmaceutically acceptable salt thereof. The structure of Compound 4 is shown below:

Compound 4

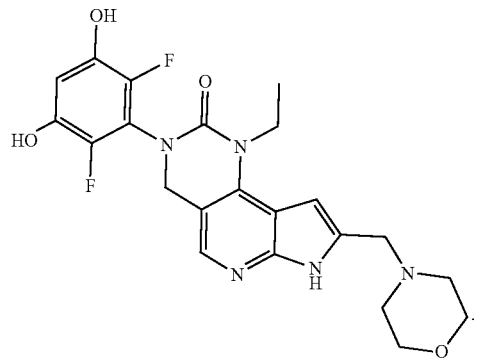

In some embodiments, the compound is selected from:
3-(2,6-difluoro-3-hydroxy-5-methoxyphenyl)-1-ethyl-8-(morpholinomethyl)-1,3,4,7-tetrahydro-2H-pyrrolo[3',2':5,6]pyrido[4,3-d]pyrimidin-2-one; and 3-(2,6-difluoro-3,5-dimethoxyphenyl)-1-ethyl-4-hydroxy-8-(morpholinomethyl)-1,3,4,7-tetrahydro-2H-pyrrolo[3',2':5,6]pyrido[4,3-d]pyrimidin-2-one, or a pharmaceutically acceptable salt thereof.

In some embodiments, the compound is a compound of Formula I:

I

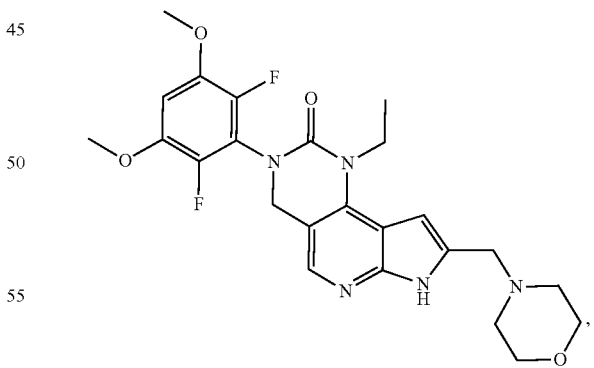

or a pharmaceutically acceptable salt thereof, wherein one $CH_2$ group of the morpholine ring is replaced with a (C=O) group.

In some embodiments, the compound is a compound of Formula II:

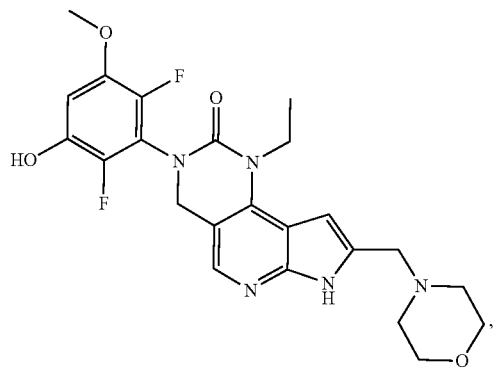
II

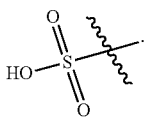

In some embodiments, the compound is a compound of Formula I:

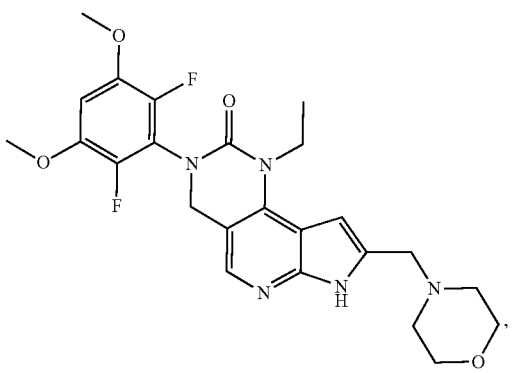
I or a pharmaceutically acceptable salt thereof, wherein one C—H group is replaced with a C—X group, the N—H group is replaced with an N—X group, or the O—H group is replaced with an O—X group; wherein X is the following group:

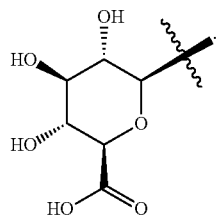

or a pharmaceutically acceptable salt thereof, wherein two CH$_2$ groups of the morpholine ring are each replaced with a C(OH)H group.

In some embodiments, the compound is a compound of Formula I:

In some embodiments, the compound is a compound of Formula II:

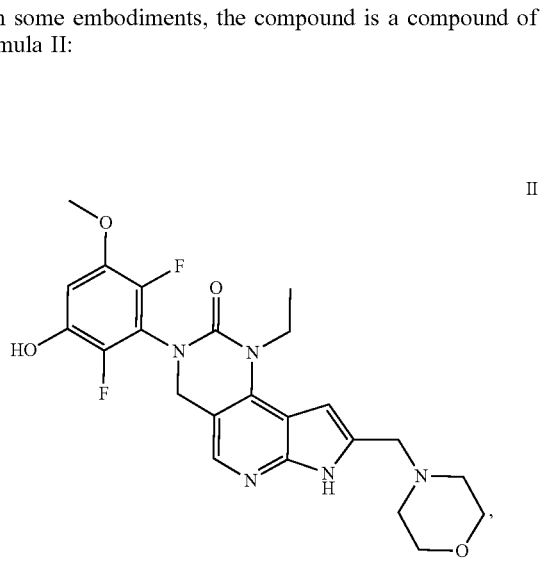
II

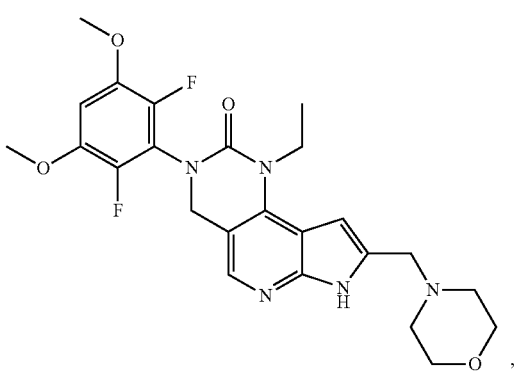
I or a pharmaceutically acceptable salt thereof, wherein one C—H group is replaced with a C—X group, the N—H group is replaced with an N—X group, or the O—H group is replaced with an O—X group; wherein X is the following group:

or a pharmaceutically acceptable salt thereof, wherein each OCH$_3$ group is replaced with an OH group; and one CH$_2$ group of the morpholine ring is replaced with a (C═O) group.

In some embodiments, the compound is a compound of Formula II:

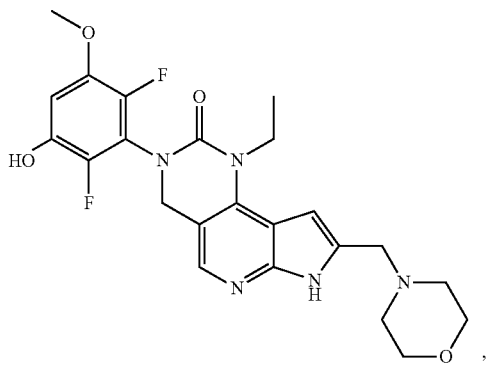

or a pharmaceutically acceptable salt thereof, wherein one CH$_2$ group of the morpholine ring is replaced with a (C=O) group.

Also provided herein is a compound which is 3-(2,6-difluoro-3-hydroxy-5-methoxyphenyl)-1-ethyl-2-oxo-2,3,4,7-tetrahydro-1H-pyrrolo[3',2':5,6]pyrido[4,3-d]pyrimidine-8-carboxylic acid (Compound 5), or a pharmaceutically acceptable salt thereof. The structure of Compound 5 is shown below:

Compound 5

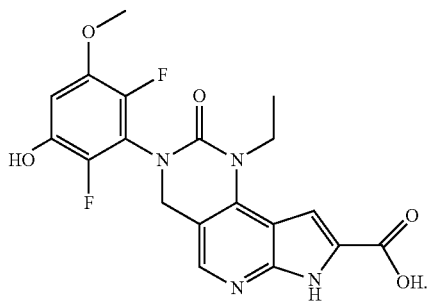

Also provided herein is a compound which is 3-(2,6-difluoro-3,5-bis(methoxy-d3)phenyl)-1-ethyl-8-(morpholinomethyl)-1,3,4,7-tetrahydro-2H-pyrrolo[3',2':5,6]pyrido[4,3-d]pyrimidin-2-one (Compound 6), or a pharmaceutically acceptable salt thereof. The structure of Compound 6 is shown below:

Compound 6

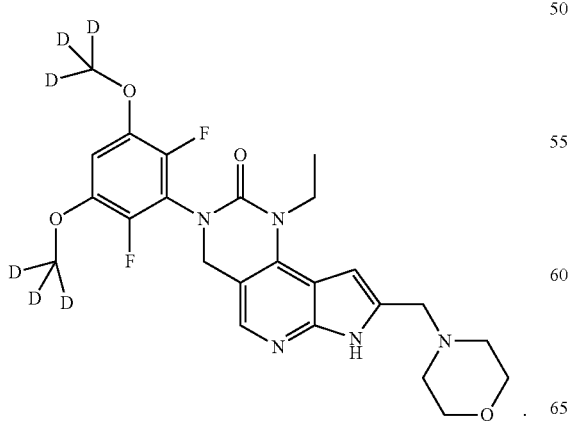

Each of the aforementioned embodiments assumes that the rules for proper valency are adhered to.

Certain compounds described herein are metabolites of 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one (Compound 1). The metabolites were isolated from human blood/serum, urine, and feces samples collected from pharmacokinetic and toxicokinetic studies of Compound 1. Metabolites of the invention may be FGFR inhibitors, and can have advantageous properties (PK, PD, toxicity, etc.) compared to the parent compound (Compound 1). For example, metabolites of the disclosure (e.g., Compound 2) may be better substrates for Pgp transport compared to Compound 1. Thus, metabolites of the disclosure (e.g., Compound 2) may be more suitable candidates for intravenous administration or hepatic arterial infusion for the treatment of diseases and disorders disclosed herein (e.g., cholangiocarcinoma).

In some embodiments, the compounds of the invention are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the metabolite.

Also provided herein is a composition comprising a compound of the disclosure, or a pharmaceutically acceptable salt thereof, containing at least about 50% by weight of the compound or salt. In some embodiments, the composition contains at least about 60% by weight of the compound or salt. In some embodiments, the composition contains at least about 70% by weight of the compound or salt. In some embodiments, the composition contains at least about 80% by weight of the compound or salt. In some embodiments, the composition contains at least about 90% by weight of the compound or salt.

Process for Preparation of Compound 2

The present application further provides a process of preparing Compound 2, where the process can be suitable for scale up.

Provided herein is a process of preparing Compound 2 having the formula:

Compound 2

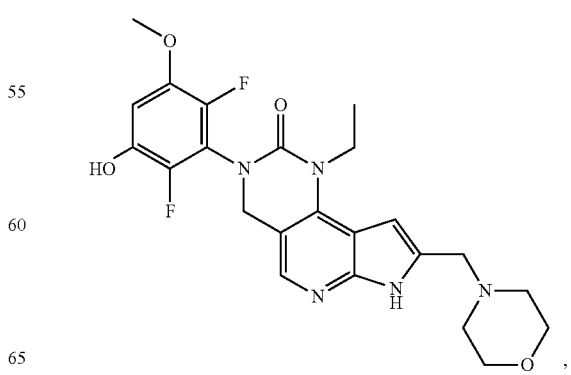

or a salt thereof, comprising deprotecting Compound F4 having the formula:

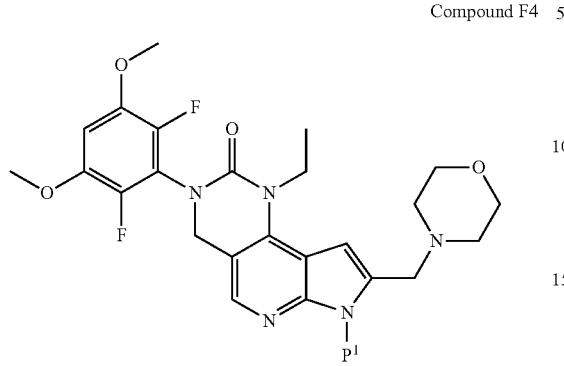

Compound F4 or a salt thereof, wherein $P^1$ is an amino protecting group. In some embodiments, $P^1$ is an sulfonamide group. In some embodiments, $P^1$ is —$SO_2N(CH_3)_2$.

In some embodiments, the deprotecting of Compound F4 comprises reacting Compound F4 with A1, wherein A1 is an acid. In some embodiments, A1 is hydrochloric acid. In some embodiments, A1 is aqueous hydrochloric acid. In some embodiments, the deprotection is carried out at a temperature of 70-90° C. (e.g., 80° C.). In some embodiments, the deprotection is carried out in the presence of S1, wherein S1 is a polar aprotic solvent. In some embodiments, S1 is 1,4-dioxane. In some embodiments, the deprotecting of Compound F4 comprises using about 1 to about 50 molar equivalents of the deprotecting agent relative to Compound F4, about 10 to about 30 molar equivalents of the deprotecting agent relative to Compound F4, or about 20 molar equivalents of the deprotecting agent relative to Compound F4.

Compound F4, or a salt thereof, can be produced by a process comprising reacting Compound F3 having the formula:

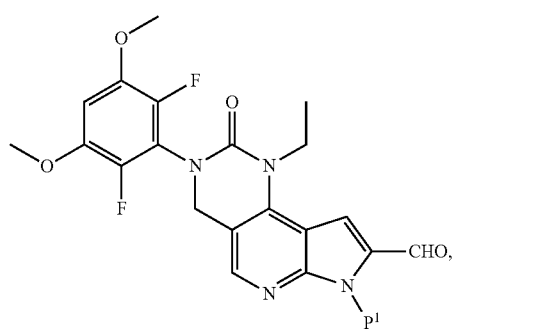

Compound F3 or a salt thereof, with morpholine in the presence of RA1, wherein RA1 is a reducing agent. In some embodiments, RA1 is sodium triacetoxyborohydride. In some embodiments, the reacting of Compound F3 with RA1 is carried out in the presence of A2, wherein A2 is an acid. In some embodiments, A2 is an organic acid. In some embodiments, A2 is acetic acid. In some embodiments, the reacting of Compound F3 with RA1 is carried out in the presence of S2, wherein S2 is a solvent. In some embodiments, S2 is a polar aprotic solvent. In some embodiments, S2 is methylene chloride.

Compound F3, or a salt thereof, can be produced by a process comprising reacting Compound F2 having the formula:

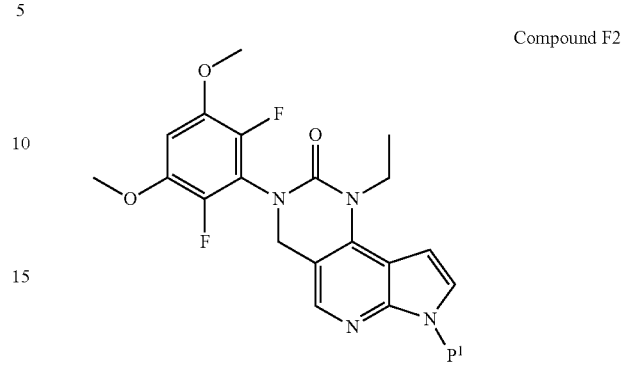

Compound F2 or a salt thereof, with DMF in the presence of B1, wherein B1 is a base. In some embodiments, B1 is lithium diisopropyl amide ("LDA"). In some embodiments, the reaction of Compound F2 with DMF in the presence of B1 is carried out in the presence of S3, wherein S3 is a polar aprotic solvent. In some embodiments, S3 is tetrahydrofuran. The reaction of Compound F2 with DMF in the presence of B1 can be carried out at a temperature between about −100° C. and about −50° C. (e.g., about −64° C.).

Compound F2, or a salt thereof, can be produced by a process comprising reacting Compound F1 having the formula:

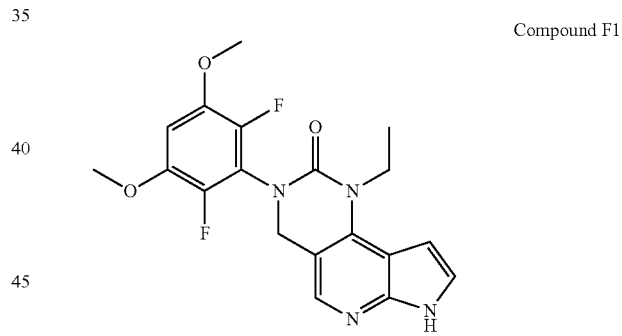

Compound F1 or a salt thereof, with an amino protecting agent comprising $P^1$.

In some embodiments, the amino protecting agent is $P^1$—X, where in X is a halogen. In some embodiments, the amino protecting agent is $Me_2NSO_2Cl$. The reacting of Compound F1 with the amino protecting agent can be performed in the presence of B2, wherein B2 is a base. In some embodiments, B2 is a metal hydroxide base. In some embodiments, B2 is NaOH.

The reacting of Compound F1 with an amino protecting agent can be performed in the presence of tetrabutylammonium hydrogensulfate. In some embodiments, the reacting of Compound F1 with the amino protecting agent is carried out in the presence of S4, wherein S4 is a polar aprotic solvent. In some embodiments, S4 is tetrahydrofuran. In some embodiments, the reacting of Compound F1 with the amino protecting agent is performed at a temperature from about 0° C. to about 50° C. (e.g., about 0° C. to about 30° C.).

Provided herein is a process of preparing Compound 2 having the formula:

Compound 2

[structure of Compound 2]

or a salt thereof, comprising:

a) reacting Compound F1 having the formula:

Compound F1

[structure of Compound F1]

with an amino protecting agent comprising P¹, to provide Compound F2 having the formula:

Compound F2

[structure of Compound F2]

or a salt thereof, wherein P¹ is an amino protecting group;

b) reacting Compound F2 with DMF in the presence of B1, wherein B1 is a base, to provide Compound F3 having the formula:

Compound F3

[structure of Compound F3]

or a salt thereof, c) reacting Compound F3 with morpholine in the presence of RA1, wherein RA1 is a reducing agent, to provide Compound F4 having the formula:

Compound F4

[structure of Compound F4]

or a salt thereof, and d) deprotecting Compound F4 to provide Compound 2, or a salt thereof.

Process for Preparation of Compound 6

The present disclosure provides a process of preparing Compound 6 having the formula:

Compound 6

[structure of Compound 6]

or a salt thereof, comprising deprotecting Compound F5 having the formula:

Compound F5

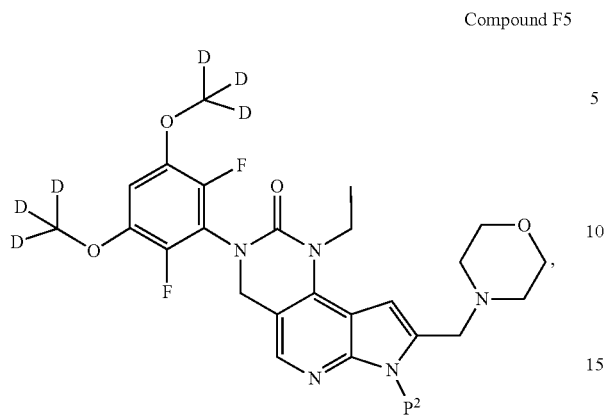

or a salt thereof, wherein P² is an amino protecting group. In some embodiments, P² is —SO²-phenyl.

The deprotecting of Compound F5 can comprise treating Compound F5 with B3, wherein B3 is a base. In some embodiments, B3 is a metal hydroxide base. In some embodiments, B3 is NaOH. In some embodiments, B3 is aqueous NaOH. In some embodiments, the deprotecting of Compound F5 is performed in the presence of S5, wherein S5 is 1,4-dioxane. In some embodiments, the reacting of Compound F5 with B3 comprises using about 1 to about 10 molar equivalents of B3 relative to Compound F5, about 2 to about 8 molar equivalents of B3 relative to Compound F5, or about 4 molar equivalents of B3 relative to Compound F5.

Compound F5 can be prepared by a process comprising reacting Compound F6 having the formula:

Compound F6

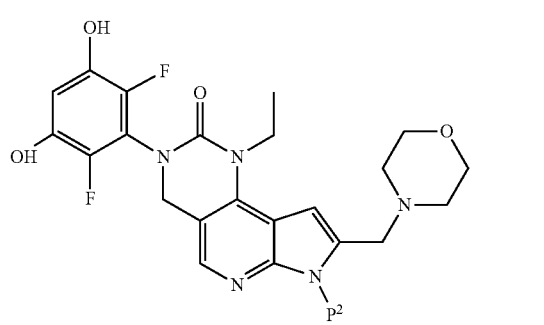

with CD₃I in the presence of B4, wherein B4 is a base. In some embodiments, B4 is sodium hydride.

The reacting of Compound F6 with CD₃I can be performed in the presence of S6, wherein S6 is a polar aprotic solvent. In some embodiments, S6 is DMF. The reacting of Compound F6 with CD₃I can comprise using about 1 to about 5 molar equivalents of CD₃I relative to Compound F6, about 1 to about 3 molar equivalents of CD₃I relative to Compound F6, or about 2 molar equivalents of CD₃I relative to Compound F6. The reacting of Compound F6 with CD₃I can comprise using about 1 to about 10 molar equivalents of B4 relative to Compound F6, about 2 to about 8 molar equivalents of B4 relative to Compound F6, or about 4 to about 5 molar equivalents of B4 relative to Compound F6.

Compound F6 can be prepared by a process comprising reacting Compound F7 having the formula:

Compound F7

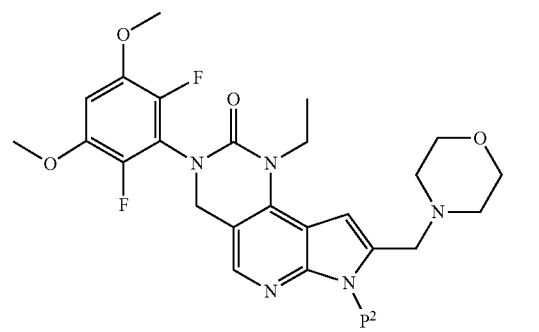

with A3, wherein A3 is a Lewis acid. In some embodiments, A3 is BBr₃.

The reacting of Compound F7 with A3 can be performed in the presence of S7, wherein S7 is a polar aprotic solvent. In some embodiments, S7 is methylene chloride. The reacting of Compound F7 with A3 can be performed at a temperature from about −100° C. to about 30° C. (e.g., from about −100° C. to room temperature). The reacting of Compound F7 with A3 can comprise using about 1 to about 20 molar equivalents of A3 relative to Compound F7, about 5 to about 15 molar equivalents of A3 relative to Compound F7, or about 8 to about 12 molar equivalents of A3 relative to Compound F7.

Provided herein is a process for preparing Compound 6 having the formula:

Compound 6

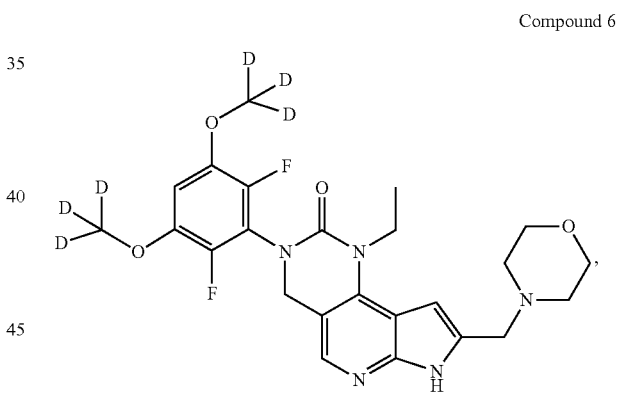

or a salt thereof, comprising:
a) reacting Compound F7 having the formula:

Compound F7

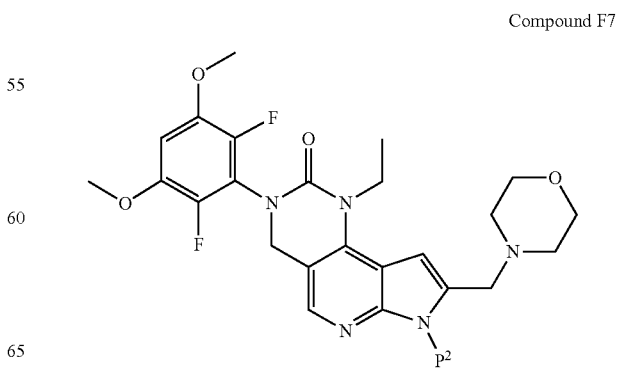

with A3, wherein A3 is a Lewis acid, and wherein $P^2$ is an amino protecting group, to provide Compound F6 having the formula:

Compound F6

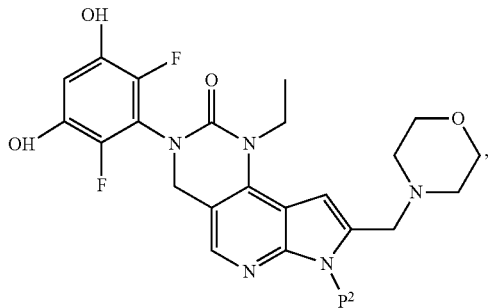

or a salt thereof,
b) reacting Compound F6 with $CD_3I$ in the presence of B4, wherein B4 is a base, to provide Compound F5 having the formula:

Compound F5

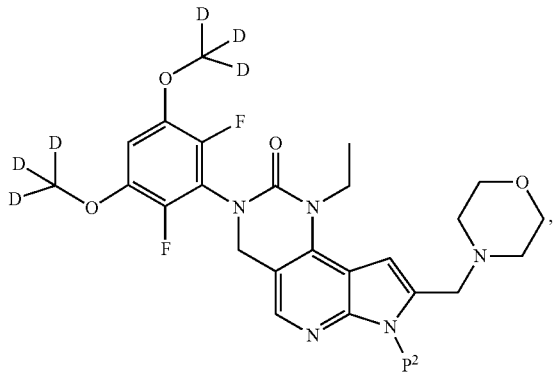

or a salt thereof, and
c) deprotecting Compound F5 to provide Compound 6, or a salt thereof.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry; or by chromatography such as high performance liquid chromatography (HPLC) or thin layer chromatography. The compounds obtained by the reactions can be purified by any suitable method known in the art. For example, chromatography (medium pressure) on a suitable adsorbent (e.g., silica gel, alumina and the like), HPLC, or preparative thin layer chromatography; distillation; sublimation; trituration, or recrystallization. The purity of the compounds, in general, are determined by physical methods such as measuring the melting point (in case of a solid), obtaining a NMR spectrum, or performing a HPLC separation. If the melting point decreases, if unwanted signals in the NMR spectrum are decreased, or if extraneous peaks in an HPLC trace are removed, the compound can be said to have been purified. In some embodiments, the compounds are substantially purified.

Preparation of compounds can involve the protection and deprotection of various chemical groups. The need for protection and deprotection, and the selection of appropriate protecting groups can be readily determined by one skilled in the art. The chemistry of protecting groups can be found, for example, in Wuts and Greene, *Greene's Protective Groups in Organic Synthesis*, $4^{th}$ Ed., John Wiley & Sons: New York, 2006, which is incorporated herein by reference in its entirety. As used herein, "amino protecting group" refers to any protecting group for the protection of amines. Example amino protecting groups include, but are not limited to, phenylsulfonyl, benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl)ethoxycarbonyl (Tsc), t-butoxycarbonyl (BOC), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBOC), vinyl, 2-chloroethyl, 2-phenylsulfonylethyl, allyl, benzyl, 2-nitrobenzyl, 4-nitrobenzyl, diphenyl-4-pyridylmethyl, N',N'-dimethylhydrazinyl, methoxymethyl, t-butoxymethyl (Bum), benzyloxymethyl (BOM), or 2-tetrahydropyranyl (THP), tri($C_{1-4}$ alkyl)silyl (e.g., tri(isopropyl)silyl), 1,1-diethoxymethyl, or N-pivaloyloxymethyl (POM).

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

In some embodiments, concentrating a solution as described herein refers to a solution where its volume is reduced by letting the solvent evaporate, by heating the solution, by subjecting the solution to reduced pressure, or any combination thereof.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

Suitable solvents can include halogenated solvents such as carbon tetrachloride, bromodichloromethane, dibromochloromethane, bromoform, chloroform, bromochloromethane, dibromomethane, butyl chloride, dichloromethane (methylene chloride), tetrachloroethylene, trichloroethylene, 1,1,1-trichloroethane, 1,1,2-trichloroethane, 1,1-dichloroethane, 2-chloropropane, α,α,α-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable ether solvents include: dimethoxymethane, tetrahydrofuran, 1,3-dioxane, 1,4-dioxane, furan, tetrahydrofuran (THF), diethyl ether, ethylene glycol dimethyl ether, ethylene glycol diethyl ether, diethylene glycol dimethyl ether (diglyme), diethylene glycol diethyl ether, triethylene glycol dimethyl ether, anisole, tert-butyl methyl ether, mixtures thereof and the like.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, iso-butyl alcohol, tert-butyl alcohol, 2-ethoxyethanol, diethylene glycol, 1-, 2-, or 3-pentanol, neo-pentyl alcohol, tert-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

The reactions of the processes described herein can be carried out in air or under an inert atmosphere. Typically, reactions containing reagents or products that are substantially reactive with air can be carried out using air-sensitive synthetic techniques that are well known to the skilled artisan.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C. The term "elevated temperature" as used herein, is understood in the art, and refer generally to a temperature, e.g., a reaction temperature, that is above room temperature, e.g., above 30° C.

Provided herein is Compound F2:

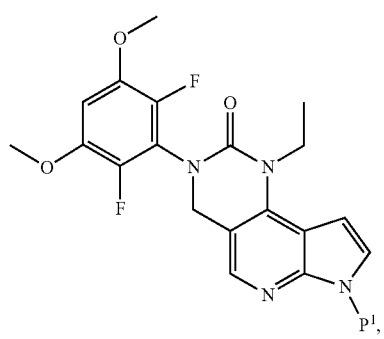

or a salt thereof, wherein P¹ is an amino protecting group.

In some embodiments, Compound F2 has the following structure:

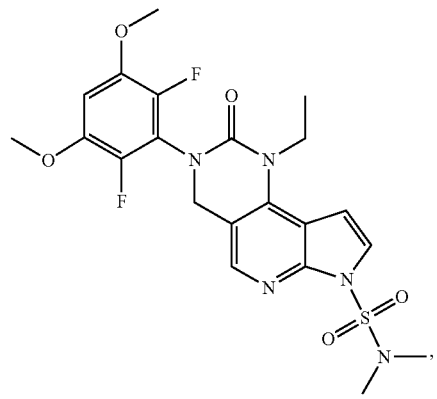

or a salt thereof.

Provided herein is Compound F3:

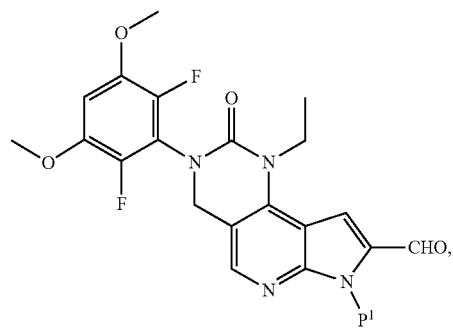

or a salt thereof, wherein P¹ is an amino protecting group.

In some embodiments, Compound F3 has the following structure:

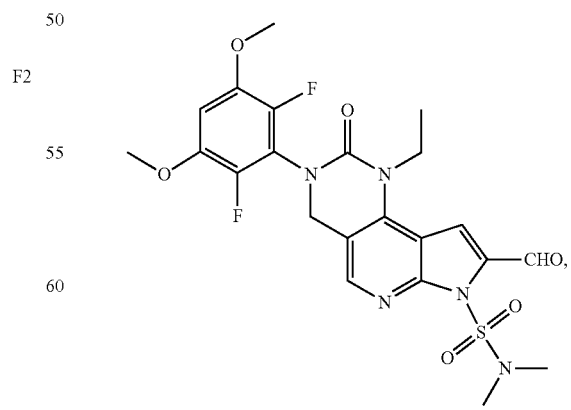

or a salt thereof.

Provided herein is Compound F4:

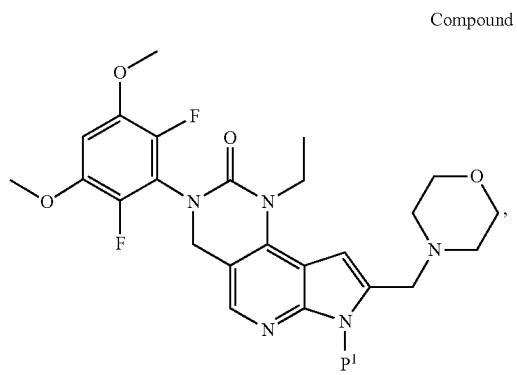

Compound F4 or a salt thereof, wherein P¹ is an amino protecting group.

In some embodiments, Compound F4 has the following structure:

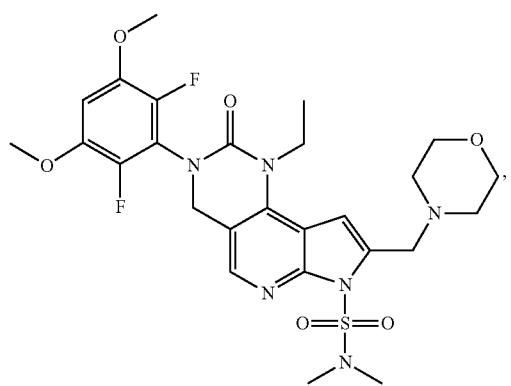 [SMILES: CCN1C(=O)N(c2c(F)c(OC)cc(OC)c2F)Cc2cnc3c(cc(CN4CCOCC4)n3S(=O)(=O)N(C)C)c21]

or a salt thereof.

Provided herein is Compound F5:

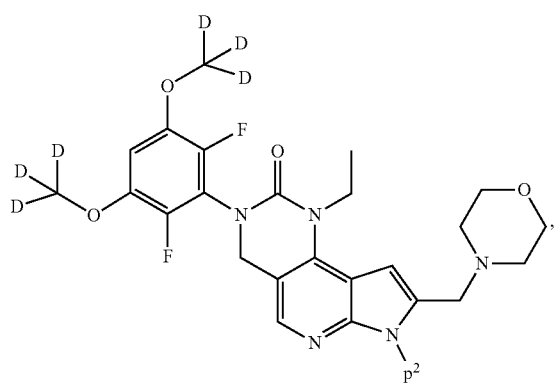

Compound F5 or a salt thereof, wherein P² is an amino protecting group.

In some embodiments, Compound F5 has the following structure:

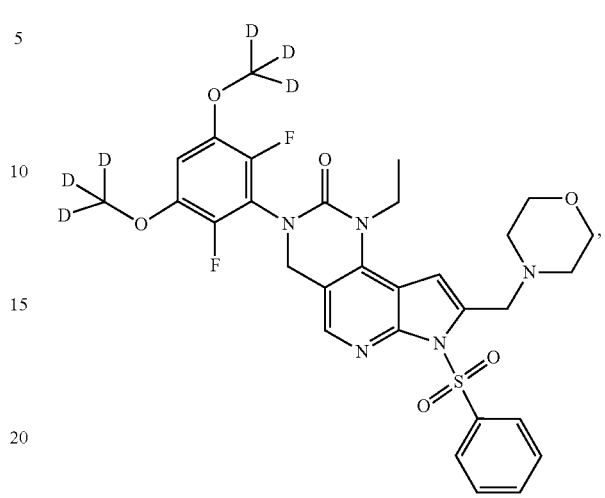

or a salt thereof.

Provided herein is Compound F6:

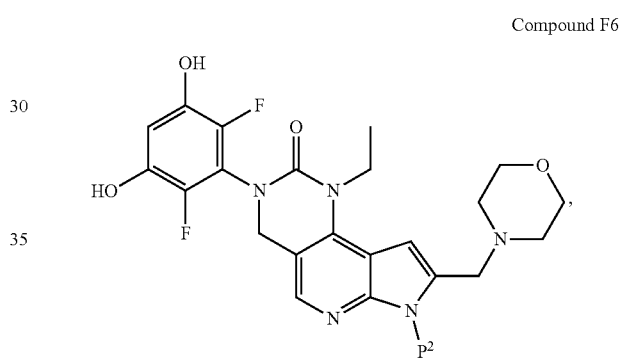

Compound F6 or a salt thereof, wherein P² is an amino protecting group.

In some embodiments, Compound F6 has the following structure:

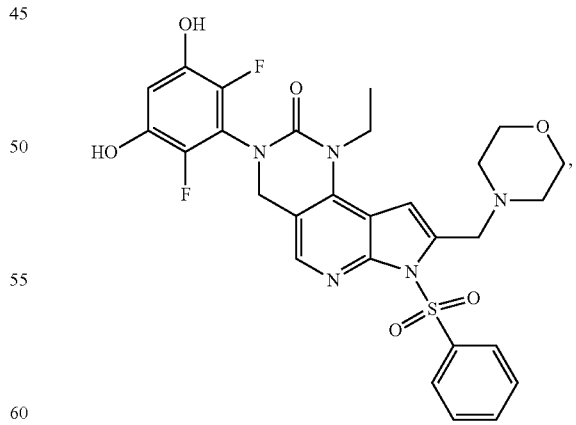

or a salt thereof.

Compounds of the disclosure also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the disclosure also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the disclosure can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd Radiopharm.* 2015, 58, 308-312).

The term, "compound," as used herein is meant to include all stereoisomers, geometric isomers, tautomers, and isotopes of the structures depicted. The term is also meant to refer to compounds of the disclosure, regardless of how they are prepared, e.g., synthetically, through biological process (e.g., metabolism or enzyme conversion), or a combination thereof.

Methods of Use

The compounds described herein can inhibit the activity of the FGFR enzyme. For example, the compounds of the disclosure can be used to inhibit activity of an FGFR enzyme in a cell or in an individual or patient in need of inhibition of the enzyme by administering an inhibiting amount of the compound to the cell, individual, or patient.

As FGFR inhibitors, the compounds of the disclosure are useful in the treatment of various diseases associated with abnormal expression or activity of the FGFR enzyme or FGFR ligands. Compounds which inhibit FGFR will be useful in providing a means of preventing the growth or inducing apoptosis in tumors, particularly by inhibiting angiogenesis. It is therefore anticipated that the compounds of the disclosure will prove useful in treating or preventing proliferative disorders such as cancers. In particular tumors with activating mutants of receptor tyrosine kinases or upregulation of receptor tyrosine kinases may be particularly sensitive to the inhibitors.

In certain embodiments, the disclosure provides a method for treating a FGFR-mediated disorder in a patient in need thereof, comprising the step of administering to said patient a compound of the disclosure, or a pharmaceutically acceptable composition thereof.

For example, the compounds of the disclosure are useful in the treatment of cancer. Example cancers include bladder cancer, breast cancer (e.g., hormone R positive, triple negative), cervical cancer, colorectal cancer, cancer of the small intestine, colon cancer, rectal cancer, cancer of the anus, endometrial cancer, gastric cancer (e.g., gastrointestinal stromal tumors), head and neck cancer (e.g., cancers of the larynx, hypopharynx, nasopharynx, oropharynx, lips, and mouth, squamous head and neck cancers), kidney cancer (e.g., renal cell carcinoma, urothelial carcinoma, sarcoma, Wilms tumor), liver cancer (e.g., hepatocellular carcinoma, cholangiocellular carcinoma, liver angiosarcoma, hepatoblastoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, vulvar cancer, esophageal cancer, gall bladder cancer, pancreatic cancer (e.g. exocrine pancreatic carcinoma), stomach cancer, thyroid cancer, parathyroid cancer, neuroendocrine cancer (e.g., pheochromocytoma, Merkel cell cancer, neuroendocrine carcinoma), skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors).

Further example cancers include hematopoietic malignancies such as leukemia or lymphoma, multiple myeloma, chronic lymphocytic lymphoma, adult T cell leukemia, B-cell lymphoma, cutaneous T-cell lymphoma, acute myelogenous leukemia, Hodgkin's or non-Hodgkin's lymphoma, myeloproliferative neoplasms (e.g., 8p11 myeloproliferative syndrome, polycythemia vera, essential thrombocythemia, and primary myelofibrosis), myelodysplastic syndrome, chronic eosinophilic leukemia, Waldenstrom's Macroglubulinemia, hairy cell lymphoma, chronic myelogenic lymphoma, acute lymphoblastic lymphoma, AIDS-related lymphomas, and Burkitt's lymphoma.

In certain embodiments, provided herein is a method of treating myeloid/lymphoid neoplasms in a patient in need thereof. In certain embodiments, the myeloid/lymphoid neoplasms are 8p11 myeloproliferative syndrome. As used herein, the term "8p11 myeloproliferative syndrome" (EMS) is meant to refer to myeloid/lymphoid neoplasms associated with eosinophilia and abnormalities of FGFR1 or myeloid/lymphoid neoplasms (MLN) with FGFR1 rearrangement. Eight P eleven myeloproliferative syndrome is reviewed in Jackson, Courtney C., et. al. *Human Pathology,* 2010, 41, 461-476. The defining feature of EMS is the presence of a translocation involving FGFR1 gene located on the chromosome 8p11 locus, and at least 10 additional translocations and 1 insertion have been identified in EMS, each disrupting FGFR1 and creating novel fusion genes with various partners. See Jackson, Courtney C., et. al. *Human Pathology,* 2010, 41, 461-476.

In some embodiments, the myeloid/lymphoid neoplasm is characterized by FGF/FGFR genetic alteration. Genetic alterations can include mutations, fusions, rearrangements (e.g., translocations, deletions, inversions) and amplification of genes. In certain embodiments, the myeloid/lymphoid neoplasm exhibits FGFR1 fusion. The FGFR1 fusion can be a translocation, interstitial deletion, or a chromosomal inversion. In some embodiments, the FGFR1 fusion is an FGFR1 translocation. In certain embodiments, the myeloid/lymphoid neoplasm exhibits an 8p11 translocation. In certain embodiments, the 8p11 translocation is associated with activation of FGFR1. In some embodiments, the myeloid/lymphoid neoplasm exhibits FGF/FGFR alterations other than FGFR1 translocations. In certain embodiments, the patient has failed at least one previous treatment for myeloid/lymphoid neoplasms (e.g., 8p11 myeloproliferative syndrome). In some embodiments, the previous treatment is surgery or radiation therapy. In some embodiments, the patient has a history of hepatitis. In some embodiments, the hepatitis is chronic hepatitis B or hepatitis C. In some embodiments, the patient does not have a history of hepatitis.

In certain embodiments, provided herein is a method of treating cancer comprising administering to a patient in need thereof a therapeutically effect amount of a compound of the disclosure. In certain embodiments, the cancer is selected from bladder cancer, breast cancer, cervical cancer, cancer of the small intestine, colorectal cancer, endometrial cancer, gastric cancer, head and neck cancer, kidney cancer, liver cancer, lung cancer, ovarian cancer, prostate cancer, testicular cancer, uterine cancer, vulvar cancer, esophageal cancer, gall bladder cancer, pancreatic cancer, thyroid cancer, skin cancer, brain cancer, leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's Macroglublulinemia, myeloproliferative neoplasms, chronic myelogenic lymphoma, acute lymphoblastic lymphoma, T lymphoblastic lymphoma, hairy cell lymphoma, Burkett's lymphoma, glioblastoma, melanoma, rhabdosarcoma, lymphosarcoma, and osteosarcoma.

In certain embodiments, the cancer is bladder cancer (e.g., urothelial carcinoma, squamous cell carcinoma, adenocarcinoma).

In certain embodiments, the liver cancer is cholangiocellular carcinoma (e.g., intrahepatic, hilar or perihilar, distal extrahepatic). As used herein, cholangiocellular carcinoma is the same as cholangiocarcinoma or bile duct cancer. In certain embodiments, the cholangiocarcinoma is advanced or metastatic cholangiocarcinoma. In certain embodiments, the cholangiocarcinoma is surgically unresectable. In certain embodiments, the cholangiocarcinoma is intrahepatic. In certain embodiments, the cholangiocarcinoma is extrahepatic. In certain embodiments, the cholangiocarcinoma exhibits FGFR2 tyrosine kinase fusions which define a certain molecular subtype as described in Arai, Yasuhito, et. al. *Hepatology*, 2014, 59, 1427-1434. In some embodiments, the cholangiocarcinoma is characterized by FGF/FGFR genetically altered tumors. In some embodiments, the tumors exhibit FGFR2 fusions. The FGFR2 fusion can be a translocation, interstitial deletion, or a chromosomal inversion. In some embodiments, the FGFR2 fusion is an FGFR2 translocation. The FGFR2 translocations can be selected from a group including, but not limited to, FGFR2-BICC1, FGFR2-AHCYL1, FGFR2-MACF1, FGFR2 intron 17 rearrangement. In some embodiments, the tumor exhibits FGF/FGFR alterations other than FGFR2 translocations. In some embodiments, the cholangiocarcinoma does not exhibit FGF/FGFR genetically altered tumors.

Other cancers treatable with the compounds of the disclosure include tumors of the eye, glioblastoma, melanoma, rhabdosarcoma, lymphosarcoma, leiomyosarcoma, urothelial carcinoma (e.g., ureter, urethra, bladder, urachus), and osteosarcoma.

The compounds of the disclosure can also be useful in the inhibition of tumor metastases.

In some embodiments, the compounds of the disclosure as described herein can be used to treat Alzheimer's disease, HIV, or tuberculosis.

In addition to oncogenic neoplasms, the compounds of the disclosure can be useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes.

The compounds provided herein may further be useful in the treatment of fibrotic diseases, such as where a disease symptom or disorder is characterized by fibrosis. Example fibrotic diseases include liver cirrhosis, glomerulonephritis, pulmonary fibrosis, systemic fibrosis, rheumatoid arthritis, and wound healing.

In some embodiments, the compounds provided herein can be used in the treatment of a hypophosphatemia disorder such as, for example, X-linked hypophosphatemic rickets, autosomal recessive hypophosphatemic rickets, and autosomal dominant hypophosphatemic rickets, or tumor-induced osteromalacia.

In some embodiments, provided herein is a method of increasing survival or progression-free survival in a patient, comprising administering a compound provided herein to the patient. In some embodiments, the patient has cancer. In some embodiments, the patient has a disease or disorder described herein. In some embodiments, the patient has cholangiocarcinoma. In some embodiments, provided herein is a method of increasing survival or progression-free survival in a patient that has cholangiocarcinoma, wherein the cholangiocarcinoma is characterized by an FGFR2 fusion, comprising administering a compound provided herein to the patient. As used herein, progression-free survival refers to the length of time during and after the treatment of a solid tumor that a patient lives with the disease but it does not get worse. Progression-free survival can refer to the length of time from first administering the compound until the earlier of death or progression of the disease. Progression of the disease can be defined by RECIST v. 1.1 (Response Evaluation Criteria in Solid Tumors), as assessed by an independent centralized radiological review committee. In some embodiments, administering of the compound results in a progression free survival that is greater than about 1 month, about 2 months, about 3 months, about 4 months, about 5 months, about 6 months, about 8 months, about 9 months, about 12 months, about 16 months, or about 24 months. In some embodiments, the administering of the compound results in a progression free survival that is at least about 1 month, about 2 months, about 3 months, about 4 months, about 5 months, about 6 months, about 8 months, about 9 months, or about 12 months; and less than about 24 months, about 16 months, about 12 months, about 9 months, about 8 months, about 6 months, about 5 months, about 4 months, about 3 months, or about 2 months. In some embodiments, the administering of the compound results in an increase of progression free survival that is at least about 1 month, about 2 months, about 3 months, about 4 months, about 5 months, about 6 months, about 8 months, about 9 months, or about 12 months; and less than about 24 months, about 16 months, about 12 months, about 9 months, about 8 months, about 6 months, about 5 months, about 4 months, about 3 months, or about 2 months.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the FGFR enzyme with a compound described herein (e.g., Compound 1) includes the administration of a compound described herein to an individual or patient, such as a human, having FGFR, as well as, for example, introducing a compound described herein (e.g., Compound 1) into a sample containing a cellular or purified preparation containing the FGFR enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

It is appreciated that certain features of the disclosure, which are, for clarity, described in the context of separate embodiments, can also be provided in combination in a single embodiment (while the embodiments are intended to be combined as if written in multiply dependent form). Conversely, various features of the disclosure which are, for brevity, described in the context of a single embodiment, can also be provided separately or in any suitable subcombination.

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with compounds described herein for treatment of FGFR-associated diseases, disorders or conditions, or diseases or conditions as described herein. The agents can be combined with the present compounds in a single dosage form, or the agents can be administered simultaneously or sequentially as separate dosage forms.

Compounds described herein can be used in combination with one or more other kinase inhibitors for the treatment of diseases, such as cancer, that are impacted by multiple signaling pathways. For example, a combination can include one or more inhibitors of the following kinases for the treatment of cancer: Akt1, Akt2, Akt3, TGF-βR, Pim, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf Additionally, the solid forms of the FGFR inhibitor as described herein can be combined with inhibitors of kinases associated with the PIK3/Akt/mTOR signaling pathway, such as PI3K, Akt (including Akt1, Akt2 and Akt3) and mTOR kinases.

In some embodiments, compounds described herein can be used in combination with one or more inhibitors of the enzyme or protein receptors such as HPK1, SBLB, TUT4, A2A/A2B, CD47, CDK2, STING, ALK2, LIN28, ADAR1, MAT2a, RIOK1, HDAC8, WDR5, SMARCA2, and DCLK1 for the treatment of diseases and disorders. Exemplary diseases and disorders include cancer, infection, inflammation and neurodegenerative disorders.

In some embodiments, compounds described herein can be used in combination with a therapeutic agent that targets an epigenetic regulator. Examples of epigenetic regulators include bromodomain inhibitors, the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, compounds described herein can be used in combination with targeted therapies, including JAK kinase inhibitors (Ruxolitinib, additional JAK1/2 and JAK1-selective, baricitinib or INCB39110), Pim kinase inhibitors (e.g., LGH447, INCB053914 and SGI-1776), PI3 kinase inhibitors including PI3K-delta selective and broad spectrum PI3K inhibitors (e.g., INCB50465 and INCB54707), PI3K-gamma inhibitors such as PI3K-gamma selective inhibitors, MEK inhibitors, CSF1R inhibitors (e.g., PLX3397 and LY3022855), TAM receptor tyrosine kinases inhibitors (Tyro-3, Axl, and Mer; e.g., INCB81776), angiogenesis inhibitors, interleukin receptor inhibitors, Cyclin Dependent kinase inhibitors, BRAF inhibitors, mTOR inhibitors, proteasome inhibitors (Bortezomib, Carfilzomib), HDAC-inhibitors (panobinostat, vorinostat), DNA methyl transferase inhibitors, dexamethasone, bromo and extra terminal family members inhibitors (for example, bromodomain inhibitors or BET inhibitors, such as OTX015, CPI-0610, INCB54329 or INCB57643), LSD1 inhibitors (e.g., GSK2979552, INCB59872 and INCB60003), arginase inhibitors (e.g., INCB1158), indoleamine 2,3-dioxygenase inhibitors (e.g., epacadostat, NLG919 or BMS-986205), PARP inhibitors (e.g., olaparib or rucaparib), and inhibitors of BTK such as ibrutinib. In addition, for treating cancer and other proliferative diseases, compounds described herein can be used in combination with targeted therapies such as, e.g., c-MET inhibitors (e.g., capmatinib), an anti-CD19 antibody (e.g., tafasitamab), an ALK2 inhibitor (e.g., INCB00928); or combinations thereof.

For treating cancer and other proliferative diseases, compounds described herein can be used in combination with chemotherapeutic agents, agonists or antagonists of nuclear receptors, or other anti-proliferative agents. Compounds described herein can also be used in combination with a medical therapy such as surgery or radiotherapy, e.g., gamma-radiation, neutron beam radiotherapy, electron beam radiotherapy, proton therapy, brachytherapy, and systemic radioactive isotopes.

Examples of suitable chemotherapeutic agents include any of abarelix, abiraterone, afatinib, aflibercept, aldesleukin, alemtuzumab, alitretinoin, allopurinol, altretamine, amidox, amsacrine, anastrozole, aphidicolon, arsenic trioxide, asparaginase, axitinib, azacitidine, bevacizumab, bexarotene, baricitinib, bendamustine, bicalutamide, bleomycin, bortezombi, bortezomib, brivanib, buparlisib, busulfan intravenous, busulfan oral, calusterone, camptosar, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, didox, docetaxel, doxorubicin, droloxafine, dromostanolone propionate, eculizumab, enzalutamide, epidophyllotoxin, epirubicin, epothilones, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lonafarnib, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, niraparib, nofetumomab, oserelin, oxaliplatin, paclitaxel, pamidronate, panitumumab, panobinostat, pazopanib, pegaspargase, pegfilgrastim, pemetrexed disodium, pentostatin, pilaralisib, pipobroman, plicamycin, ponatinib, porfimer, prednisone, procarbazine, quinacrine, ranibizumab, rasburicase, regorafenib, reloxafine, revlimid, rituximab, rucaparib, ruxolitinib, sorafenib, streptozocin, sunitinib, sunitinib maleate, tamoxifen, tegafur, temozolomide, teniposide, testolactone, tezacitabine, thalidomide, thioguanine, thiotepa, tipifarnib, topotecan, toremifene, tositumomab, trastuzumab, tretinoin, triapine, trimidox, triptorelin, uracil mustard, valrubicin, vandetanib, vinblastine, vincristine, vindesine, vinorelbine, vorinostat, veliparib, talazoparib, and zoledronate.

In some embodiments, compounds described herein can be used in combination with immune checkpoint inhibitors. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3 (e.g., INCAGN2385), TIM3 (e.g., INCB2390), VISTA, PD-1, PD-L1 and PD-L2. In some embodiments, the immune checkpoint molecule is a stimulatory checkpoint molecule selected from CD27, CD28, CD40, ICOS, OX40 (e.g., INCAGN1949), GITR (e.g., INCAGN1876) and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is a small molecule PD-L1 inhibitor. In some embodiments, the small molecule PD-L1 inhibitor has an IC50 less than 1 µM, less than 100 nM, less than 10 nM or less than 1 nM in a PD-L1 assay described in US Patent Publication Nos. US 20170107216, US 20170145025, US 20170174671, US 20170174679, US 20170320875, US 20170342060, US 20170362253, and US 20180016260, each of which is incorporated by reference in its entirety for all purposes.

In some embodiments, the inhibitor of an immune checkpoint molecule is an inhibitor of PD-1, e.g., an anti-PD-1 monoclonal antibody. In some embodiments, the anti-PD-1 monoclonal antibody is MGA012 (retifanlimab), nivolumab, pembrolizumab (also known as MK-3475), pidilizumab, SHR-1210, PDR001, ipilumimab or AMP-224. In some embodiments, the anti-PD-1 monoclonal antibody is nivolumab or pembrolizumab. In some embodiments, the anti-PD1 antibody is pembrolizumab. In some embodiments, the anti-PD1 antibody is nivolumab. In some embodiments, the anti-PD-1 monoclonal antibody is MGA012 (retifanlimab). In some embodiments, the anti-PD1 antibody is SHR-1210. Other anti-cancer agent(s) include antibody therapeutics such as 4-1BB (e.g. urelumab, utomilumab.

In some embodiments, the compounds of the disclosure can be used in combination with INCB086550.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

In some embodiments, the compounds described herein can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Suitable antiviral agents contemplated for use in combination with compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2′,3′-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with compounds described herein for the treatment of cancer include chemotherapeutic agents, targeted cancer therapies, immunotherapies or radiation therapy. Compounds described herein may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds described herein. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

The compounds described herein may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with FGFR inhibitors. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with FGFR inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds described herein include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with FGFR inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds described herein. In some embodiments, the JAK inhibitor is selective for JAK1 over JAK2 and JAK3.

Other suitable agents for use in combination with compounds described herein include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with compounds described herein include steroids including 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

Other suitable agents for use in combination with compounds described herein include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds described herein may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, *vinca* alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-L1 and PD-1 antibodies, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of the present disclosure can be used in combination with bone marrow transplant for the treatment of a variety of tumors of hematopoietic origin.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

As provided throughout, the additional compounds, inhibitors, agents, etc. can be combined with the present compound in a single or continuous dosage form, or they can be administered simultaneously or sequentially as separate dosage forms.

Pharmaceutical Formulations and Dosage Forms

In some embodiments, a compound of the disclosure or a pharmaceutical composition thereof is suitable for oral administration. In some embodiments, a compound of the disclosure or a pharmaceutical composition thereof is suitable for intravenous administration. In some embodiments, a compound of the disclosure or a pharmaceutical composition thereof is suitable for arterial administration. In some embodiments, the arterial administration is hepatic arterial infusion.

When employed as pharmaceuticals, the compounds as described herein can be administered in the form of pharmaceutical compositions which refers to a combination of one or more compounds as described herein, and at least one pharmaceutically acceptable carrier. The pharmaceutical composition of the disclosure may contain 20% by weight of the compound or a salt thereof. The pharmaceutical composition of the disclosure may contain 30% by weight of the compound or a salt thereof. The pharmaceutical composition of the disclosure may contain 40% by weight of the compound or a salt thereof. The pharmaceutical composition of the disclosure may contain 50% by weight of the compound or a salt thereof. The pharmaceutical composition of the disclosure may contain 60% by weight of the compound or a salt thereof. The pharmaceutical composition of the disclosure may contain 70% by weight of the compound or a salt thereof. The pharmaceutical composition of the disclosure may contain 80% by weight of the compound or a salt thereof. The pharmaceutical composition of the disclosure may contain 90% by weight of the compound or a salt thereof. The pharmaceutical composition of the disclosure may contain 95% by weight of the compound or a salt thereof. The pharmaceutical composition of the disclosure may contain 99% by weight of the compound or a salt thereof.

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compounds of the disclosure in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the disclosure. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds of the disclosure, or compositions as described herein can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound described herein can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, a compound described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

A compound of the disclosure can also be formulated in combination with one or more additional active ingredients which can include any pharmaceutical agent such as antiviral agents, vaccines, antibodies, immune enhancers, immune suppressants, anti-inflammatory agents and the like.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Haque, A. Combs, J. Combi. Chem., 5, 670 (2003); and "Preparative LC-MS Purification: Improved Compound Specific Method Optimization", K. Blom, B. Glass, R. Sparks, A. Combs, J Combi. Chem., 6, 874-883 (2004). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 µm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, J. Comb. Chem., 6, 874-883 (2004)]. Typically, the flow rate used with the 30×100 mm column was 60 mL/minute.

pH=10 purifications: Waters XBridge $C_{18}$ 5 µm, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, J. Comb. Chem., 6, 874-883 (2004)]. Typically, the flow rate used with 30×100 mm column was 60 mL/minute.

Example 1

Synthesis of 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one (Compound 1)

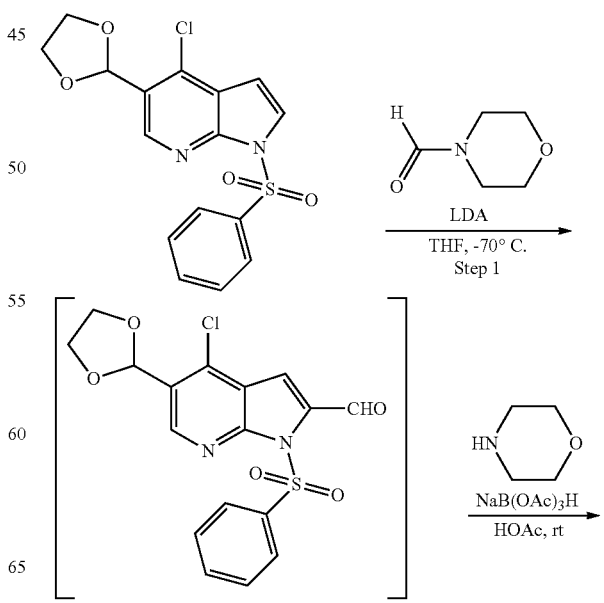

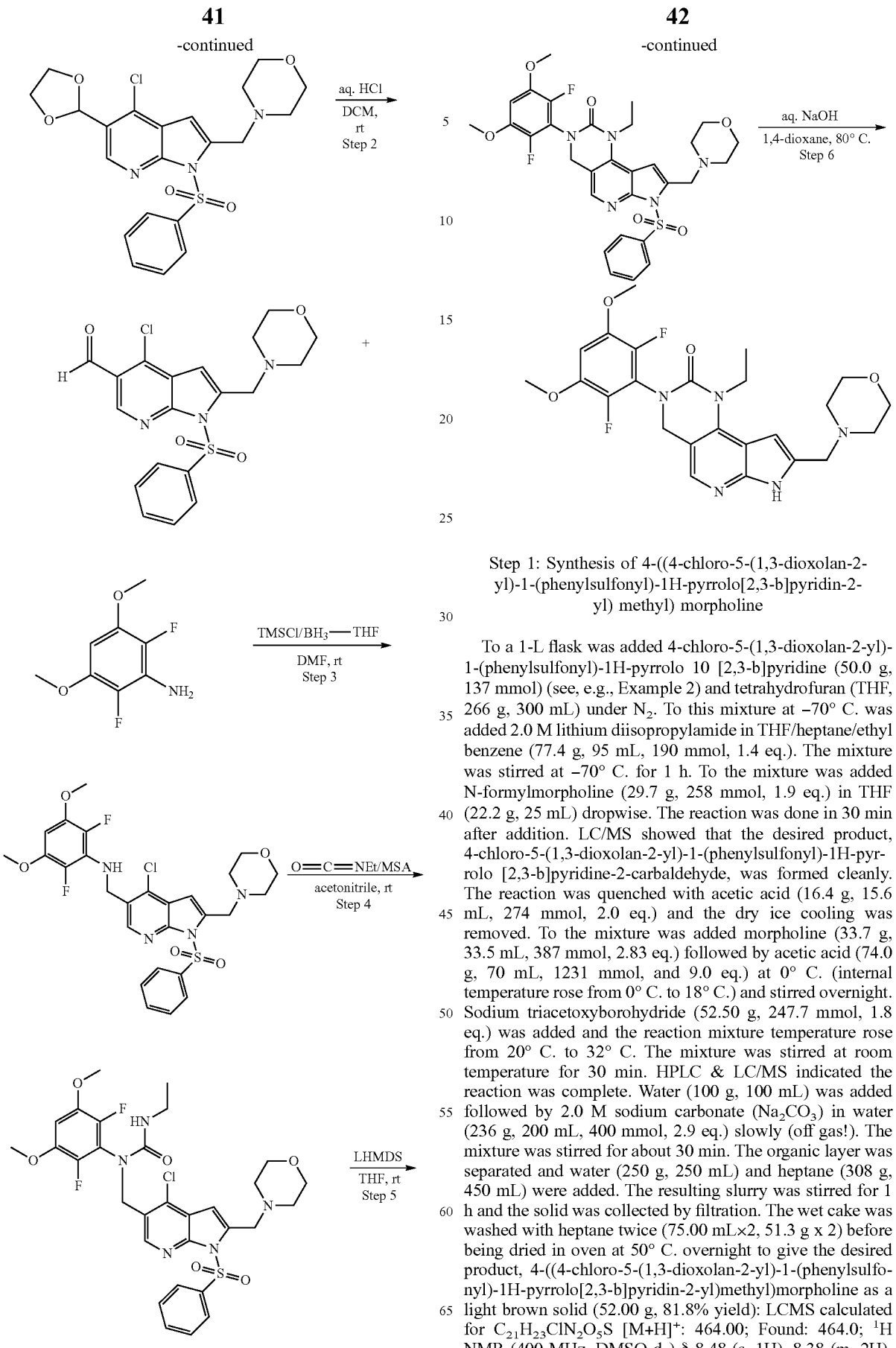

Step 1: Synthesis of 4-((4-chloro-5-(1,3-dioxolan-2-yl)-1-(phenylsulfonyl)-1H-pyrrolo[2,3-b]pyridin-2-yl) methyl) morpholine To a 1-L flask was added 4-chloro-5-(1,3-dioxolan-2-yl)-1-(phenylsulfonyl)-1H-pyrrolo 10 [2,3-b]pyridine (50.0 g, 137 mmol) (see, e.g., Example 2) and tetrahydrofuran (THF, 266 g, 300 mL) under $N_2$. To this mixture at −70° C. was added 2.0 M lithium diisopropylamide in THF/heptane/ethyl benzene (77.4 g, 95 mL, 190 mmol, 1.4 eq.). The mixture was stirred at −70° C. for 1 h. To the mixture was added N-formylmorpholine (29.7 g, 258 mmol, 1.9 eq.) in THF (22.2 g, 25 mL) dropwise. The reaction was done in 30 min after addition. LC/MS showed that the desired product, 4-chloro-5-(1,3-dioxolan-2-yl)-1-(phenylsulfonyl)-1H-pyrrolo [2,3-b]pyridine-2-carbaldehyde, was formed cleanly. The reaction was quenched with acetic acid (16.4 g, 15.6 mL, 274 mmol, 2.0 eq.) and the dry ice cooling was removed. To the mixture was added morpholine (33.7 g, 33.5 mL, 387 mmol, 2.83 eq.) followed by acetic acid (74.0 g, 70 mL, 1231 mmol, and 9.0 eq.) at 0° C. (internal temperature rose from 0° C. to 18° C.) and stirred overnight. Sodium triacetoxyborohydride (52.50 g, 247.7 mmol, 1.8 eq.) was added and the reaction mixture temperature rose from 20° C. to 32° C. The mixture was stirred at room temperature for 30 min. HPLC & LC/MS indicated the reaction was complete. Water (100 g, 100 mL) was added followed by 2.0 M sodium carbonate ($Na_2CO_3$) in water (236 g, 200 mL, 400 mmol, 2.9 eq.) slowly (off gas!). The mixture was stirred for about 30 min. The organic layer was separated and water (250 g, 250 mL) and heptane (308 g, 450 mL) were added. The resulting slurry was stirred for 1 h and the solid was collected by filtration. The wet cake was washed with heptane twice (75.00 mL×2, 51.3 g × 2) before being dried in oven at 50° C. overnight to give the desired product, 4-((4-chloro-5-(1,3-dioxolan-2-yl)-1-(phenylsulfonyl)-1H-pyrrolo[2,3-b]pyridin-2-yl)methyl)morpholine as a light brown solid (52.00 g, 81.8% yield): LCMS calculated for $C_{21}H_{23}ClN_2O_5S$ [M+H]$^+$: 464.00; Found: 464.0; $^1$H NMR (400 MHz, DMSO-$d_6$) δ 8.48 (s, 1H), 8.38 (m, 2H), 7.72 (m, 1H), 7.64 (m, 2H), 6.83 (s, 1H), 6.13 (s, 1H), 4.12 (m, 2H), 4.00 (m, 2H), 3.92 (s, 2H), 3.55 (m, 4H), 2.47 (m, 4H).

Step 2: Synthesis of 4-chloro-2-(morpholinomethyl)-1-(phenylsulfonyl)-1H-pyrrolo[2,3-b]pyridine-5-carbaldehyde To a 2 L reactor with a thermocouple, an addition funnel, and a mechanical stirrer was charged 4-((4-chloro-5-(1,3-dioxolan-2-yl)-1-(phenylsulfonyl)-1H-pyrrolo[2,3-b]pyridin-2-yl)methyl)morpholine (20.00 g, 43.1 mmol) and dichloromethane (265 g, 200 mL) at room temperature. The resulting mixture was stirred at room temperature (internal temperature was 19.5° C.) to achieve a solution. To the resulting solution was added an aqueous hydrochloric acid solution (0.5 M, 240 g, 200.0 ml, 100 mmol, 2.32 eq.) at room temperature in 7 min. After over 23 h agitations at room temperature, the bilayer reaction mixture turned into a thick colorless suspension. When HPLC showed the reaction was complete, the slurry was cooled to 0-5° C. and aqueous sodium hydroxide solution (1 N, 104 g, 100 mL, 100 mmol, and 2.32 eq.) was added in about 10 min to adjust the pH of the reaction mixture to 10-11. n-Heptane (164 g, 240 mL) was added and the reaction mixture and the mixture were stirred at room temperature for 1 h. The solid was collected by filtration and the wet cake was washed with water (2×40 mL), heptane (2×40 ml) before being dried in oven at 50° C. under vacuum to afford the desired product, 4-chloro-2-(morpholinomethyl)-1-(phenylsulfonyl)-1H-pyrrolo[2,3-b]pyridine-5-carbaldehyde as a light brown solid (16.9 g, 93% yield): LCMS calculated for $C_{19}H_{19}ClN_3O_4S$ [M+H]$^+$: 420.00; Found: 420.0; $^1$H NMR (400 MHz, DMSO-d$_6$) δ 10.33 (s, 1H), 8.76 (s, 1H), 8.42 (m, 2H), 7.74 (m, 1H), 7.65 (m, 2H), 6.98 (s, 1H), 3.96 (m, 2H), 3.564 (m, 4H), 2.51 (m, 4H).

Step 3: Synthesis of N-((4-chloro-2-(morpholinomethyl)-1-(phenylsulfonyl)-1H-pyrrolo [2,3-b]pyridin-5-yl) methyl)-2,6-difluoro-3,5-dimethoxyaniline To a 2-L reactor equipped with a thermocouple, a nitrogen inlet and mechanical stirrer were charged N,N-dimethyl formamide (450 mL, 425 g), 4-chloro-2-(morpholinomethyl)-1-(phenylsulfonyl)-1H-pyrrolo[2,3-b]pyridine-5-carbaldehyde (30.0 g, 71.45 mmol) and 2,6-difluoro-3,5-dimethoxyaniline (14.2 g, 75.0 mmol). To this suspension (internal temperature 20° C. was added chlorotrimethylsilane (19.4 g, 22.7 mL, 179 mmol) dropwise in 10 min at room temperature (internal temperature 20-23° C.). The suspension changed into a solution in 5 min after the chlorotrimethylsilane addition. The solution was stirred at room temperature for 1.5 h before cooled to 0-5° C. with ice-bath. Borane-THF complex in THF (1.0 M, 71.4 mL, 71.4 mmol, 64.2 g, 1.0 eq.) was added dropwise via additional funnel over 30 min while maintaining temperature at 0-5° C. After addition, the mixture was stirred for 4 h. Water (150 g, 150 mL) was added under ice-bath cooling in 20 min, followed by slow addition of ammonium hydroxide solution (28% NH$_3$, 15.3 g, 17 ml, 252 mmol, 3.53 eq.) to pH 9-10 while maintaining the temperature below 10° C. More water (250 mL, 250 g) was added through the additional funnel. The slurry was stirred for 30 min and the solids were collected by filtration. The wet cake was washed with water (90 g×2, 90 ml x 2) and heptane (61.6 g×2, 90 ml x 2). The product was suction dried overnight to give the desired product N-((4-chloro-2-(morpholinomethyl)-1-(phenylsulfonyl)-1H-pyrrolo[2,3-b]pyridin-5-yl)methyl)-2,6-difluoro-3,5-dimethoxyaniline (41.6 g, 96% yield): LCMS calculated for $C_{27}H_{28}ClF_2N_4O_5S$ [M+H]$^+$: 593.10; Found: 593.1; $^1$H NMR (400 MHz, DMSO-d$_6$) δ 8.36 (m, 2H), 8.28 (s, 1H), 7.72 (m, 1H), 7.63 (m, 2H), 6.78 (s, 1H), 6.29 (m, 1H), 5.82 (m, 1H), 4.58 (m, 2H), 3.91 (s, 2H), 3.76 (s, 6H), 3.56 (m, 4H), 2.47 (m, 4H).

Step 4: Synthesis of 1-((4-chloro-2-(morpholinomethyl)-1-(phenylsulfonyl)-1H-pyrrolo [2,3-b]pyridin-5-yl) methyl)-1-(2,6-difluoro-3,5-dimethoxyphenyl)-3-ethylurea To a 2-L, 3-neck round bottom flask fitted with a thermocouple, a nitrogen bubbler inlet, and a magnetic stir were charged N-((4-chloro-2-(morpholinomethyl)-1-(phenylsulfonyl)-1H-pyrrolo[2,3-b]pyridin-5-yl)methyl)-2,6-difluoro-3,5-dimethoxyaniline (67.0 g, 113 mmol) and acetonitrile (670 ml, 527 g). The suspension was cooled to 0-5° C. To the mixture was charged ethyl isocyanate (17.7 mL, 15.9 g, 224 mmol, 1.98 eq.) over 30 sec. The temperature stayed unchanged at 0.7° C. after the charge. Methanesulfonic acid (16.1 mL, 23.9 g, 248 mmol, 2.2 eq.) was charged dropwise over 35 min while maintaining the temperature below 2° C. The mixture was warmed to room temperature and stirred overnight. At 24 h after addition showed that the product was 93.7%, unreacted SM was 0.73% and the major impurity (bis-isocyanate adduct) was 1.3%. The mixture was cooled with an ice-bath and quenched with sodium hydroxide (NaOH) solution (1.0M, 235 mL, 244 g, 235 mmol, 2.08 eq.) over 20 min and then saturated aqueous sodium bicarbonate (NaHCO$_3$) solution (1.07 M, 85 mL, 91 g, 0.091 mol, 0.80 eq.) over 10 min. Water (550 mL, 550 g) was added and the liquid became one phase. The mixture was stirred for 2 h and the solids were collected by filtration, washed with water (165 mL, 165 g) to give 1-((4-chloro-2-(morpholinomethyl)-1-(phenylsulfonyl)-1H-pyrrolo[2,3-b]pyridin-5-yl)methyl)-1-(2,6-difluoro-3,5-dimethoxyphenyl)-3-ethylurea (70.3 g, 93.7% yield).

The crude 1-((4-chloro-2-(morpholinomethyl)-1-(phenylsulfonyl)-1H-pyrrolo [2,3-b]pyridin-5-yl) methyl)-1-(2, 6-difluoro-3,5-dimethoxyphenyl)-3-ethylurea (68.5 g, 103 mmol) was added in to acetonitrile (616 mL, 485 g). The mixture was heated 60-65° C. and an amber colored thin suspension was obtained. The solid was filtered off with celite and the celite was washed with acetonitrile (68.5 mL, 53.8 g). To the pale yellow filtrate was added water (685 g, 685 ml) to form a slurry. The slurry was stirred overnight at room temperature and filtered. The solid was added to water (685 mL, 685 g) and stirred at 60° C. for 2 h. The solid was filtered and re-slurred in heptane (685 mL, 469 g) overnight. The product was dried in an oven at 50° C. under vacuum for 48 h to afford 1-((4-chloro-2-(morpholinomethyl)-1-(phenylsulfonyl)-1H-pyrrolo[2,3-b]pyridin-5-yl)methyl)-1-(2,6-difluoro-3,5-dimethoxyphenyl)-3-ethylurea as a colorless solid (62.2 g, 90.8% yield, 99.9% purity by HPLC area %). KF was 0.028%. Acetonitrile (by $^1$H NMR) was about 1.56%, DCM (by $^1$H NMR) 2.0%: LCMS calculated for $C_{30}H_{33}ClF_2N_5O_6S$ [M+H]$^+$: EM: 664.17; Found: 664.2; $^1$H NMR (400 MHz, DMSO-d$_6$) δ 8.33 (m, 2H), 8.31 (s, 1H), 7.72 (m, 1H), 7.64 (m, 1H), 6.96 (m, 2H), 6.73 (s, 1H), 6.43 (m, 1H), 4.87 (s, 2H), 3.90 (s, 2H), 3.77 (s, 6H), 3.54 (m, 4H), 3.03 (m, 2H), 2.46 (m, 4H), 0.95 (m, 3H).

Step 5: Synthesis of 3-(2,6-difluoro-3,5-dimethoxy-phenyl)-1-ethyl-8-(morpholin-4-ylmethyl)-7-(phenylsulfonyl)-1,3,4,7-tetrahydro-2H-pyrrolo[3',2':5,6]pyrido[4,3-d]pyrimidin-2-one To a 2000 mL flask equipped with a thermal couple, a nitrogen inlet, and a mechanical stirrer were charged dry 1-((4-chloro-2-(morpholinomethyl)-1-(phenylsulfonyl)-1H-pyrrolo[2,3-b]pyridin-5-yl)methyl)-1-(2,6-difluoro-3,5-dimethoxyphenyl)-3-ethylurea (30.0 g, 45.2 mmol, KF=0.11%) and tetrahydrofuran (1200 mL, 1063 g). To this suspension at room temperature was charged 1.0 M lithium hexamethyldisilazide in THF (62.3 mL, 55.5 g, 62.3 mmol, 1.38 eq). The mixture turned into a solution after the base addition. The reaction mixture was stirred for 2 h and HPLC shows the starting material was not detectable. To this mixture was added 1.0 M hydrochloric acid (18.1 mL, ~18.1 g. 18.1 mmol, 0.4 eq.). The solution was concentrated to 600 mL and water (1200 mL, 1200 g) was added. Slurry was formed after water addition. The slurry was stirred for 30 min at room temperature and the solid was collected by filtration. The wet cake was washed with water twice (60 mL×2, 60 g×2) and dried at 50° C. overnight to give 3-(2,6-difluoro-3,5-dimethoxyphenyl)-1-ethyl-8-(morpholin-4-ylmethyl)-7-(phenylsulfonyl)-1,3,4,7-tetrahydro-2H-pyrrolo[3',2':5,6]pyrido[4,3-d]pyrimidin-2-one as a light brown solid (26.58 g, as-is yield 93.7%): THF by $^1$H NMR 0.32%, KF 5.26%, adjusted yield was 88.5%: LCMS calculated for $C_{30}H_{32}F_2N_5O_6S$ [M+H]$^+$: EM: 628.20; Found: 628.2; $^1$H NMR (400 MHz, DMSO-$d_6$) δ 8.41 (m, 2H), 8.07 (s, 1H), 7.70 (m, 1H), 7.63 (m, 2H), 7.05 (m, 1H), 6.89 (s, 1H), 4.76 (s, 2H), 4.09 (m, 2H), 3.93 (s, 2H), 3.89 (s, 6H), 3.60 (m, 4H), 2.50 (m, 4H), 1.28 (m, 3H).

Step 6: Synthesis of 3-(2,6-difluoro-3,5-dimethoxy-phenyl)-1-ethyl-8-(morpholin-4-ylmethyl)-1,3,4,7-tetrahydro-2H-pyrrolo[3',2':5,6]pyrido[4,3-d]pyrimidin-2-one To a stirring suspension of 3-(2,6-difluoro-3,5-dimethoxyphenyl)-1-ethyl-8-(morpholinomethyl)-7-(phenylsulfonyl)-1,3,4,7-tetrahydro-2H-pyrrolo[3',2':5,6]pyrido[4,3-d]pyrimidin-2-one (10.0 g, 15.93 mmol) in 1,4-dioxane (100 ml, 103 g) in a 500 mL flask equipped with a nitrogen inlet, a condenser, a thermocouple and a heating mantle was added 1 M aqueous sodium hydroxide (63.7 ml, 66.3 g, 63.7 mmol). The reaction mixture was heated at 75° C. for 18 h. LCMS showed the reaction was complete. Water (100 mL, 100 g) was added to give a thick suspension. This slurry was stirred at room temperature for 1 h and filtered. The cake was washed with water (3×10 mL, 3×10 g) and heptane (2×10 mL, 2×6.84 g). The cake was dried overnight by pulling a vacuum through the filter cake and then dried in an oven at 50° C. under vacuum overnight to give 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one (6.8 g, 87.6% yield): LCMS calculated for $C_{24}H_{28}F_2N_5O_4$[M+H]$^+$: 488.20; Found: 488.2.

Example 2. Synthesis of 4-chloro-5-(1,3-dioxolan-2-yl)-1-(phenylsulfonyl)-1H-pyrrolo [2,3-b]pyridine

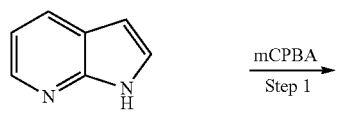

Step 1: Synthesis of 1H-pyrrolo[2,3-b]pyridine-7-oxide m-Chloroperoxybenzoic acid (105.5 Kg, 612 mol, 1.2 eq) was added to a solution of 1H-pyrrolo[2,3-b]pyridine (60 Kg, 507.6 mol) in dichloromethane (600 L) over 5 h with stirring at 0-10° C. After completion of the addition, the mixture was stirred at 0-10° C. for 3 h. The resulting solid was collected by filtration, washed with heptane, and dried to give 1H-pyrrolo[2,3-b]pyridine 7-oxide. The mother liquid was concentrated and the residue was treated with dichloromethane: heptane (2:3), and filtered to recover extra materials. The crude 1H-pyrrolo 2,3-b]pyridine-7-oxide was obtained (72 Kg, 96% purity), which was used to next step without purification.

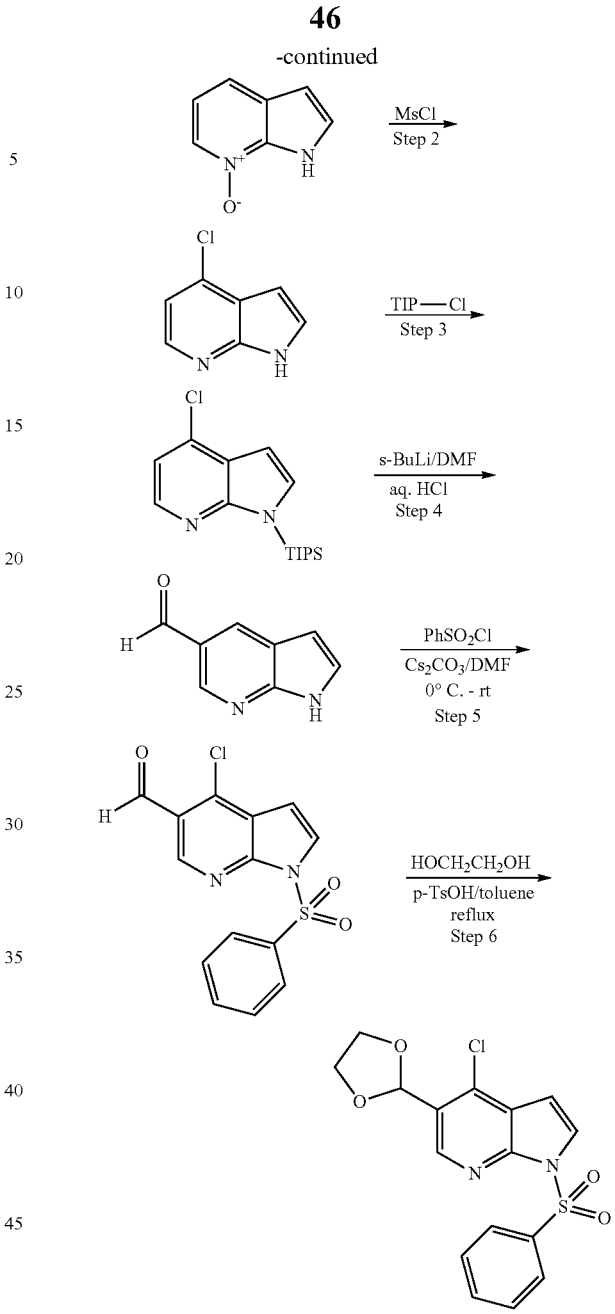

Step 2: Synthesis of 4-chloro-1H-pyrrolo[2,3-b]pyridine

The crude 1H-pyrrolo[2,3-b]pyridine-7-oxide (72 Kg, 253 mol) was dissolved in DMF (360 L) and heated at 50° C. A solution of methanesulfonyl chloride (85.2 Kg, 746 mol, 3.0 eq.) was added drop-wise to the solution while maintaining a temperature below 70° C. After being stirred at 90° C. for 2 h, the reaction solution was cooled to room temperature, and added to 720 Kg of ice/water. The mixture was neutralized with 6.0 M NaOH at 0° C. The resulting precipitate was collected by filtration, and washed with water. The solid was mixed with 72 L water, 48 L ethanol, and 29 L 30% NaOH, and stirred at room temperature for 1-2 h. Water (144 L) was added, and the mixture was treated with 37% HCl to adjust the pH to ~1. The product was collected by filtration and dried to give 4-chloro-1H-pyrrolo[2,3-b]pyridine (crude 26 kg, 97% purity, which was used without purification): $^1$HNMR (400 MHz, CDCl$_3$) δ 11.30 (s, 1H), 8.25 (m, 1H), 7.44 (m, 1H), 7.16 (m, 1H), 6.65 (m, 1H).

Step 3: Synthesis of 4-chloro-1-(triisopropylsilyl)-1H-pyrrolo[2,3-b]pyridine A solution of crude 4-chloro-1H-pyrrolo[2,3-b]pyridine (24 Kg, 155.2 mol) in THF (216 L) was stirred 0° C. as NaH (60%, 7.56 Kg, 188.6 mol, 1.3 eq.) was added portion-wise under N$_2$. After addition, the mixture was stirred at rt for 1 h. Triisopropylsilyl chloride (39.6 Kg, 188.6 mol, 1.3 eq) was added drop-wise while maintaining a temperature below 25° C. After stirring for 20 h, the mixture was quenched with 144 L water and extracted with 144 L heptane. The water layer was back extracted with 72 L methyl t-butyl ether. The combined organic layers were dried over anhydrous MgSO$_4$ and concentrated under vacuum to give crude 4-chloro-1-(triisopropylsilyl)-1H-pyrrolo[2,3-b]pyridine as a liquid. The material was used without purification, but its water content was controlled to below 0.1%.

Step 4: Synthesis of 4-chloro-1H-pyrrolo[2,3-b]pyridine-5-carbaldehyde

To a 1000 L cryogenic reactor was charged crude 4-chloro-1-(triisopropylsilyl)-1H-pyrrolo[2,3-b]pyridine (50 Kg, ~138 mol) and anhydrous THF (150 Kg). The mixture was cooled to −75° C., and stirred under N$_2$ as S-BuLi (1.3 M in cyclohexane, 230 L, 300 mol, 2.2 eq.) was added drop-wise over about 6.0 h while maintaining internal temperature below −60° C. The mixture was stirred at −75° C. for additional 2 h. N,N-Dimethylformamide (30.4 Kg, 416.1 mol, 3.0 eq.) was added drop-wise over a period of ~3.0 h to control the internal temperature below −65° C. After being stirred at −65~−75° C. for 2 h, the mixture was quenched by drop-wise addition of a solution of 20% HCl in isopropyl alcohol (115 Kg, 635 mol, 4.5 eq.). The mixture was then stirred at room temperature (20-25° C.) overnight. The pH was adjusted to 7-8 by charging saturated NaHCO$_3$. The precipitate formed was collected by filtration. The filter cake was washed with 76 L water to give 4-chloro-1H-pyrrolo[2,3-b]pyridine-5-carbaldehyde (14 Kg, 58% yield): $^1$HNMR (400 MHz, DMSO-d$_6$) δ 12.54 (s, 1H), 10.35 (s, 1H), 8.67 (s, 1H), 7.74 (m, 1H), 6.72 (m, 1H).

Step 5: Synthesis of 4-chloro-1-(phenylsulfonyl)-1H-pyrrolo[2,3-b]pyridine-5-carbaldehyde To a 500 L reactor was charged N,N-dimethylformamide (108 L) and 4-chloro-1H-pyrrolo[2,3-b]pyridine-5-carbaldehyde (10.8 Kg, 59.8 mol) and cooled to 0-5° C. To the resulting thick slurry was charged cesium carbonate (39 Kg, 120 mol) at 0-5° C. The slurry was stirred at 0° C. for about 20 min and the mixture changed to an amber colored thin slurry. To the thin slurry at below 10° C. was added benzenesulfonyl chloride (11.6 Kg, 65.8 mol, 1.1 eq.) drop-wise through an addition funnel. The resulting slurry was stirred for 1 h at below 10° C. and HPLC indicated the reaction was complete. Extended agitation at room temperature overnight had little impact on reaction mixture profile. To this mixture was added water (160 L) and the slurry was stirred for 1 h. The solid was collected by filtration (slow). The filter cake was washed with water and dried in oven under vacuum to give 4-chloro-1-(phenylsulfonyl)-1H-pyrrolo[2,3-b]pyridine-5-carbaldehyde as a light brown solid (17.8 Kg, 93% yield): LCMS calculated for $C_{14}H_{10}ClN_2O_3S$ [M+H]$^+$: 321.00; Found: 320.9; $^1$HNMR (400 MHz, DMSO-d$_6$) δ: 10.34 (s, 1H), 8.78 (s, 1H), 8.18 (m, 3H), 7.77 (m, 1H), 7.66 (m, 2H), 7.05 (m, 1H).

Step 6: Synthesis of 4-chloro-5-(1,3-dioxolan-2-yl)-1-(phenylsulfonyl)-1H-pyrrolo[2,3-b]pyridine)

To a 1000 L reactor were charged toluene (270 L), 4-chloro-1-(phenylsulfonyl)-1H-pyrrolo[2,3-b]pyridine-5-carbaldehyde (27 Kg, 84.2 mmol), p-toluenesulfonic acid monohydrate (217 g, 1.26 mol, 0.015 eq.), and 1,2-ethanediol (73.7 Kg, 1187 mol, 14.1 eq.). The mixture was stirred and heated to reflux to remove water (some ethylene glycol was also removed as the reaction progresses) for 9 h (LCMS showed reaction complete). After overnight stirring at room temperature, the mixture was diluted with ethyl acetate (135 L) and washed with saturated NaHCO$_3$ solution. The layers were separated and the organic layer was washed with 10% aq. NaCl solution and concentrated. Heptane (108 L) was added and slurry was formed. The solid was collected by filtration. The solid was dissolved in dichloromethane (108 L) and filtered in order to remove the mechanical impurities. The filtrate was concentrated, then dissolved in 67.5 L (2.5V) of hot ethyl acetate and stirred for 2 h. The mixture was allowed to cool as the solid formed. The solid was collected by filtration to give 4-chloro-5-(1,3-dioxolan-2-yl)-1-(phenylsulfonyl)-1H-pyrrolo[2,3-b]pyridine as an off-white solid (22 Kg, 70% yield): LCMS calculated for $C_{16}H_{14}ClN_2O_4S$ [M+H]$^+$: 365.03; Found: 365.1; $^1$H NMR (400 MHz, DMSO-d$_6$) δ 8.51 (s, 1H), 8.13 (m, 2H), 8.07 (m, 1H), 7.73 (m, 1H), 7.63 (m, 2H), 6.90 (m, 1H), 6.13 (s, 1H), 4.12 (m, 2H), 3.98 (m, 2H).

Example 3. An alternate synthesis of 4-chloro-2-(morpholin-4-ylmethyl)-1-(phenylsulfonyl)-1H-pyrrolo[2,3-b]pyridine-5-carbaldehyde

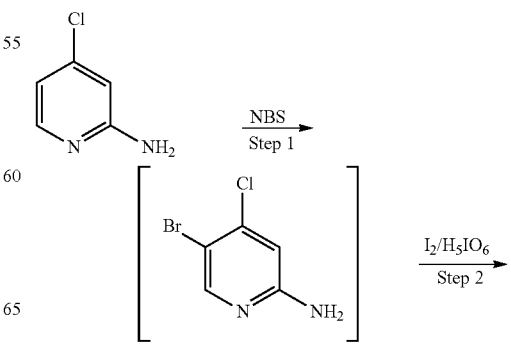

49

-continued

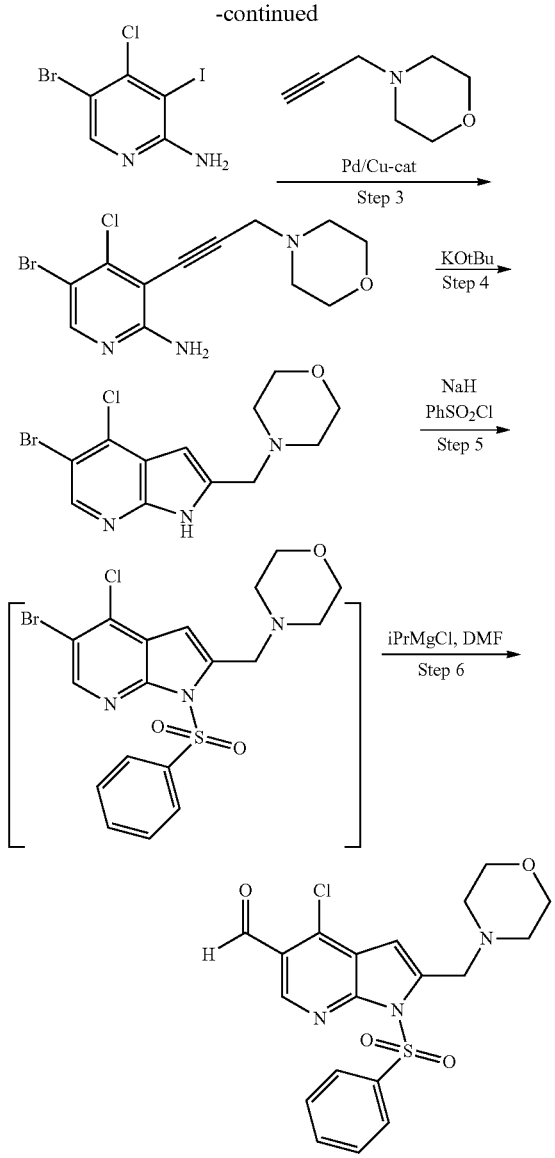

Step 1: Synthesis of 5-bromo-4-chloropyridin-2-amine

A slurry of 2-amino-4-chloropyridine (100 g, 777.8 mmol, 1.0 eq.) in acetonitrile (500 mL, 5 rel. vol.) at 15-20° C. was added N-bromosuccinimide (131.5 g, 738.9 mmol, 0.95 eq.) in portions over 2 h keeping the temperature at 15-20° C. The reaction was stirred for 30 min and the conversion was checked by HPLC. Depending on the conversion, 0-5 mol % of additional N-bromosuccinimide was added and the mixture was stirred for another 15 min. After HPLC indicated the conversion was complete, the reaction mixture was heated and acetonitrile (300 mL) was distilled off at normal pressure. Water (250 mL) was added and the temperature was adjusted to 50-55° C. and slurry was formed. The resulting slurry was stirred for 30 min and water (350 mL) was added over 1 h. The slurry was cooled to 20-25° C., stirred for 1 h and the solid was collected by filtration. The wet cake was washed with a mixture of water (75 mL) and acetonitrile (25 mL) to give the wet product 5-bromo-4-chloropyridin-2-amine (191 g, 92.1% by HPLC area % purity). The wet product was dissolved in acetic acid (500 mL, 5 rel. vol. on 2-amino-4-chloropyridine, 55-70° C.) and the solution was directly used in the next step.

Step 2: Synthesis of 5-bromo-4-chloro-3-iodopyridin-2-amine

The solution of 5-bromo-4-chloropyridin-2-amine in acetic acid (191 g, 5-bromo-4-chloropyridin-2-amine in 500 mL acetic acid) was distilled under reduced pressure at 40-60° C. to remove the solvents. Then, sulfuric acid (39.7 g, 96%-w/w, 388.9 mmol, 0.5 eq.) and iodine (76.2 g, 300.3 mmol, 0.386 eq.) were added and the temperature was adjusted to 77-83° C. At this temperature, a solution of periodic acid (50%-w/w, 54.89 g, 120.4 mmol, 0.155 eq.) was added over 2-3 h. The reaction was stirred for 2-3 h at 77-83° C. and the conversion was checked by HPLC (SM<1.0%-a/a). At 75-85° C., the reaction mixture was quenched by the addition of solid ammonium sulfite in portions of 4.53 g (0.05 eq.) until the KI/starch test was negative. Typically two portions (0.1 eq.) of ammonium sulfite were required. The end of the quench may also be seen by the absence of the purple color of iodine. Then, the reaction mixture was diluted with water (200 mL, 2.0 rel. vol., at room temperature), and the temperature was dropped to ~50° C. The product was precipitated out. At 45-60° C., the pH was adjusted to 3.0-3.5 with ammonia (25%-w/w in water, about 63.6 g, 0.93 mol, 1.2 eq. needed). The neutralization was strongly exothermic. The slurry was stirred for 30 min at 45-50° C. and then the solid was collected by filtration. The filter cake was washed with typically about 600 mL water and then washed with 2-propanol (200 mL). The wet product was dried in the vacuum cabinet at 60° C. to give 5-bromo-4-chloro-3-iodopyridin-2-amine as a yellow to beige solid (213.5 g, 82.3% yield): LCMS calculated for $C_5H_4BrClIN_2$ [M+H]$^+$: 332.82; Found: 332.8; $^1$H NMR (400 MHz, DMSO-d$_6$) δ 8.09 (s, 1H), 6.60 (s, 2H).

Step 3: Synthesis of 5-bromo-4-chloro-3-(3-morpholinoprop-1-yn-1-yl)pyridin-2-amine 5-Bromo-4-chloro-3-iodopyridin-2-amine (50 g, 150 mmol, 1.0 eq.), 4-(prop-2-ynyl)morpholine (22.5 g, 180 mmol, 1.20 eq.), diisopropylamine (18.2 g, 180 mmol, 1.2 eq.) and 150 mL of toluene were charged to a reactor. The solution was carefully degassed applying 3 vacuum argon cycles. Then, CuI (0.29 g, 1.5 mmol, 1 mol %) and Pd(PPh$_3$)$_4$ were added and the flask purged again with argon. The mixture was stirred at 50° C. overnight (17 h). Water (50 mL, 1 vol.) was added in one portion and the mixture was cooled to 20-25° C. The crude product was filtered off and washed consecutively with 10% ammonia (50 ml, 1.0 vol.), water (50 ml, 1 vol.), toluene (25 ml, 0.5 vol.), and with 2-isopropanol (50 ml, 1.0 vol.). After drying under vacuum at 50° C., 5-bromo-4-chloro-3-(3-morpholinoprop-1-yn-1-yl)pyridin-2-amine was obtained as light brown solid (41.6 g, 87% yield): LCMS calculated for $C_{12}H_{14}BrClN_5O$ [M+H]$^+$: 329.99; Found: 330.0; $^1$H NMR (400 MHz, DMSO-d$_6$) δ 8.13 (s, 1H), 6.69 (s, 2H), 3.64 (s, 2H), 3.61 (m, 4H), 2.54 (m, 4H).

Step 4: Synthesis of 4-((5-bromo-4-chloro-1H-pyrrolo[2,3-b]pyridin-2-yl)methyl)morpholine A solution of KOtBu (18.1 g, 1.4 eq., 112.21 mmol) in tetrahydrofuran (114 ml, 3 vol) was heated to 30-35° C. as 5-bromo-4-chloro-3-(3-morpholinoprop-1-yn-1-yl)pyridin- 2-amine (38 g, 114.9 mmol, 1.0 eq.) was added in portions over 1.0 h at 30-35° C. After stirring for 2 h, the reaction was quenched with a solution of acetic acid (10.4 g, 172.4 mmol, 1.5 eq.) in water (76 mL, 2 vol.) and 76 mL of THF (76 mL) was removed by distillation. Then the solution was heated to reflux and MeOH (38 mL, 1 vol.) was added, and the resulting suspension was cooled to 23° C. over 1 h. After stirring for 0.5 h at 23° C., the solid was filtered off and washed with water (38 ml, 1 vol.), and MeOH (38 mL, 1 vol.). 4-((5-Bromo-4-chloro-1H-pyrrolo[2,3-b]pyridin-2-yl) methyl)morpholine as a light brown powder 4-((5-bromo-4-chloro-1H-pyrrolo[2,3-b]pyridin-2-yl)methyl)morpholine was obtained after drying under vacuum at 50° C. (32.8 g, 86% yield): LCMS calculated for $C_{12}H_{14}BrClN_5O$ [M+H]$^+$: 329.99; Found: 329.8; $^1$H NMR (400 MHz, DMSO-d$_6$) δ 12.22 (s, 1H), 8.34 (s, 1H), 6.40 (s, 1H), 3.65 (s, 2H), 3.58 (m, 4H), 2.42 (m, 4H).

Step 5: Synthesis of 4-((5-bromo-4-chloro-1-(phenylsulfonyl)-1H-pyrrolo[2,3-b]pyridin-2-yl) methyl) morpholine A slurry of 4-((5-Bromo-4-chloro-1H-pyrrolo[2,3-b]pyridin-2-yl)methyl)morpholine (10 g, 30.25 mmol, 1.0 eq., assay 94%-w/w) and NaH (1.69 g, 60%, 42.35 mmol, 1.4 eq.) in 38 mL of tetrahydrofuran was cooled to 0-5° C. as PhSO$_2$Cl (7.48 g, 42.35 mmol, 1.4 eq.) was added over 1 h. After 1.5 h, HPLC indicated the reaction was not complete. Additional NaH (0.34 g, 0.3 eq.) was added, whereupon gas evolution was observed. When HPLC showed the reaction was complete, the reaction mixture was quenched with acetic acid (0.5 g) and a mixture of water (15 mL) and methanol (15 mL). The pH was adjusted to 6.5 with caustic soda and the product was isolated by filtration. The wet cake was washed with 2-isopropanol (20 mL) and water (20 mL) and the wet product (14.8 g) was dried in the vacuum cabinet to give 4-((5-bromo-4-chloro-1-(phenylsulfonyl)-1H-pyrrolo[2,3-b]pyridin-2-yl)methyl)morpholine as a brown solid (12.57 g, 86% yield): LCMS calculated for $C_{18}H_{18}BrClN_3O_3S$ [M+H]$^+$: 469.99; Found: 470.0; $^1$H NMR (400 MHz, DMSO-d$_6$) δ 8.56 (s, 1H), 8.33 (m, 2H), 7.73 (m, 1H), 7.65 (m, 2H), 6.83 (s, 1H), 3.91 (s, 2H), 3.53 (m, 4H), 2.46 (m, 4H).

Step 6: Synthesis of 4-chloro-2-(morpholinomethyl)-1-(phenylsulfonyl)-1H-pyrrolo[2,3-b]pyridine-5-carbaldehyde To a suspension of 4-((5-bromo-4-chloro-1-(phenylsulfonyl)-1H-pyrrolo[2,3-b]pyridin-2-yl)methyl)morpholine (5.0 g, 10.6 mmol, 1.0 eq.) in 50 mL tetrahydrofuran at −10° C. to 0° C. was added iPrMgCl (6.9 mL, 2M in tetrahydrofuran, 13.80 mmol, 1.3 eq.). After stirring for 2 h N, N-dimethylformamide (1.55 g, 21.2 mmol, 2.0 eq.) was added to the reaction solution over 0.5 h at −5° C. to 0° C. The mixture was stirred for 0.5 h at −5° C. to 0° C., then warmed to 23° C. over 0.5 h and stirred for 1 h at 23° C. The pH was adjusted to 6-7 by adding 1.5 mL acetic acid and 10 mL water. To the biphasic mixture was added 25 mL MeOH and 15 mL water. After stirring for 1 h, the product was filtered off and washed with 20 mL MeOH/water (1/1) and 30 mL water. After drying under vacuum at 50° C., 4-chloro-2-(morpholinomethyl)-1-(phenylsulfonyl)-1H-pyrrolo[2,3-b] pyridine-5-carbaldehyde was obtained as an off-white powder (3.39 g, 76% yield): LCMS calculated for $C_{19}H_{19}ClN_3O_4S$ [M+H]$^+$: 420.07; Found: 420.0; $^1$H NMR (400 MHz, DMSO-d$_6$) δ 10.33 (s, 1H), 8.76 (s, 1H), 8.42 (m, 2H), 7.74 (m, 1H), 7.65 (m, 2H), 6.98 (s, 1H), 3.96 (m, 4H), 3.564 (m, 4H), 2.51 (m, 4H).

Example 4. Synthesis of 2,6-difluoro-3,5-dimethoxyaniline

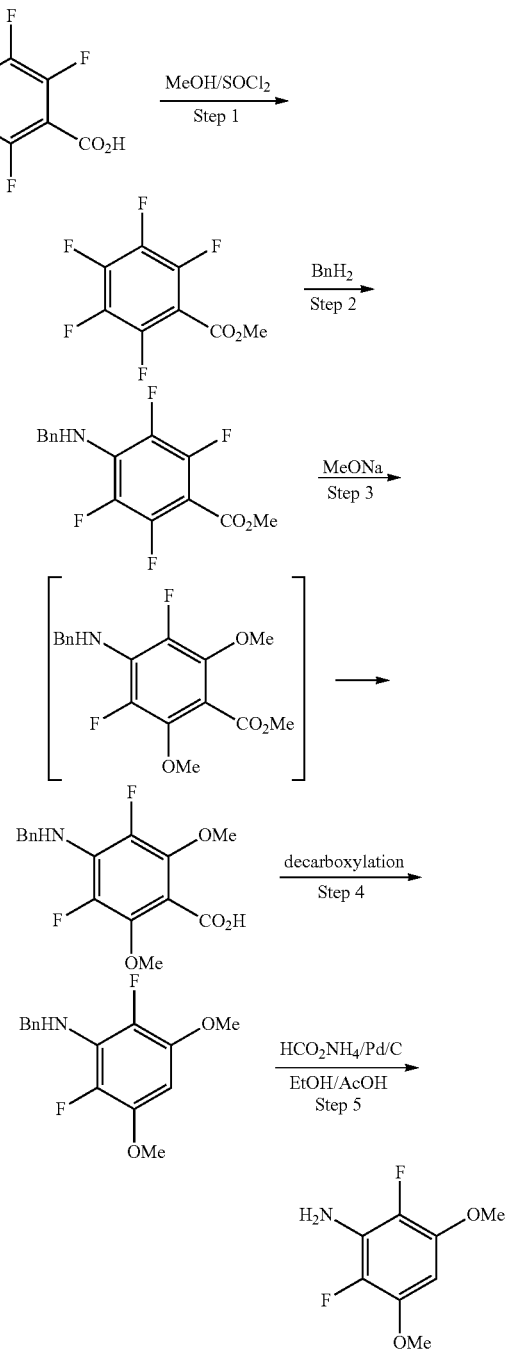

Step 1: Synthesis of methyl pentafluorobenzoate

To a solution of pentafluorobenzoic acid (40 Kg, 188.6 mol) in 68 L of methanol was added SOCl$_2$ (29.2 Kg, 245.2 mol, 1.3 eq.) drop-wise over 4.0 h at 20-50° C. The mixture was then heated to reflux for 17 h. Methanol was removed by vacuum distillation, and the residue was dissolved in methyl t-butyl ether (77 L). The solution was washed with saturated NaHCO$_3$ (37 L), dried over MgSO$_4$, and evaporated to give methyl pentafluorobenzoate as a colorless oil (39 kg, 91% yield): $^1$H NMR (400 MHz, CDCl$_3$) δ 3.90 (s, 3H).

Step 2: Synthesis of methyl-4-(benzylamino)-2,3,5,6-tetrafluorobenzoate

Methyl pentafluorobenzoate (39 Kg, 172.5 mol) and N,N-diisopropyl ethylamine (26.8 Kg, 207 mol, 1.2 eq.) were dissolved in N-methylpyrrolidinone (39 L). A solution of benzylamine (18.5 Kg, 172.5 mol, 1.0 eq.) in 19.5 L of N-methylpyrrolidinone was added drop-wise over 3.5 h while maintaining the internal temperature below 50° C. The resulting thick yellow slurry was heated to 65° C. and stirred another 1 h. The mixture was poured into a 195 L solution of aqueous acetic acid (10% acetic acid and 90% H$_2$O), and the slurry was stirred for 1 h and filtered. The filter cake was washed with water and heptane, and dried at 35° C. under vacuum to give Methyl-4-(benzylamino)-2,3,5,6-tetrafluorobenzoate (38 Kg, 70% yield): $^1$H NMR (400 MHz, CDCl$_3$) δ 7.37 (m, 5H), 4.67 (m, 2H), 4.58 (m, 1H), 3.93 (s, 3H).

Step 3: Synthesis of 4-(benzylamino)-3,5-difluoro-2,6-dimethoxybenzoic acid

Methyl-4-(benzylamino)-2,3,5,6-tetrafluorobenzoate (38 Kg, 121.3 mol) in methanol (72 L), was stirred at room temperature under N$_2$ as a solution of NaOMe in methanol (25 wt %, 110.8 Kg, 545.85 mol, 4.5 eq.) was added drop-wise over 3.0 h while maintaining a temperature below 50° C. After heating to 65-70° C. for 18 h, 18 L of water was added to the reaction mixture and the resulting solution was stirred 1 h. The solvent was removed by vacuum distillation. Water (54 L) was added and the resulting solution was acidified to pH 2 with 37% HCl. The mixture was extracted three times with ethyl acetate (54 Kg each). The combined organic extracts were washed with water (43 L) and concentrated to dryness to form a solid. The solid was triturated with heptane (43 L) to remove the impurities. The solid was collected and dried at 40° C. under vacuum to give 4-(benzylamino)-3,5-difluoro-2,6-dimethoxybenzoic acid (35 Kg, 86% yield): $^1$H NMR (400 MHz, CDCl$_3$) δ 12.74 (s, 1H), 7.37 (m, 5H), 6.62 (s, 1H), 4.67 (m, 2H), 3.96 (s, 6H).

Step 4: Synthesis of n-benzyl-2,6-difluoro-3,5-dimethoxyaniline 4-(Benzylamino)-3,5-difluoro-2,6-dimethoxybenzoic acid (17 Kg) was heated neat to 75-85° C. under nitrogen atmosphere for 3-4 h. After the reaction was completed, 40 L of methyl t-butyl ether and 20 L of 1M NaOH were added. The mixture was stirred at room temperature for 30 min. The organic layer was separated, and was washed with water (20 L) and brine (20 L). The organic phase was concentrated under reduced pressure to give the crude product. The crude was triturated with heptane and dried at 35° C. under vacuum to give N-benzyl-2,6-difluoro-3,5-dimethoxyaniline (12 Kg, 82% yield): $^1$H NMR (400 MHz, CDCl$_3$) δ 7.35 (m, 5H), 6.09 (m, 1H), 4.53 (m, 2H), 4.00 (s, 1H), 3.85 (s, 6H).

Step 5: Synthesis of 2,6-difluoro-3,5-dimethoxyaniline

N-Benzyl-2,6-difluoro-3,5-dimethoxyaniline (24 Kg, 85.9 mol) was dissolved in mixed solvents of ethanol (120 L) and acetic acid (20 L) as ammonium formate (13.2 Kg), and 1.68 Kg of Pd/C was added. The mixture was heated at 50° C. for 2-3 h. The reaction mixture was then filtered through a pad of Celite®, and washed with ethanol (1.2 L×2) and concentrated. The crude was added to 80 L of water, and the resulting slurry was filtered. The crude was added to 60 L methyl t-butyl ether and 2.5 Kg activated carbon, and the mixture was heated to reflux for 3 h. After filtration, and concentration, the resulting solid was added to 36 L heptane and stirred for 2 h at room temperature. The mixture was filtered and dried at 35° C. under vacuum to give 2,6-difluoro-3,5-dimethoxyaniline as a light brown solid (15.2 Kg, 93% yield): LCMS calculated for C$_8$H$_{10}$F$_2$NO$_2$ [M+H]$^+$: 190.16; Found: 190.1; $^1$H NMR (400 MHz, DMSO-d$_6$) δ 6.16 (m, 1H), 5.18 (s, 2H), 3.78 (s, 6H).

Example 5. Alternative Synthesis of 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one (Compound 1)

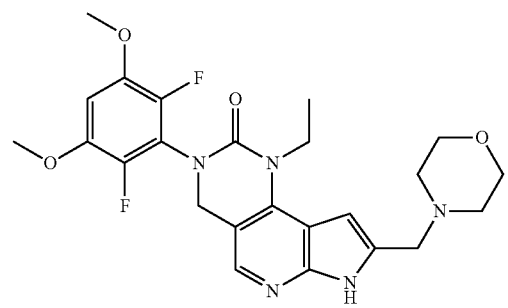 [SMILES: CCN1C(=O)N(c2c(F)c(OC)cc(OC)c2F)Cc2cnc3[nH]c(CN4CCOCC4)cc3c21]

Step 1: 4-(ethylamino)-1H-pyrrolo[2,3-b]pyridine-5-carbaldehyde

A mixture of 4-chloro-1H-pyrrolo[2,3-b]pyridine-5-carbaldehyde (CAS #958230-19-8, Lakestar Tech, Lot: 124-132-29: 3.0 g, 17 mmol) and ethylamine (10M in water, 8.3 mL, 83 mmol) in 2-methoxyethanol (20 mL, 200 mmol) was heated to 130° C. and stirred overnight. The mixture was cooled to room temperature then concentrated under reduced pressure. The residue was treated with 1N HCl (30 mL) and stirred at room temperature for 1 h then neutralized with saturated NaHCO$_3$ aqueous solution. The precipitate was collected via filtration then washed with water and dried to provide the desired product (2.9 g, 92%). LC-MS calculated for $C_{10}H_{12}N_3O$ [M+H]$^+$ m/z: 190.1; found: 190.1.

Step 2: 5-{[(2,6-difluoro-3,5-dimethoxyphenyl)amino]methyl}-N-ethyl-1H-pyrrolo[2,3-b]pyridin-4-amine

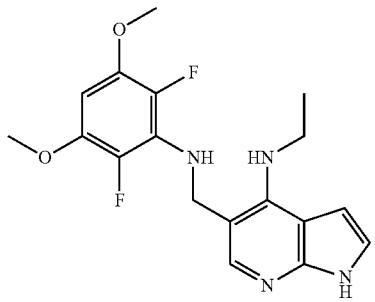 [SMILES: CCNc1c(CNc2c(F)c(OC)cc(OC)c2F)cnc2[nH]ccc12]

A mixture of 4-(ethylamino)-1H-pyrrolo[2,3-b]pyridine-5-carbaldehyde (7.0 g, 37 mmol), 2,6-difluoro-3,5-dimethoxyaniline (9.1 g, 48 mmol) and [(1S)-7,7-dimethyl-2-oxobicyclo[2.2.1]hept-1-yl]methanesulfonic acid (Aldrich, cat #21360: 2 g, 7 mmol) in xylenes (250 mL) was heated to reflux with azeotropic removal of water using Dean-Stark for 2 days at which time LC-MS showed the reaction was complete. The mixture was cooled to room temperature and the solvent was removed under reduced pressure. The residue was dissolved in tetrahydrofuran (500 mL) and then 2.0 M lithium tetrahydroaluminate in THF (37 mL, 74 mmol) was added slowly and the resulting mixture was stirred at 50° C. for 3 h then cooled to room temperature. The reaction was quenched by addition of water, 15% aqueous NaOH and water. The mixture was filtered and washed with THF. The filtrate was concentrated and the residue was washed with $CH_2Cl_2$ and then filtered to get the pure product (11 g, 82%). LC-MS calculated for $C_{18}H_{21}F_2N_4O_2$[M+H]$^+$ m/z: 363.2; found: 363.1.

Step 3: 3-(2,6-Difluoro-3,5-dimethoxyphenyl)-1-ethyl-1,3,4,7-tetrahydro-2H-pyrrolo[3',2':5,6]pyrido[4,3-d]pyrimidin-2-one

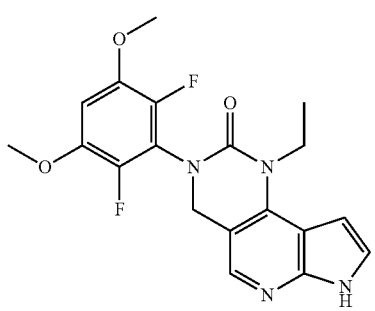 [SMILES: CCN1C(=O)N(c2c(F)c(OC)cc(OC)c2F)Cc2cnc3[nH]ccc3c21]

A solution of triphosgene (5.5 g, 18 mmol) in tetrahydrofuran (30 mL) was added slowly to a mixture of 5-{[(2,6-difluoro-3,5-dimethoxyphenyl)amino]methyl}-N-ethyl-1H-pyrrolo[2,3-b]pyridin-4-amine (5.6 g, 15 mmol) in tetrahydrofuran (100 mL) at 0° C. and then the mixture was stirred at room temperature for 6 h. The mixture was cooled to 0° C. and then 1.0 M sodium hydroxide in water (100 mL, 100 mmol) was added slowly. The reaction mixture was stirred at room temperature overnight and the formed precipitate was collected via filtration, washed with water, and then dried to provide the first batch of the purified desired product. The organic layer in the filtrate was separated and the aqueous layer was extracted with methylene chloride. The combined organic layer was concentrated and the residue was triturated with methylene chloride then filtered and dried to provide another batch of the product (total 5.5 g, 92%). LC-MS calculated for $C_{19}H_{19}F_2N_4O_3$[M+H]$^+$ m/z: 389.1; found: 389.1.

Step 4: 3-(2,6-difluoro-3,5-dimethoxyphenyl)-1-ethyl-7-(phenylsulfonyl)-1,3,4,7-tetrahydro-2H-pyrrolo[3',2':5,6]pyrido[4,3-d]pyrimidin-2-one

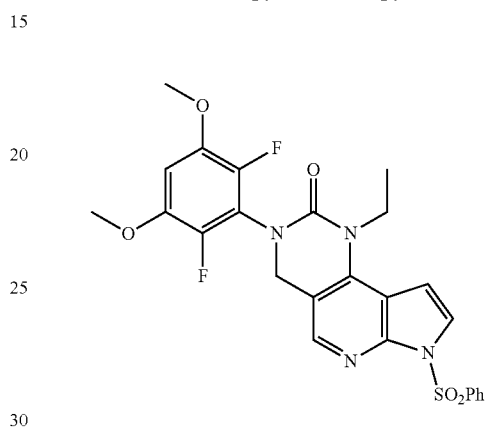

To a solution of 3-(2,6-difluoro-3,5-dimethoxyphenyl)-1-ethyl-1,3,4,7-tetrahydro-2H-pyrrolo[3',2':5,6]pyrido[4,3-d]pyrimidin-2-one (900 mg, 2.32 mmol) in N,N-dimethylformamide (20 mL) cooled to 0° C. was added sodium hydride (185 mg, 4.63 mmol, 60 wt % in mineral oil). The resulting mixture was stirred at 0° C. for 30 min then benzenesulfonyl chloride (0.444 mL, 3.48 mmol) was added. The reaction mixture was stirred at 0° C. for 1.5 h at which time LC-MS showed the reaction completed to the desired product. The reaction was quenched with saturated NH$_4$Cl solution and diluted with water. The white precipitate was collected via filtration then washed with water and hexanes, dried to afford the desired product (1.2 g, 98%) as a white solid which was used in the next step without further purification. LC-MS calculated for $C_{25}H_{23}F_2N_4O_5S$ [M+H]$^+$ m/z: 529.1; found: 529.1.

Step 5: 3-(2,6-difluoro-3,5-dimethoxyphenyl)-1-ethyl-2-oxo-7-(phenylsulfonyl)-2,3,4,7-tetrahydro-1H-pyrrolo[3',2':5,6]pyrido[4,3-d]pyrimidine-8-carbaldehyde

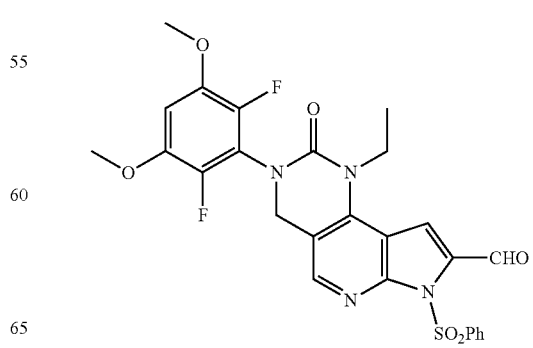

To a solution of 3-(2,6-difluoro-3,5-dimethoxyphenyl)-1-ethyl-7-(phenylsulfonyl)-1,3,4,7-tetrahydro2H-pyrrolo[3',2':5,6]pyrido[4,3-d]pyrimidin-2-one (1.75 g, 3.31 mmol) in tetrahydrofuran (80 mL) at −78° C. was added freshly prepared lithium diisopropylamide (1M in tetrahydrofuran (THF), 3.48 mL, 3.48 mmol). The resulting mixture was stirred at −78° C. for 30 min then N,N-dimethylformamide (1.4 mL, 18 mmol) was added slowly. The reaction mixture was stirred at −78° C. for 30 min then quenched with water and extracted with EtOAc. The organic extracts were combined then washed with water and brine. The organic layer was dried over $Na_2SO_4$ and concentrated. The residue was purified by flash chromatography eluted with 0 to 20% EtOAc in DCM to give the desired product as a white solid (1.68 g, 91%). LC-MS calculated for $C_{26}H_{23}F_2N_4O_6S$ (M+H)$^+$ m/z: 557.1; found: 556.9.

Step 6: 3-(2,6-difluoro-3,5-dimethoxyphenyl)-1-ethyl-8-(morpholin-4-ylmethyl)-7-(phenylsulfonyl)-1,3,4,7-tetrahydro-2H-pyrrolo[3',2':5,6]pyrido[4,3-d]pyrimidin-2-one

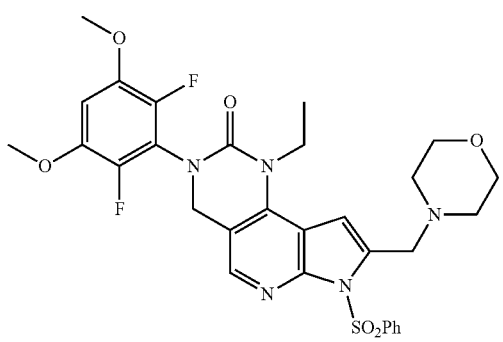

To a solution 3-(2,6-difluoro-3,5-dimethoxyphenyl)-1-ethyl-2-oxo-7-(phenylsulfonyl)-2,3,4,7-tetrahydro-1H-pyrrolo[3',2':5,6]pyrido[4,3-d]pyrimidine-8-carbaldehyde (1.73 g, 3.11 mmol) in dichloromethane (50 mL) was added morpholine (0.95 mL, 11 mmol), followed by acetic acid (2 mL, 30 mmol). The resulting yellow solution was stirred at room temperature overnight then sodium triacetoxyborohydride (2.3 g, 11 mmol) was added. The mixture was stirred at room temperature for 3 h at which time LC-MS showed the reaction went to completion to the desired product. The reaction was quenched with saturated $NaHCO_3$ then extracted with ethyl acetate (EtOAc). The organic extracts were combined then washed with water and brine. The organic layer was dried over $Na_2SO_4$ and concentrated. The residue was purified by flash chromatography eluted with 0 to 40% EtOAc in DCM to give the desired product as a yellow solid (1.85 g, 95%). LC-MS calculated for $C_{30}H_{32}F_2N_5O_6S$ (M+H)$^+$ m/z: 628.2; found: 628.0.

Step 7: 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one To a solution of 3-(2,6-difluoro-3,5-dimethoxyphenyl)-1-ethyl-8-(morpholin-4-ylmethyl)-7-(phenylsulfonyl)-1,3,4,7-tetrahydro-2H-pyrrolo[3',2':5,6]pyrido[4,3-d]pyrimidin-2-one (1.5 g, 2.4 mmol) in tetrahydrofuran (40 mL) was added tetra-n-butylammonium fluoride (1M in THF, 7.2 mL, 7.2 mmol). The resulting solution was stirred at 50° C. for 1.5 h then cooled to room temperature and quenched with water. The mixture was extracted with dichloromethane (DCM) and the organic extracts were combined then washed with water and brine. The organic layer was dried over $Na_2SO_4$ and concentrated. The residue was purified by flash chromatography eluted with 0 to 10% MeOH in DCM to give the desired product as a white solid, which was further purified by prep HPLC (pH=2, acetonitrile/$H_2O$). LC-MS calculated for $C_{24}H_{28}F_2N_5O_4$(M+H)$^+$ m/z: 488.2; found: 488.0. $^1$H NMR (500 MHz, DMSO) δ 12.09 (s, 1H), 8.06 (s, 1H), 7.05 (t, J=8.1 Hz, 1H), 6.87 (s, 1H), 4.78 (s, 2H), 4.50 (s, 2H), 4.17 (q, J=6.8 Hz, 2H), 3.97 (br, 2H), 3.89 (s, 6H), 3.65 (br, 2H), 3.37 (br, 2H), 3.15 (br, 2H), 1.37 (t, J=6.8 Hz, 3H).

Example 6. Synthesis of 7-(2,6-difluoro-3,5-dimethoxy-phenyl)-9-ethyl-2-morpholin-4-ylmethyl-8-oxo-6,7,8,9-tetrahydro-3,4,7,9-tetraaza-cyclopenta[a]naphthalene-3-sulfonic acid dimethylamide

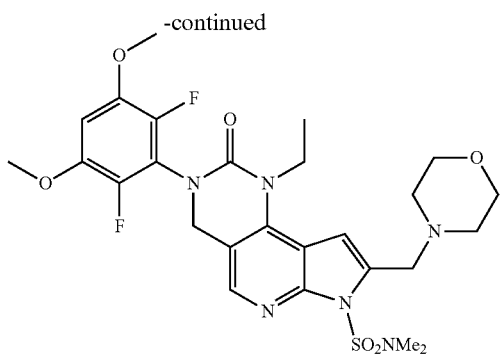

Step 1. Synthesis of 7-(2,6-Difluoro-3,5-dimethoxy-phenyl)-9-ethyl-8-oxo-6,7,8,9-tetrahydro-3,4,7,9-tetraaza-cyclopenta[a]naphthalene-3-sulfonic acid dimethylamide

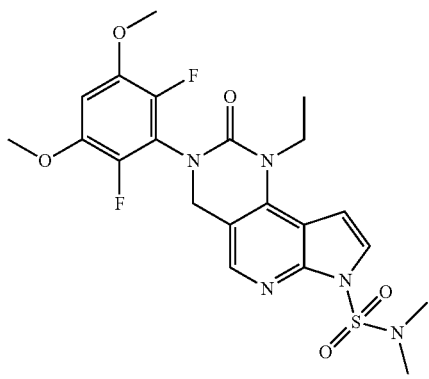

A 200 L glass reactor was assembled with overhead stirring, condenser, thermocouple, addition funnel, and a nitrogen inlet and the apparatus was purged with nitrogen. Potable water (3.1 L) and sodium hydroxide (3093 g) were charged to the reactor and the mixture was stirred at about 71° C. until a solution was obtained. The reaction mixture was cooled to about 30° C. and THF (15.0 L) was added. The reaction mixture was cooled to 10° C. and 3-(2,6-difluoro-3,5-dimethoxyphenyl)-1-ethyl-1,3,4,7-tetrahydro-2H-pyrrolo[3',2':5,6]pyrido[4,3-d]pyrimidin-2-one (3000 g) and n-Bu$_4$N$^+$HSO4$^-$ (262 g) were added sequentially while maintaining the temperature at about 10° C. The materials were rinsed into the reactor with THF (15.0 L) while maintaining the temperature at about 7° C. N,N-dimethylsulfamoyl chloride (1.244 L) was added while maintaining the temperature at about 7° C. The reaction mixture was heated to about 17° C. and stirred for 7 h at about 22° C. Potable water (120.0 L) was charged while maintaining the temperature at about 20° C., and the reaction mixture was stirred for 1 h at about 18° C. The reaction mixture was filtered and the filter cake was washed four times with potable water (30.0 L for each wash). The product was air-dried on the filter for 14.5 hours to afford crude 3-(2,6-difluoro-3,5-dimethoxyphenyl)-1-ethyl-N,N-dimethyl-2-oxo-1,2,3,4-tetrahydro-7H-pyrrolo[3',2':5,6]pyrido[4,3-d]pyrimidine-7-sulfonamide (4694 g).

Purification: A 100 L glass reactor was assembled with overhead stirring, condenser, thermocouple, addition funnel, and a nitrogen inlet and the apparatus was purged with nitrogen. A chromatography column was loaded with CH$_2$Cl$_2$ (37.5 L) and silica gel (15,000 g) and mixed thoroughly and eluted to the surface of the silica gel. Sea sand (4000 g) and magnesium sulfate (6000 g) were charged sequentially to the column. The crude 3-(2,6-difluoro-3,5-dimethoxy-phenyl)-1-ethyl-N,N-dimethyl-2-oxo-1,2,3,4-tetrahydro-7H-pyrrolo[3',2':5,6]pyrido[4,3-d]pyrimidine-7-sulfonamide (6118 g) and CH$_2$Cl$_2$ (22.5 L) were mixed thoroughly until a solution was obtained and then the solution was charged to the column. The elution rate was found to be too slow, so the magnesium sulfate and the solution were removed from the column and filtered. The filter cake was washed with CH$_2$Cl$_2$ (20 L) and the filtrate was charged to the column. The container was rinsed with CH$_2$Cl$_2$ (2.5 L) and the rinse was charged to the column. The column was eluted with 5% EtOAc/CH$_2$Cl$_2$ (prepared separately from 9.4 L of EtOAc and 178.1 L of CH$_2$Cl$_2$). The desired fractions were partially concentrated (using 2 rotavapors for convenience) under vacuum at about 45° C. to a target total volume remaining of 24 L (~4 L per kg of 3-(2,6-difluoro-3,5-dimethoxyphenyl)-1-ethyl-N,N-dimethyl-2-oxo-1,2,3,4-tetrahydro-7H-pyrrolo[3',2':5,6]pyrido[4,3-d]pyrimidine-7-sulfonamide charged). The distillation residue (24 L) was charged to the 100 L reactor and the temperature was adjusted to about 28° C. Heptane (54 L) was charged and the reaction mixture was stirred for 1 hour at about 24° C. The reaction mixture was filtered and the filter cake was washed with heptane (24 L). The product was air-dried on the filter for about 3 hours to afford the product (5382 g). LCMS calculated for C$_{21}$H$_{23}$F$_2$N$_5$O$_5$S [M+H]$^+$: 495.5; Found: 495.1. $^1$H NMR (400 MHz, DMSO-d$_6$) δ 8.12 (s, 1H), 7.72 (s, 1H), 7.07 (t, 1H), 6.89 (s, 1H), 4.83 (s, 2H), 4.14 (t, 2H), 3.91 (s, 6H), 2.96 (s, 6H), 1.35 (t, 3H).

Step 2. Synthesis of 7-(2,6-Difluoro-3,5-dimethoxy-phenyl)-9-ethyl-2-formyl-8-oxo-6,7,8,9-tetrahydro-3,4,7,9-tetraaza-cyclopenta[a]naphthalene-3-sulfonic acid dimethylamide

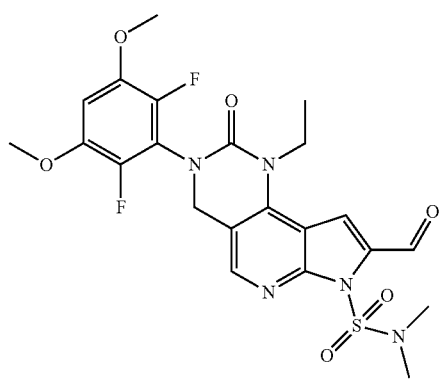 [SMILES: CCN1C(=O)N(c2c(F)c(OC)cc(OC)c2F)Cc2cnc3c(cc(C=O)n3S(=O)(=O)N(C)C)c21]

A 22 L glass reactor and a 200 L glass reactor were assembled with overhead stirring, condenser, thermocouple, addition funnel, and a nitrogen inlet and each apparatus was purged with nitrogen. THF (2.38 L) and N,N-diisopropylamine (0.82 L) were charged to the 22 L glass reactor and the mixture was cooled to −72° C. 2.5 M solution of n-BuLi in hexanes (2.13 L) was charged while maintaining the temperature at about −70° C. The reaction mixture was stirred at −71° C. for about 7 minutes and warmed to −2° C. over 3.5 h to form a 1 M LDA solution.

3-(2,6-Difluoro-3,5-dimethoxyphenyl)-1-ethyl-N,N-dimethyl-2-oxo-1,2,3,4-tetrahydro-7H-pyrrolo[3',2':5,6]pyrido[4,3-d]pyrimidine-7-sulfonamide (1075 g gross, 93.07 wt %, 1001 g net) and THF (10.0 L) were charged to the first rotavapor and rotated at about 63° C. for about 28 minutes without solvent collection until a solution was obtained. 3-(2,6-Difluoro-3,5-dimethoxyphenyl)-1-ethyl-N,N-dimethyl-2-oxo-1,2,3,4-tetrahydro-7H-pyrrolo[3',2':5,6]pyrido[4,3-d]pyrimidine-7-sulfonamide (1075 g gross, 93.07 wt %, 1001 g net) and THF (10.0 L) were charged to the second rotavapor and rotated at about 61° C. for about 35 minutes without solvent collection until a solution was obtained. Both mixtures were concentrated at about 50° C. under reduced pressure. THF (10.0 L per rotavapor) was charged to each rotavapor, and both mixtures were concentrated at about 50° C. under reduced pressure. THF (10.0 L) was charged to the first rotavapor and the mixture was rotated at about 64° C. for 14 minutes without solvent collection until a solution was obtained. THF (10.0 L) was charged to the second rotavapor and the mixture was rotated at about 64° C. for 14 minutes without solvent collection until a solution was obtained. A PCT by GC for residual $CH_2Cl_2$ passed. Both solutions were transferred to the 200 L reactor using THF (26 L) to assist with the transfer. The reaction mixture was cooled to −65° C. The 1 M LDA solution (4.84 L) was charged over about 1 hour while maintaining the temperature at about −64° C., and the reaction mixture was stirred at −65° C. for 2.25 h. DMF (1.56 L) was charged over 30 minutes while maintaining the temperature at about −65° C. The reaction mixture was stirred at −64° C. for 31 minutes and warmed to −12° C. over about 2 hours. Separately, an aqueous ammonium chloride solution was prepared by thoroughly mixing ammonium chloride (160 g) and potable water (1.6 L). The aqueous ammonium chloride solution was charged over 17 minutes while maintaining the temperature at about −5° C., and the reaction mixture was warmed to 19° C. over about 7.5 h. The reaction mixture was partially concentrated (using 2 rotavapors for convenience) under vacuum at about 45° C. A total volume of 36 L was collected by distillation (~18 L collected per kg of 3-(2,6-difluoro-3,5-dimethoxy-phenyl)-1-ethyl-N,N-dimethyl-2-oxo-1,2,3,4-tetrahydro-7H-pyrrolo[3',2':5,6]pyrido[4,3-d]pyrimidine-7-sulfonamide charged). The distillation residues were charged to the 200 L reactor and the temperature was adjusted to about 23° C. and the reaction mixture was stirred at 23° C. for about 2 h. Potable water (20.0 L) was added over about 1 h and the reaction mixture was stirred at about 23° C. The reaction mixture was filtered and the filter cake was washed twice with potable water (10.0 L for each wash). The product was air-dried on the filter for about 3.5 h to afford crude product (2028 g). The crude was slurried in MTBE at 46-53° C. for 1h, then cooled to rt, filtered, washed with more MTBE to give 7-(2,6-Difluoro-3,5-dimethoxy-phenyl)-9-ethyl-2-formyl-8-oxo-6,7,8,9-tetrahydro-3,4,7,9-tetraaza-cyclopenta[a]naphthalene-3-sulfonic acid dimethylamide: LCMS calculated for $C_{22}H_{23}F_2N_5O_6S$ [M+H]$^+$: 524.13; Found: 524.80. $^1$H NMR (400 MHz, DMSO-$d_6$) δ 10.24 (s, 1H), 8.31 (s, 1H), 7.50 (s, 1H), 7.05 (m, 1H), 4.86 (s, 2H), 4.17 (m, 2H), 3.86 (s, 6H), 3.04 (s, 6H), 1.29 (m, 3H).

Step 3. Synthesis of 7-(2,6-Difluoro-3,5-dimethoxyphenyl)-9-ethyl-2-morpholin-4-ylmethyl-8-oxo-6,7,8,9-tetrahydro-3,4,7,9-tetraaza-cyclopenta[a]naphthalene-3-sulfonic acid dimethylamide A 200 L glass reactor was assembled with overhead stirring, condenser, thermocouple, addition funnel, and a nitrogen inlet and the apparatus was purged with nitrogen. Methylene chloride (20.0 L) and 7-(2,6-Difluoro-3,5-dimethoxy-phenyl)-9-ethyl-2-formyl-8-oxo-6,7,8,9-tetrahydro-3,4,7,9-tetraaza-cyclopenta[a]naphthalene-3-sulfonic acid dimethylamide (2000 g) were charged to the reactor and the mixture was stirred at 18° C. until a solution was obtained. Morpholine (1.7 L) was added to the reaction mixture. Acetic acid (2.0 L) was added over 34 minutes while maintaining the temperature at about 32° C. The reaction mixture was stirred at about 27° C. for 4 h. Sodium triacetoxyborohydride (1620 g) was added over 40 minutes while maintaining the temperature at about 28° C. The reaction mixture was stirred at about 24° C. for 2.5 h. Separately, a solution was prepared by thoroughly mixing sodium bicarbonate (2800 g) and potable water (40.0 L) until a solution was obtained. The solution was added over 36 minutes while maintaining the temperature at about 19° C. until a pH was 8-9 was obtained. The reaction mixture was stirred at about 18° C. for 30 minutes. The phases were separated. The organic phase was extracted three times with methylene chloride (10.0 L per extraction). The combined organic phases were washed with potable water (20.0 L). Separately, a solution was prepared by thoroughly mixing sodium chloride (2001 g) and potable water (20.0 L) until a solution was obtained. The organic phase was washed with the sodium chloride solution and dried with $MgSO_4$ (600 g). The reaction mixture was filtered and the filter cake was washed with methylene chloride (6.0 L). The combined filtrate and wash were concentrated under reduced pressure at 38° C. to afford crude 7-(2,6-difluoro-3,5-dimethoxy-phenyl)-9-ethyl-2-morpholin-4-ylmethyl-8-oxo-6,7,8,9-tetrahydro-3,4,7,9-tetraaza-cyclopenta[a]naphthalene-3-sulfonic acid dimethylamide (2200 g). Chromatography with 0-40% EtOAc in DCM gave 7-(2,6-Difluoro-3,5-dimethoxy-phenyl)-9-ethyl-2-morpholin-4-ylmethyl-8-oxo-6,7,8,9-tetrahydro-3,4,7,9-tetraaza-cyclopenta[a]naphthalene-3-sulfonic acid dimethylamide: LCMS calculated for $C_{26}H_{32}F_2N_6O_6S$ [M+H]$^+$: 595.21; Found: 474.2. $^1$H NMR (400 MHz, DMSO-$d_6$) δ 8.10 (s, 1H), 7.05 (t, 1H), 6.81 (s, 1H), 4.80 (s, 2H), 4.12 (m, 2H), 3.91 (s, 6H), 3.79 (s, 2H), 3.57 (m, 4H), 3.10 (s, 6H), 2.50 (m, 4H), 1.35 (m, 3H).

Example 7. Synthesis of 3-(2,6-difluoro-3-hydroxy-5-methoxyphenyl)-1-ethyl-8-(morpholinomethyl)-1,3,4,7-tetrahydro-2H-pyrrolo[3',2':5,6]pyrido[4,3-d]pyrimidin-2-one (Compound 2)

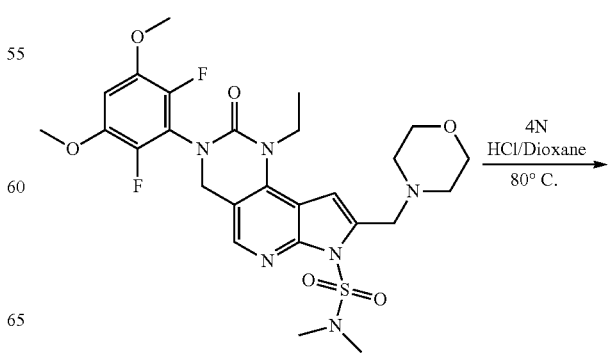

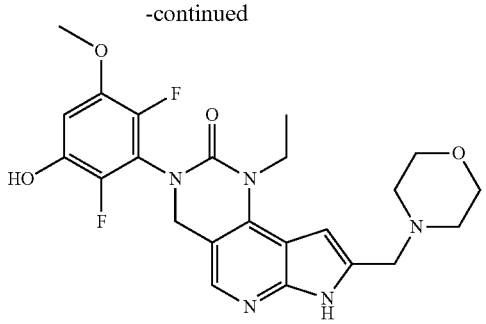

A mixture of 3-(2,6-difluoro-3,5-dimethoxyphenyl)-1-ethyl-N,N-dimethyl-8-(morpholin-4-ylmethyl)-2-oxo-1,2,3,4-tetrahydro-7H-pyrrolo[3',2':5,6]pyrido[4,3-d]pyrimidine-7-sulfonamide (44.88 g, 75.48 mmol) in 1,4-Dioxane (400 mL, 4000 mmol) was stirred under $N_2$ as a mixture of 12.0 M hydrogen chloride in water (1260 mL, 1510 mmol) and water (1260 mL, 6990 mmol) was added via additional funnel (internal temperature went to 35° C.). The resulting solution was heated at 80° C. for 18 h. LC-MS indicated no starting material left. The reaction mixture was cooled to rt, the organic solvent concentrated, and the resultant aqueous HCl solution was diluted with 200 mL of 2N HCl solution. The resultant aqueous solution was extracted with DCM (3×80 mL), and the combined DCM phases were re-extracted with 6N HCl (80 mL). The combined HCl aqueous solution was stirred and cooled to 0-5° C. with ice-water. The acidic solution was neutralized by dropwise addition of 25% NaOH (~200 mL) to pH>12. The resulting solid (the deprotected unreacted starting material or Compound 1) was filtered and washed with water (3×250 mL). The basic aqueous solution was acidified with aqueous HCl to pH~6, and extracted with DCM (3×30 mL). The combined DCM solution was dried over $Na_2SO_4$, and concentrated. The crude was then slurried in MTBE, filtered, washed with more MTBE, and dried in a vacuum oven at 50° C. overnight to give 3-(2,6-difluoro-3-hydroxy-5-methoxyphenyl)-1-ethyl-8-(morpholinomethyl)-1,3,4,7-tetrahydro-2H-pyrrolo[3',2':5,6]pyrido[4,3-d]pyrimidin-2-one (277 mg): LCMS calculated for $C_{23}H_{26}F_2N_5O_4$ $[M+H]^+$: 474.47; Found: 474.2. $^1H$ NMR (400 MHz, DMSO-$d_6$) δ 11.40 (s, 1H), 9.95 (s, 1H), 7.99 (s, 1H), 6.78 (m, 1H), 6.42 (s, 1H), 4.76 (s, 2H), 4.09 (m, 2H), 3.80 (s, 3H), 3.60 (m, 6H), 2.41 (m, 4H), 1.28 (m, 3H).

Example 8. Synthesis of 3-(2,6-difluoro-3,5-bis(methoxy-d3)phenyl)-1-ethyl-8-(morpholinomethyl)-1,3,4,7-tetrahydro-2H-pyrrolo[3',2':5,6]pyrido[4,3-d]pyrimidin-2-one (Compound 6)

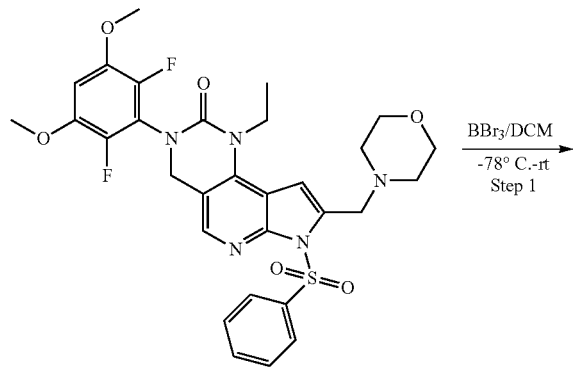

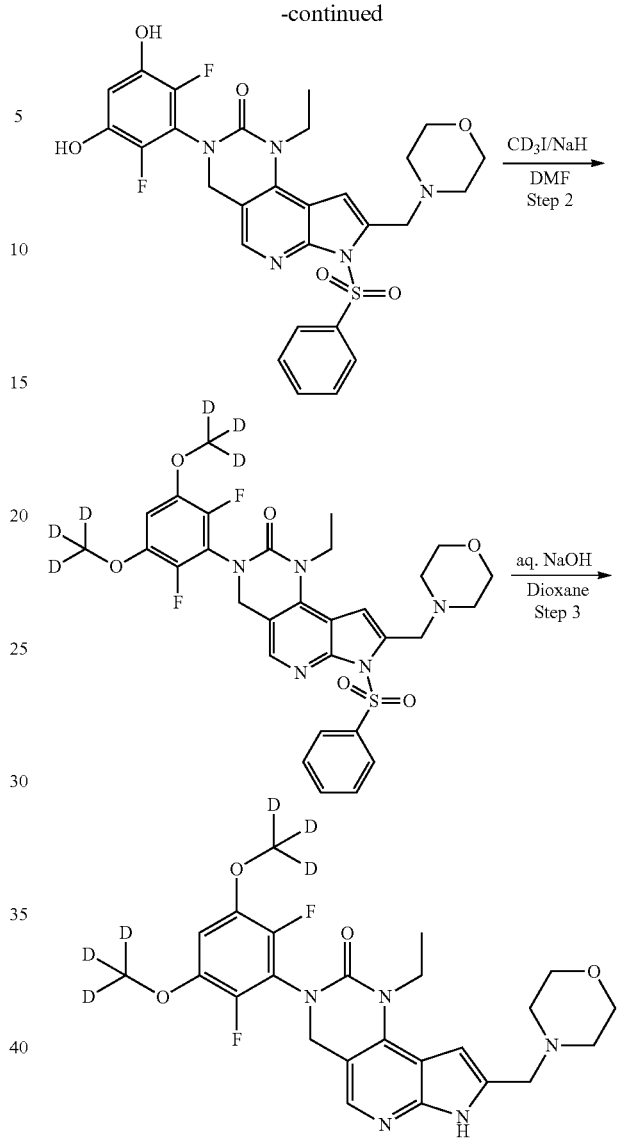

Step 1. Synthesis of 3-(2,6-difluoro-3,5-dihydroxyphenyl)-1-ethyl-8-(morpholinomethyl)-7-(phenylsulfonyl)-1,3,4,7-tetrahydro-2H-pyrrolo[3',2':5,6]pyrido[4,3-d]pyrimidin-2-one A solution of 3-(2,6-difluoro-3,5-dimethoxyphenyl)-1-ethyl-8-(morpholinomethyl)-7-(phenylsulfonyl)-1,3,4,7-tetrahydro-2H-pyrrolo[3',2':5,6]pyrido[4,3-d]pyrimidin-2-one (2.0 g, 3.2 mmol) in 25.0 mL of DCM was stirred at −78° C. as $BBr_3$ (3.10 mL, 10.0 eq.) (neat) was added dropwise. After 30 min, the dry-ice bath was removed and the reaction was slowly warmed to rt. After 2 h, HPLC indicated no more starting material. The reaction was then cooled to 0° C., treated carefully with 20 mL of ice water, and stirred for 30 min. The resulting solid was filtered, washed with more water and dried on a funnel overnight. The crude was treated with 20% MeOH in DCM (10 mL) and stirred for 20 min, then filtered and dried to give 3-(2,6-difluoro-3,5-dihydroxyphenyl)-1-ethyl-8-(morpholinomethyl)-7-(phenylsulfonyl)-1,3,4,7-tetrahydro-2H-pyrrolo[3',2':5,6]pyrido[4,3-d]pyrimidin-2-one as a white solid (1.208 g, 61% yield): LCMS calculated for $C_{28}H_{28}F_2N_5O_6S$ [M+H]$^+$: 600.17; Found: 600.4. The material was used for the next step without further purification.

Step 2. Synthesis of 3-(2,6-difluoro-3,5-bis(methoxy-d3)phenyl)-1-ethyl-8-(morpholinomethyl)-7-(phenylsulfonyl)-1,3,4,7-tetrahydro-2H-pyrrolo[3',2':5,6]pyrido[4,3-d]pyrimidin-2-one 3-(2,6-Difluoro-3,5-dihydroxyphenyl)-1-ethyl-8-(morpholinomethyl)-7-(phenylsulfonyl)-1,3,4,7-tetrahydro-2H-pyrrolo[3',2':5,6]pyrido[4,3-d]pyrimidin-2-one (1.20 g, 2.00 mmol) and NaH (60% dispersion in mineral oil, 216 mg, 9.01 mmol) in DMF (12.4 mL, 160 mmol) was stirred at rt under $N_2$ for 15 min (all went in solution), then MeI-D$^3$ (0.263 mL, 4.20 mmol) was added dropwise. After stirring at rt for 1h, the reaction was cooled to 0° C., 30 mL of ice-water was added, and the resulting solid was stirred for 30 min. The resulting solid was filtered, washed with water and dried. The crude product was purified by Biotage chromatography with 0-6% MeOH in DCM to give 3-(2,6-difluoro-3,5-bis(methoxy-d3)phenyl)-1-ethyl-8-(morpholinomethyl)-7-(phenylsulfonyl)-1,3,4,7-tetrahydro-2H-pyrrolo[3',2':5,6]pyrido[4,3-d]pyrimidin-2-one as a white solid (950 mg, 75% yield): LCMS calculated for $C_{30}H_{26}D_6F_2N_5O_6S$ [M+H]$^+$: 634.23; Found: 634.5. $^1$H NMR (400 MHz, DMSO-d$_6$) δ 8.41 (m, 2H), 8.07 (s, 1H), 7.70 (m, 1H), 7.63 (m, 2H), 7.05 (m, 1H), 6.89 (s, 1H), 4.76 (s, 2H), 4.09 (m, 2H), 3.93 (s, 2H), 3.60 (m, 4H), 2.50 (m, 4H), 1.28 (m, 3H).

Step 3. Synthesis of 3-(2,6-difluoro-3,5-bis(methoxy-d3)phenyl)-1-ethyl-8-(morpholinomethyl)-1,3,4,7-tetrahydro-2H-pyrrolo[3',2':5,6]pyrido[4,3-d]pyrimidin-2-one To a 25 mL flask was added 3-(2,6-difluoro-3,5-bis(methoxy-d3)phenyl)-1-ethyl-8-(morpholinomethyl)-7-(phenylsulfonyl)-1,3,4,7-tetrahydro-2H-pyrrolo[3',2':5,6]pyrido[4,3-d]pyrimidin-2-one (1000 mg, 1.578 mmol) in 1,4-Dioxane (10.0 mL) and 1N sodium hydroxide in water (6312 µl, 6.31 mmol). The solution was heated to 74° C. (internal temperature) for 15 hr. LC-MS indicated the completion of the reaction. The clear light yellow solution was cooled to rt (solids begin to precipitate out of solution as the mixture cools) to give an off-white suspension. Water (10.0 mL) was added at 20-25° C. and the resulting solid was stirred for 30 min. The solid was filtered, washed with water 6 times and the pH of final wash was checked (pH=~7). The crude HNMR of the product (0.70 g) indicated the presence of some dioxane.

The crude 3-(2,6-difluoro-3,5-bis(methoxy-d3)phenyl)-1-ethyl-8-(morpholinomethyl)-1,3,4,7-tetrahydro-2H-pyrrolo[3',2':5,6]pyrido[4,3-d]pyrimidin-2-one (0.70 g, 1.418 mmol) in DCM (3.88 ml, 60.3 mmol) was heated to 22-36° C. and stirred to get a clear solution. After about 5 min, MTBE (0.693 ml, 5.82 mmol) was added. After stirring for about 1 h, a precipitate formed, and the mixture was stirred for an additional 30 min. The mixture was filtered, washed with MTBE, washed with heptane and dried in a vacuum oven under $N_2$ at 50° C. to give the product (0.63 g, 81% yield, 96% HPLC purity). The crude solid was purified using Biotage chromatography with 0-10% MeOH in DCM, the fractions were combined, concentrated, and dried in a vacuum oven at 50° C. to give 3-(2,6-difluoro-3,5-bis(methoxy-d3)phenyl)-1-ethyl-8-(morpholinomethyl)-1,3,4,7-tetrahydro-2H-pyrrolo[3',2':5,6]pyrido[4,3-d]pyrimidin-2-one with 99.5% HPLC purity: LCMS calculated for $C_{24}H_{22}D_6F_2N_5O_4$ [M+H]$^+$: 494.24; Found: 494.2. $^1$H NMR (400 MHz, DMSO-d$_6$) δ 11.75 (S, 1H), 7.99 (s, 1H), 7.05 (m, 1H), 6.89 (s, 1H), 4.76 (s, 2H), 4.09 (m, 2H), 3.60 (m, 6H), 2.50 (m, 4H), 1.28 (m, 3H).

Compound 6 can also be prepared according to Example 1 using 2,6-difluoro-3,5-bis(methoxy-d3)aniline in place of 2,6-difluoro-3,5-dimethoxyaniline. 2,6-difluoro-3,5-bis(methoxy-d3)aniline can be made according to Example 4, Step 3, using sodium methoxide-d3 in place of sodium methoxide.

Example A

FGFR Enzymatic Assay

The inhibitor potency of the exemplified compounds was determined in an enzyme discontinuous assay that measures peptide phosphorylation using FRET measurements to detect product formation. Inhibitors were serially diluted in DMSO and a volume of 0.2 µL was transferred to the wells of a 384-well plate. For the isoforms of FGFR (-1, -2, -3 wild-type and mutant isoforms, -4) including phosphorylated and un-phosphorylated proteins, a 5 µL/well volume of enzyme diluted in assay buffer (50 mM HEPES, 10 mM $MgCl_2$, 1 mM EGTA, 0.01% Tween-20, 5 mM DTT, pH 7.5) was added to the plate and pre-incubated with inhibitor for 5 to 15 minutes at ambient temperature. Appropriate controls (enzyme blank and enzyme with no inhibitor) were included on the plate. The reaction was initiated by the addition of a 5 uL/well volume containing both biotinylated EQEDEPEGDYFEWLE (SEQ ID NO. 1) peptide substrate and ATP in assay buffer. The 10 uL/well reaction concentration of the peptide substrate was 500 nM whereas the ATP concentration was maintained near or below the ATP Km for each FGFR isoform. The ATP Km values were pre-determined for each FGFR isoform in a separate series of experiments. The reaction plate was incubated at 25° C. for 1 hr and the reactions were ended with the addition of 5 µL/well of quench solution (50 mM Tris, 150 mM NaCl, 0.5 mg/mL BSA, pH 7.8; 45 mM EDTA, 600 nM staurosporin, with Perkin Elmer Lance Reagents at 3.75 nM Eu-antibody PY20 and 180 nM APC-Streptavidin). The plate was allowed to equilibrate for ~10 minutes at ambient temperature before scanning on a PheraStar plate reader (BMG Labtech) instrument.

Either GraphPad prism or XLfit was used to analyze the data. The $IC_{50}$ values were derived by fitting the data to a four parameter logistic equation producing a sigmoidal dose-response curve with a variable Hill coefficient.

Prism equation: $Y = Bottom + (Top - Bottom)/(1 + 10^{((Log\ IC_{50} - X)*Hill\ slope))}$;

XLfit equation: $Y = (A + ((B-A)/(1+((X/C)^D))))$ where $X$ is the logarithm of inhibitor concentration and $Y$ is the response.

FGFR inhibition data for various compounds of the disclosure is shown in Table 1 below. The symbol: "+" indicates an $IC_{50}$ less than 10 nM; "++" indicates an $IC_{50}$ greater than or equal to 10 nM but less than 100 nM; "+++" indicates an $IC_{50}$ greater than or equal to 100 nM but less than 500 nM; and "++++" indicates an $IC_{50}$ greater than or equal to 500 nM but less than 1000 nM.

TABLE 1

FGFR Inhibition Data

| Compound | FGFR1 IC50 (nM) | FGFR2 IC50 (nM) | FGFR3 IC50 (nM) |
|---|---|---|---|
| Compound 1 | + | + | + |
| Compound 2 | + | + | + |
| Compound 3 | ++ | ++ | +++ |
| Compound 6 | + | + | + |

Example B: KATOIII Whole Blood pFGFR2α ELISA Assay

To measure tyrosine-phosphorylated Fibroblast Growth Factor Receptor 2 alpha (FGFR2a) in KATO III spiked whole blood assay, KATO III cells were purchased from ATCC and maintained in Iscove's medium with 20% FBS (Gibco/Life Technologies). To measure the inhibition of FGFR2α activity of test compounds, the cells were resuspended with Iscove's, 0.2% FBS at 5×10$^6$ cells/ml. 50 uL of the cells were then spiked into a 96-deep well 2 ml polypropylene assay block (Costar) in the presence or absence of a concentration range of test compounds and 300 ul human heparinized whole blood (Biological Specialty Corp, Colmar PA). After 4 hours incubation in 37° C., the red cells were lysed using Qiagen EL buffer and the cell lysates were resuspended in lysis buffer (Cell Signaling) containing standard protease inhibitor cocktail (Calbiochem/EMD) and PMSF (Sigma) for 30 minutes ice. The lysates were transferred to a standard V bottom propylene tissue culture plate and frozen overnight at −80° C. Samples were tested an in an R & D Systems DuoSet IC Human Phospho-FGF R2a ELISA and the plate was measured using a SpectraMax M5 microplate set to 450 nm with a wavelength correction of 540. IC$_{50}$ determination was performed by fitting the curve of inhibitor percent inhibition versus the log of the inhibitor concentration using the GraphPad Prism 5.0 software.

KATOIII Whole Blood pFGFR2α ELISA IC$_{50}$ data is shown in Table 2 below. The symbol: "+" indicates an IC$_{50}$ less than 50 nM; "++" indicates an IC$_{50}$ greater than or equal to 50 nM but less than 250 nM; "+++" indicates an IC$_{50}$ greater than or equal to 250 nM but less than 500 nM; "++++" indicates an IC$_{50}$ greater than or equal to 500 nM but less than 1000 nM; and "+++++" indicates an IC$_{50}$ greater than or equal to 1000 nM but less than 3000 nM.

TABLE 2

KATOIII Whole Blood pFGFR2α ELISA Data

| Compound | FGFR2_WB_ELISA-KATOIII IC50 (nM) |
|---|---|
| Compound 1 | + |
| Compound 2 | ++ |
| Compound 3 | +++++ |
| Compound 6 | ND |
| Compound 7 | + |

Example C: Determination of Permeability and P-gp Mediated Transport in Caco-2 Cells Caco-2 cells were grown in 96-well transwell plates with a seeding density of 14000 cell/well in DMEM medium. To determine the permeability in the absorptive direction (A-B), the test compound in HBSS was added to the donor compartment (apical side), and 4% BSA in HBSS was added into the receiver compartment (basolateral side). To determine whether a compound is a P-gp substrate, permeability values were measured in both the A-B and B-A directions (bidirectional transport assay) in the absence of 4% BSA. Digoxin and cyclosporine A were included as positive controls for P-gp substrate and inhibitor, respectively, to ensure the functionality of P-gp in the bidirectional transport assay. The test compound at various concentrations was added in the donor compartment (apical side for A-B transport and basolateral side for B-A transport) while HBSS solution was added in the receiver compartment (basolateral side for A-B transport and apical side for B-A transport). For permeability studies in the A-B direction, the donor volume was 0.075 mL, and the receiver volume was 0.25 mL. For permeability studies in the B-A direction, the donor volume was 0.25 mL, and the receiver volume was 0.075 mL. The incubation was carried out at 37° C. for 120 minutes. Transepithelial electrical resistance (TEER) was measured before and after the 120 minutes incubation to ensure the integrity of the cell monolayers. At the end of the incubation period, samples were removed from both the donor and receiver sides and mixed with acetonitrile for protein precipitation. The supernatants were collected after centrifugation for analysis using LC-MS/MS method. Permeability coefficient (Papp) values from Caco-2 studies were determined using the following equation:

$$Papp(cm/s) = (F*VD)/(SA*MD)$$

where the flux rate (F, mass/time) was calculated from the slope of cumulative amounts of compound of interest on the receiver side, SA is the surface area of the cell membrane, VD is the donor volume, and MD is the initial amount of the solution in the donor chamber.

The efflux ratio from Caco-2 studies was calculated as the ratio of the Papp measured in the B-A direction divided by the Papp in the A-B direction.

Permeability data in Caco-2 Cells for various compounds of the disclosure are shown in Table 3 below.

TABLE 3

Permeability in Caco-2 Cells

| Compound | CACO2 Pm (×10E−6 cm/s) |
|---|---|
| Compound 1 | 11 |
| Compound 2 | 0.5 |
| Compound 3 | ND |
| Compound 6 | 16 |

P-gp mediated transport data in Caco-2 cells for various compounds of the disclosure are shown in Table 4 and Table 5 below.

TABLE 4

Bidirectional Transport of Compound 2 Across Caco-2 Monolayers

| Compound 2 Concentration (μM) | Inhibitor Compound | Concentration (μM) | Papp A-B* (×10⁻⁶ cm/s) | Papp B-A* (×10⁻⁶ cm/s) | Efflux Ratio (B-A/A-B)* |
|---|---|---|---|---|---|
| 3 | NA | NA | 0.43 ± 0.15 | 11 ± 8.0 | 25 ± 11 |
|   | CSA | 10 | 0.65 ± 0.11 | 2.2 ± 0.49 | 3.3 ± 1.2 |
| 30 | NA | NA | 0.41 ± 0.07 | 7.7 ± 2.8 | 19 ± 5.2 |
|   | CSA | 10 | 2.0 ± 0.33 | 3.1 ± 1.2 | 1.5 ± 0.59 |

NA = not applicable;
CSA = cyclosporine A;
*N = 3

TABLE 5

Bidirectional Transport of Compound 1 Across Caco-2 Monolayers

| Compound 1 Concentration (μM) | Inhibitor Compound | Concentration (μM) | Papp A-B* (×10⁻⁶ cm/s) | Papp B-A* (×10⁻⁶ cm/s) | Efflux Ratio (B-A/A-B)* |
|---|---|---|---|---|---|
| 1 | NA | NA | 7.3 ± 1.6 | 11 ± 0.95 | 1.5 ± 0.35 |
|   | CSA | 5 | 12 ± 2.3 | 9.0 ± 1.8 | 0.73 ± 0.17 |
| 30 | NA | NA | 21 ± 1.1 | 13 ± 1.6 | 0.64 ± 0.07 |
|   | CSA | 5 | 18 ± 0.75 | 12 ± 1.3 | 0.63 ± 0.07 |

NA = not applicable;
CSA = cyclosporine A;
*N = 3-6

The efflux ratio of Compound 1 at 30 μM is 0.64. In contrast, the efflux ratio of Compound 2 at 30 μM is 19. This indicates that Compound 2 is a more effective substrate for Pgp transport than Compound 1, and Compound 2 is not well absorbed into the blood stream. Compound 2 can be a candidate for IV administration or hepatic arterial infusion for the treatment of diseases and disorders (e.g., cholangiocarcinoma).

In addition, the permeability of Compound 1 in Caco-2 cells is 11 Pm, while the permeability of Compound 2 in Caco-2 cells is 0.5 Pm. The large differences in permeability and efflux ratios between Compound 1 and Compound 2 is unexpected in light of the small difference in compound structure.

Example D: Compound 1 Human Absorption, Metabolism, and Excretion Study

An open label-study was conducted, assessing the mass balance, pharmacokinetics, and metabolite profiles of a single oral dose of [14C] Compound 1:

[14C] Compound 1

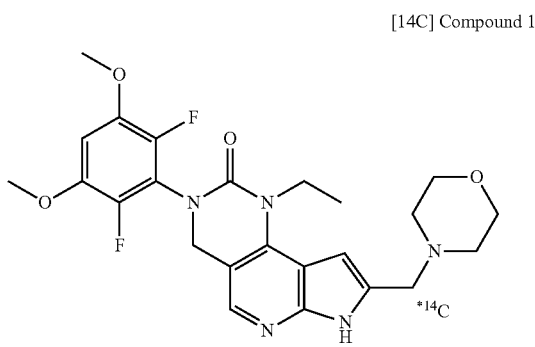 [SMILES: CCN1C(=O)N(c2c(F)c(OC)cc(OC)c2F)Cc2cnc3[nH]c(CN4CCOCC4)cc3c21]

Seven male subjects each received a single, oral dose of 11 mg of Compound 1 tablets along with an [14C] Compound 1 solution (approximately 250 μCi) after an overnight fast. Blood/plasma, urine, and feces were collected from participants for 4 to 10 days after administration.

Human discharge criteria includes that a minimum of 90% of the administered radioactive dose is recovered; and that less than or equal to 1% of the administered radioactive dose is recovered in excreta (urine and feces combined) in 2 consecutive 24-hour urine and fecal collection samples.

12.6% of the dose was recovered in urine, and 82.4% of the dose was recovered in feces. The overall recovery of radioactivity in urine and feces was 95.1% over the 240 hour study. Rapid absorption was observed, with peak total radioactivity and plasma Compound 1 concentrations at about 2.0 hours post dose.

FIG. 1 shows the mean cumulative percent of radioactive dose recovered in urine and feces at specified intervals after a single 13-mg (250 μCi) oral dose of [14C] Compound 1 to healthy male subjects.

Figure 2:
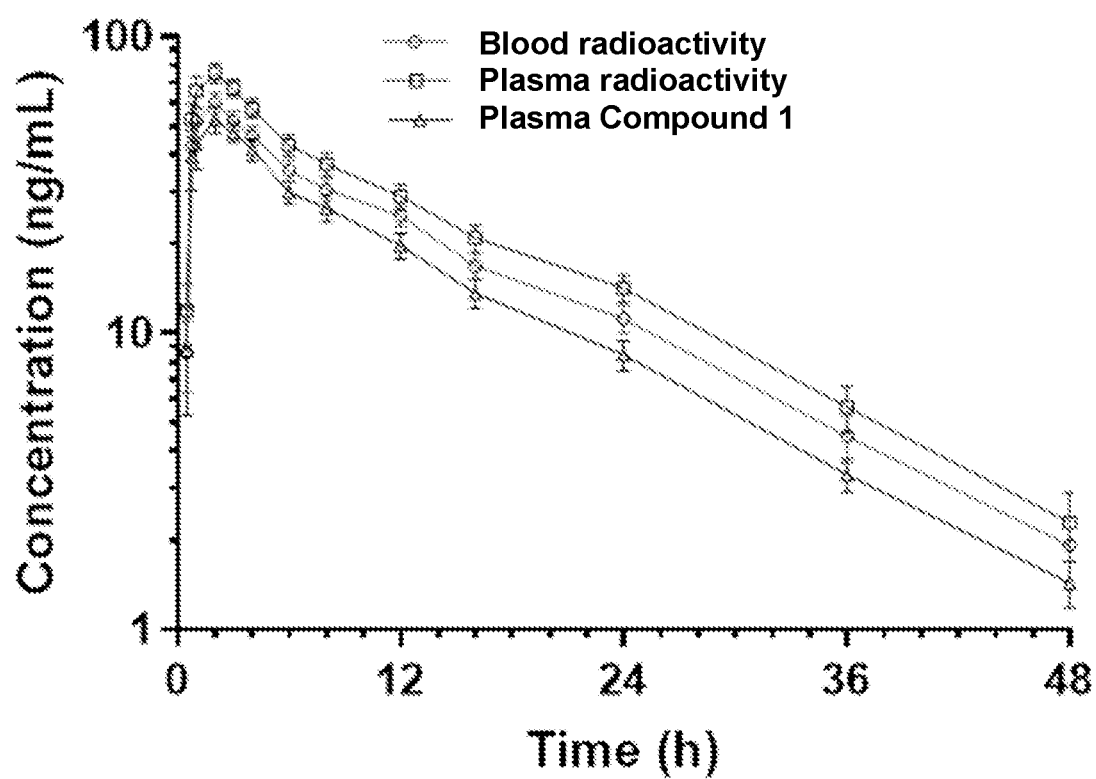
FIG. 2 is a graph showing the mean radioactivity (nM equivalents) in blood or plasma and Compound 1 (nM) in plasma following a single oral dose of approximately 13 mg [14C] Compound 1 to healthy male volunteers in the fasted state.

FIG. 2 shows the mean radioactivity (nM equivalents) in blood or plasma and Compound 1 (nM) in plasma following a single oral dose of approximately 13 mg [14C] Compound 1 to healthy male volunteers in the fasted state. The plasma total radioactivity and compound 1 had a half-life of about ten hours. The ratio of plasma Compound 1 concentration to plasma total radioactivity was about 0.7, indicating that Compound 1 is the major circulating component in plasma. The blood-to-plasma radioactivity ratios (about 0.8) indicated low association of radioactivity with blood cells.

Four minor circulating metabolites (<10% of compound-related material) were observed, as shown below:

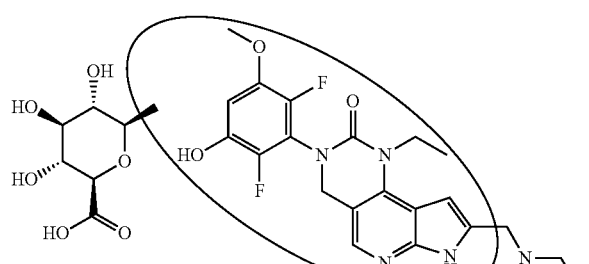

2-1

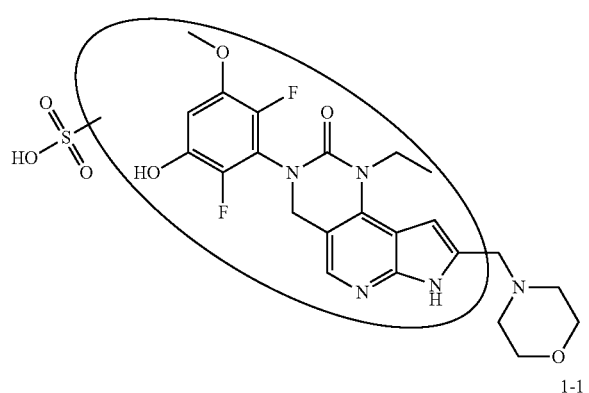

2-2

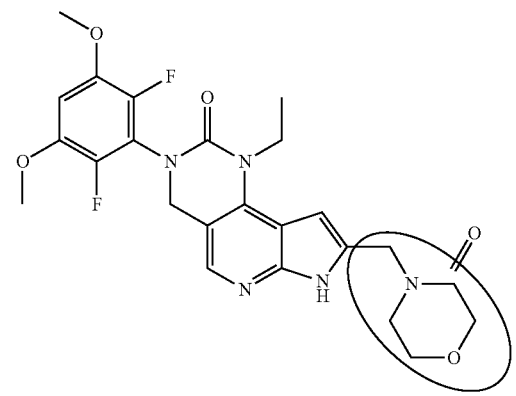

3

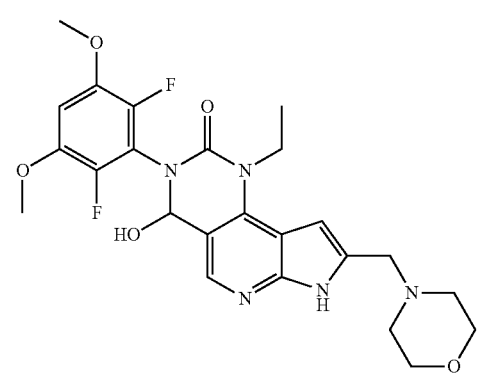

1-1 circle around certain parts of the chemical structure indicates the options for attachment of the glucuronide, sulfonic acid and keto groups.

The percentage of administered dose of each compound isolated from blood/plasma samples is shown in the table below:

| Compound | m/z | % Total Radioactivity Pool of Hamilton Pools (0-24 h) |
|---|---|---|
| 2-1 | 650.23 | 5.9 |
| 2-2 | 554.15 | 5.0 |
| 3 | 504.21 | 6.0 |
| 2-1 | 650.23 | 5.9 |
| 2-2 | 554.15 | 5.0 |
| 2 | 474.19 | ND |
| 1 | 488.21 | 64.5 |
| 1-1 | 502.19 | 6.8 |

Figure 3:
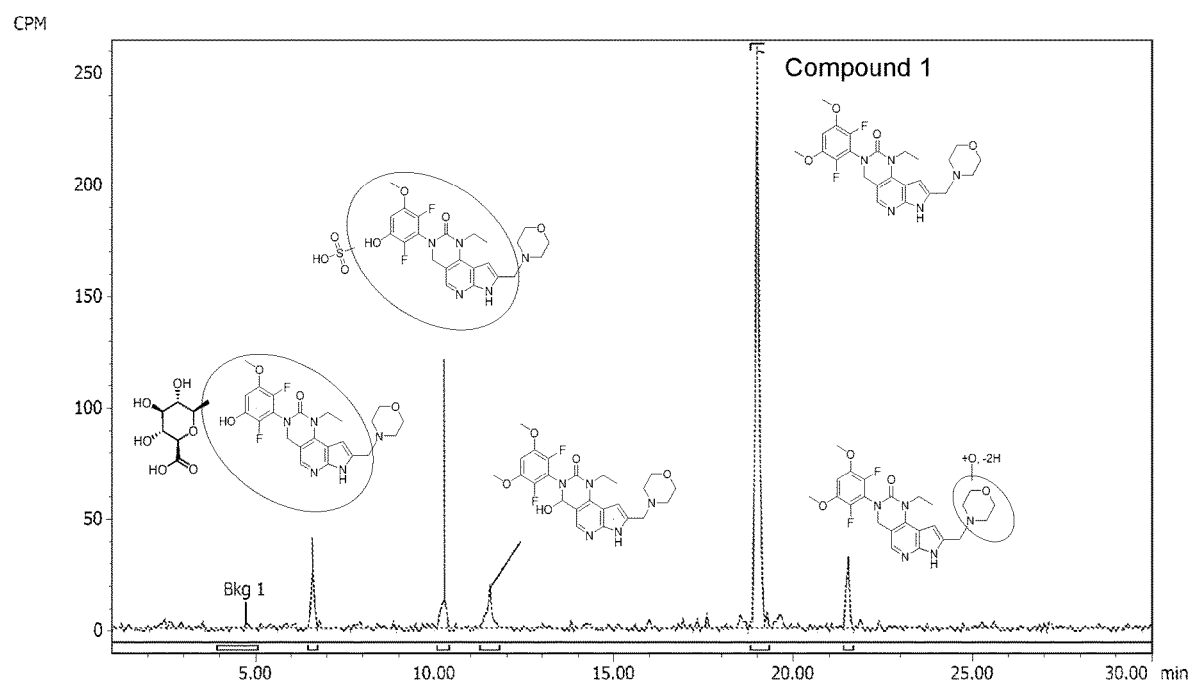
FIG. 3 shows the mass spectrum of human circulating metabolites of Compound 1.

FIG. 3 shows the mass spectrum of human circulating metabolites of Compound 1.

12.6% of the dose was recovered in urine. Two metabolites of Compound 1 were isolated from urine, as shown below:

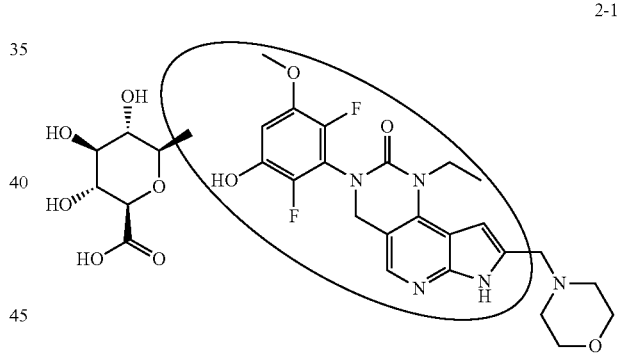

2-1

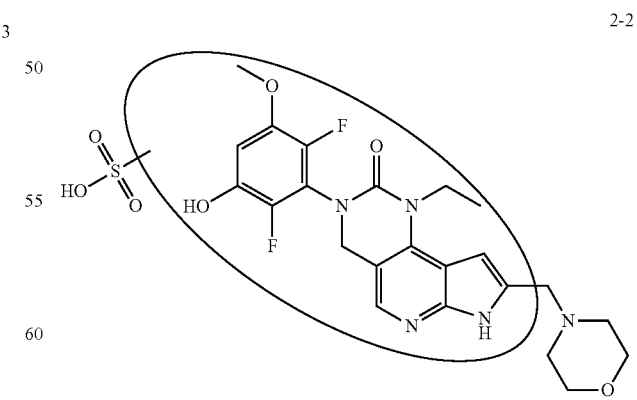

2-2

Compound 2-1 is a glucuronide derivative of Compound 2. Compound 2-2 is a sulfonic acid derivative of Compound 2. Compound 1-1 is a keto derivative of Compound 1. The circle around certain parts of the chemical structure indicates the options for attachment of the glucuronide and sulfonic acid groups.

The percentage of administered dose of each compound isolated in urine samples is shown in the table below:

| | % of Administered Dose in Urine Sample | | | | |
|---|---|---|---|---|---|
| Compound | m/z | 0-6 h | 6-12 h | 12-24 h | 24-48 h | Sum |
| 2-1 | 650.23 | 1.7 | 0.8 | 1.0 | 1.0 | 4.4 |
| 2-2 | 554.15 | 0.7 | 0.3 | 0.5 | 0.6 | 2.1 |
| 1 | 488.21 | 0.5 | 0.2 | 0.2 | 0.2 | 1.0 |

Figure 4:
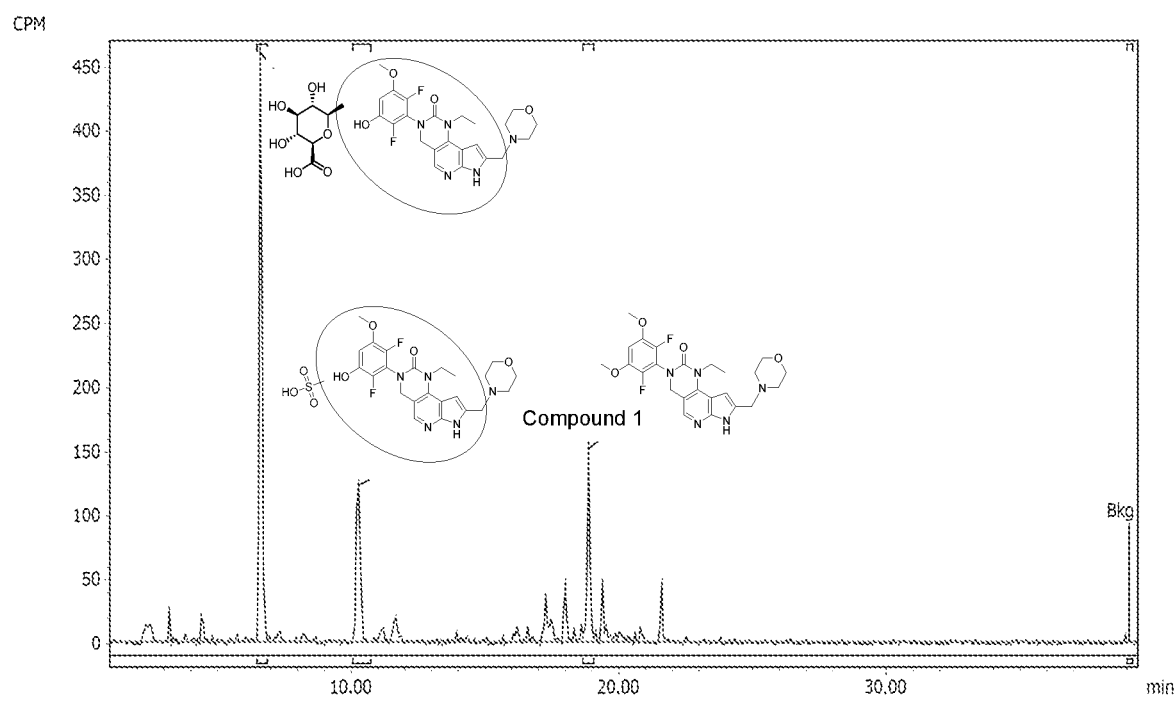
FIG. 4 shows the mass spectrum of Compound 1 metabolites isolated from urine.

FIG. 4 shows the mass spectrum of Compound 1 metabolites isolated from urine.

82.4% of the dose was recovered in feces. The following metabolites of Compound 1 were isolated from feces:

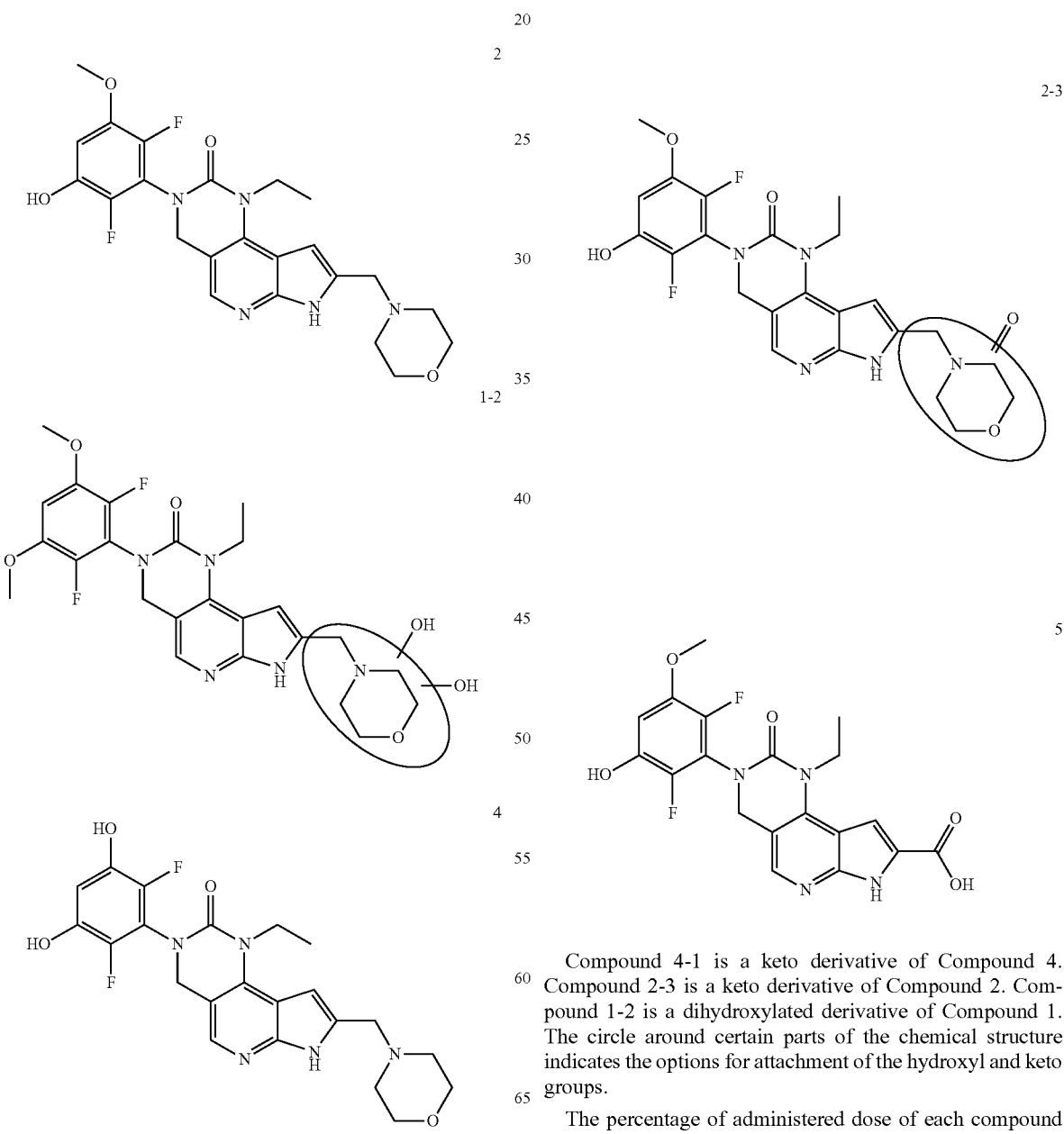

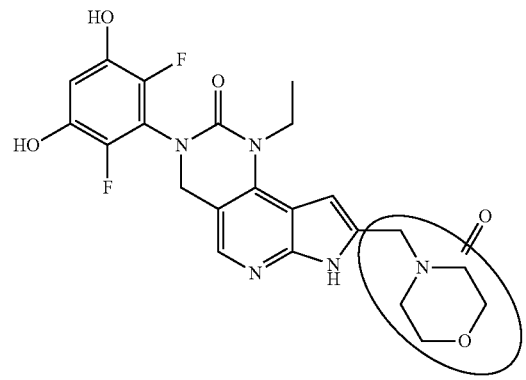

Compound 4-1 is a keto derivative of Compound 4. Compound 2-3 is a keto derivative of Compound 2. Compound 1-2 is a dihydroxylated derivative of Compound 1. The circle around certain parts of the chemical structure indicates the options for attachment of the hydroxyl and keto groups.

The percentage of administered dose of each compound isolated in feces samples is shown in the table below:

| Compound | m/z | % of Administered Dose in Feces Samples | | | | | | |
| --- | --- | --- | --- | --- | --- | --- | --- | --- |
| | | 0-24 h | 24-48 h | 48-72 h | 72-96 h | 96-120 h | 120-144 h | Sum |
| 4 | 460.18 | ND | 0.5 | 2.3 | 1.1 | 0.2 | 0.4 | 4.5 |
| 2 | 474.19 | <0.1 | 11.4 | 14.5 | 14.5 | 1.6 | 2.9 | 44.4 |
| 4-1 | 474.16 | <0.1 | 0.4 | 0.6 | 0.7 | 0.1 | 0.2 | 2.0 |
| 1-2 | 520.20 | <0.1 | 0.9 | 1.2 | 1.0 | 0.1 | 0.2 | 3.5 |
| 1 | 488.21 | 0.1 | 0.6 | 0.4 | 0.2 | 0.0 | 0.0 | 1.4 |
| 2-3 | 488.17 | <0.1 | 1.5 | 2.3 | 2.5 | 0.3 | 0.5 | 7.1 |
| 5 | 419.12 | ND | 0.4 | 0.6 | 0.5 | 0.0 | 0.1 | 1.6 |

Figure 5:
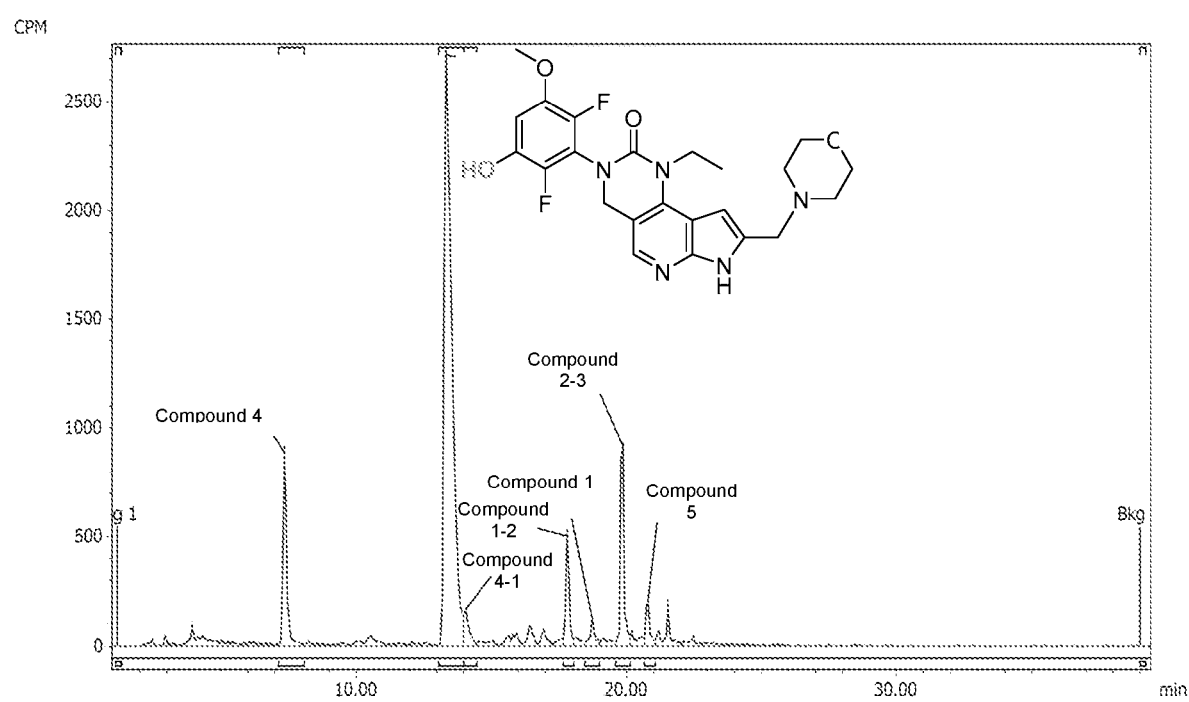
FIG. 5 shows the mass spectrum of Compound 1 metabolites isolated from feces.

FIG. 5 shows the mass spectrum of Compound 1 metabolites isolated from feces.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating cancer in a patient in need thereof comprising administering to the patient a therapeutically effective amount of a compound which is selected from:
   3-(2,6-difluoro-3-hydroxy-5-methoxyphenyl)-1-ethyl-8-(morpholinomethyl)-1,3,4,7-tetrahydro-2H-pyrrolo[3',2':5,6]pyrido[4,3-d]pyrimidin-2-one; and
   3-(2,6-difluoro-3,5-dimethoxyphenyl)-1-ethyl-4-hydroxy-8-(morpholinomethyl)-1,3,4,7-tetrahydro-2H-pyrrolo[3',2':5,6]pyrido[4,3-d]pyrimidin-2-one, or a pharmaceutically acceptable salt thereof.

2. The method of claim 1, wherein the cancer is selected from bladder cancer, breast cancer, cervical cancer, colorectal cancer, endometrial cancer, gastric cancer, head and neck cancer, kidney cancer, liver cancer, lung cancer, ovarian cancer, prostate cancer, esophageal cancer, gall bladder cancer, pancreatic cancer, thyroid cancer, skin cancer, leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's Macroglubulinemia, hairy cell lymphoma, Burkett's lymphoma, glioblastoma, melanoma, and rhabdosarcoma.

3. The method of claim 1, wherein the cancer is cholangiocarcinoma.

4. The method of claim 3, wherein the cholangiocarcinoma is advanced or metastatic cholangiocarcinoma.

5. The method of claim 1, wherein the cancer is myeloid/lymphoid neoplasms.

6. The method of claim 5, wherein the myeloid/lymphoid neoplasm is 8p11 myeloproliferative syndrome.

7. The method of claim 1, wherein the compound is 3-(2,6-difluoro-3-hydroxy-5-methoxyphenyl)-1-ethyl-8-(morpholinomethyl)-1,3,4,7-tetrahydro-2H-pyrrolo[3',2':5,6]pyrido[4,3-d]pyrimidin-2-one, or a pharmaceutically acceptable salt thereof.

8. The method of claim 1, wherein the compound is 3-(2,6-difluoro-3,5-dimethoxyphenyl)-1-ethyl-4-hydroxy-8-(morpholinomethyl)-1,3,4,7-tetrahydro-2H-pyrrolo[3',2':5,6]pyrido[4,3-d]pyrimidin-2-one, or a pharmaceutically acceptable salt thereof.

9. A method of treating cancer in a patient in need thereof comprising administering to the patient a therapeutically effective amount of a compound of Formula II:

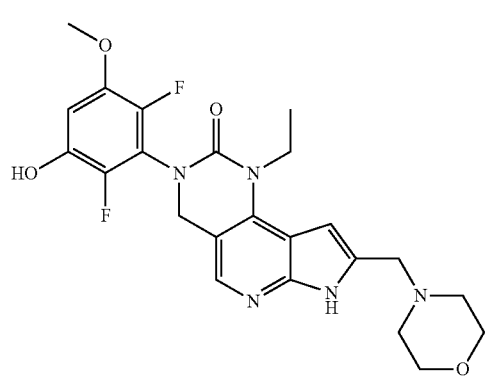

II wherein one C—H group is replaced with a C—X group, the N—H group is replaced with an N—X group, or the O—H group is replaced with an O—X group; wherein X is a group selected from:

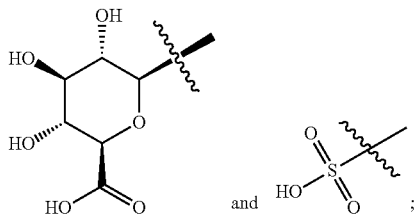

and or a pharmaceutically acceptable salt thereof.

10. The method of claim 9, wherein the cancer is selected from bladder cancer, breast cancer, cervical cancer, colorectal cancer, endometrial cancer, gastric cancer, head and neck cancer, kidney cancer, liver cancer, lung cancer, ovarian cancer, prostate cancer, esophageal cancer, gall bladder cancer, pancreatic cancer, thyroid cancer, skin cancer, leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's Macroglubulinemia, hairy cell lymphoma, Burkett's lymphoma, glioblastoma, melanoma, and rhabdosarcoma.

11. The method of claim 9, wherein the cancer is cholangiocarcinoma.

12. The method of claim 11, wherein the cholangiocarcinoma is advanced or metastatic cholangiocarcinoma.

13. The method of claim 9, wherein the cancer is myeloid/lymphoid neoplasms.

14. The method of claim 13, wherein the myeloid/lymphoid neoplasm is 8p11 myeloproliferative syndrome.

15. The method of claim 9, wherein X is

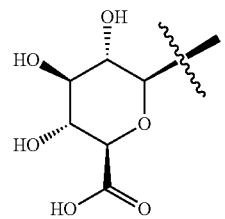

16. The method of claim 9, wherein X is

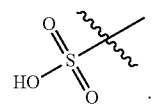

17. The method of claim 9, wherein one C—H group is replaced with a C—X group.

18. The method of claim 9, wherein the N—H group is replaced with an N—X group.

19. The method of claim 9, wherein the O—H group is replaced with an O—X group.

* * * * *

```
SEQUENCE LISTING

Sequence total quantity: 1
SEQ ID NO: 1            moltype = AA   length = 15
FEATURE                 Location/Qualifiers
REGION                  1..15
                        note = synthetic peptide
source                  1..15
                        mol_type = protein
                        organism = synthetic construct
SEQUENCE: 1
EQEDEPEGDY FEWLE                                                          15
```